United States Patent [19]
Goodby et al.

[11] Patent Number: 5,853,613
[45] Date of Patent: Dec. 29, 1998

[54] CHIRAL CYCLOHEXYL COMPOUNDS

[75] Inventors: John William Goodby; Kenneth Johnson Toyne; Michael Hird; Stephen John Lock, all of Hull, United Kingdom

[73] Assignee: Secretary of State for Defence in Her Britannic Majesty's Government of the United Kingdom of Great Britain and Northern Ireland, United Kingdom

[21] Appl. No.: 765,713

[22] PCT Filed: Jun. 29, 1995

[86] PCT No.: PCT/GB95/01538

§ 371 Date: Jan. 16, 1997

§ 102(e) Date: Jan. 16, 1997

[87] PCT Pub. No.: WO96/00710

PCT Pub. Date: Jan. 11, 1996

[30] Foreign Application Priority Data

Jun. 29, 1994 [GB] United Kingdom ........... 9412709

[51] Int. Cl.[6] .......... C09K 19/30; C09K 19/34; C09K 19/12; C07C 29/20
[52] U.S. Cl. .............. 252/299.63; 252/299.61; 252/299.66; 568/835; 558/431
[58] Field of Search .......... 252/299.63, 299.66, 252/299.61; 568/835; 558/431

[56] References Cited

U.S. PATENT DOCUMENTS

| | | | |
|---|---|---|---|
| 4,846,998 | 7/1989 | Pohl et al. | 252/299.63 |
| 4,879,061 | 11/1989 | Ferrato | 252/299.1 |
| 4,943,384 | 7/1990 | Sucrow et al. | 252/299.63 |
| 5,108,652 | 4/1992 | Eidenschink et al. | 252/299.63 |
| 5,147,577 | 9/1992 | Gray et al. | 252/299.62 |
| 5,232,625 | 8/1993 | Gray et al. | 252/299.63 |
| 5,269,965 | 12/1993 | Matsumara et al. | 252/299.63 |
| 5,358,663 | 10/1994 | Gray et al. | 252/299.66 |
| 5,384,065 | 1/1995 | Geelhaar et al. | 252/299.63 |
| 5,486,309 | 1/1996 | Gray et al. | 252/299.6 |

FOREIGN PATENT DOCUMENTS

| | | |
|---|---|---|
| 0063003A2 | 3/1982 | European Pat. Off. |
| 0374849A2 | 12/1989 | European Pat. Off. |
| 0376294A1 | 12/1989 | European Pat. Off. |
| WO A 86 05484 | 9/1986 | WIPO |
| WO A 86 05486 | 9/1986 | WIPO |

OTHER PUBLICATIONS

Chemical Abstracts 117:181967 & JP 04069352. (1995).
Chemical Abstracts 114:133345 & Mol. Cryst. Liq. Cryst (1990). 191, 259–67.
Chemical Abstracts 112:169628 & Zh.Org.Khim.(1989), 25 (11), 2399–402.
Chemical Abstracts 107:166170 & Zh. Orl. Khim. (1987), 23(6), 1268–73.
Molecular Crystals and Liquid Crystals vol. 191, (1990) pp. 259–267 Karamysheva "Liquid crystalline phenylcyclohexanes with a lateral methyl substituent".

Primary Examiner—C. H. Kelly
Attorney, Agent, or Firm—Nixon & Vanderhye

[57] ABSTRACT

The present invention describes liquid crystal compounds which are suitable for use in liquid crystal devices including those which exploit the electroclinic effect.

15 Claims, 25 Drawing Sheets

(60) R = C8H17
(61) R = C10H25
(62) R = C12H25

(32) R = C14H29
(33) R = C8H17
(34) R = C9H19
(35) R = C10H25
(36) R = C11H23
(37) R = C12H25

(83) R = C8H17
(84) R = C9H19
(85) R = C10H25
(86) R = C11H23
(87) R = C12H25
(88) R = C14H29

(97) R = C10H21
(98) R = C12H25
(99) R = C8H17
(100) R = C9H19
(101) R = C11H23
(102) R = C14H29

(103) X = F, Y = H
(104) X = H, Y = F
(105) X = F, Y = F

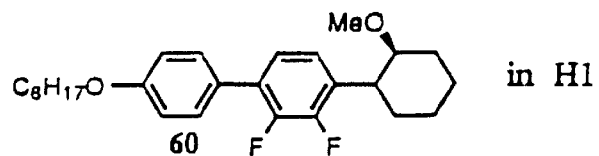
Fig.18.
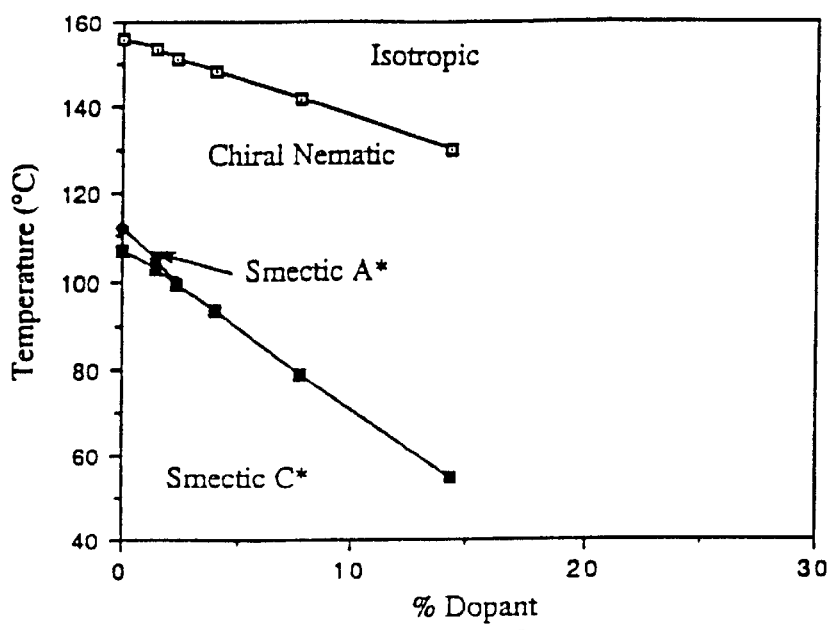
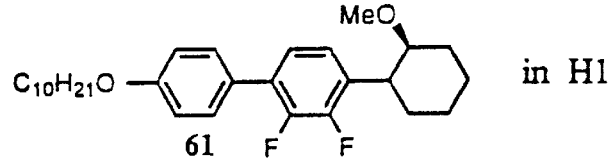
Fig.19.
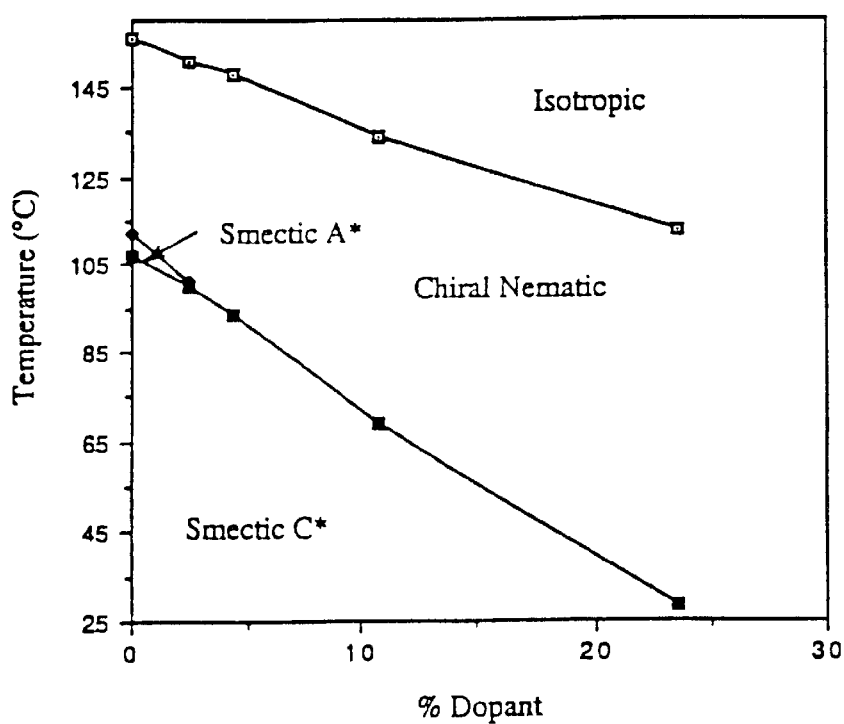

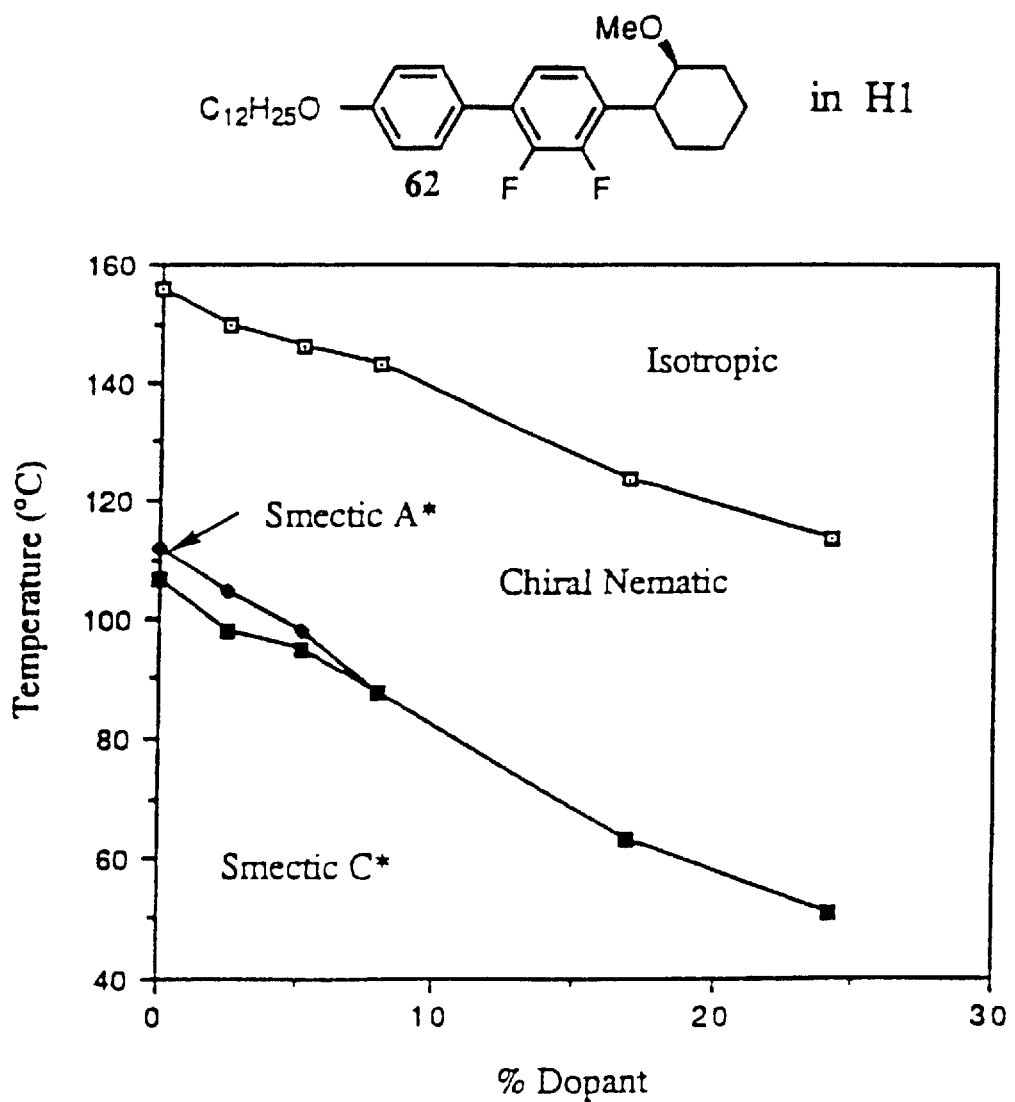

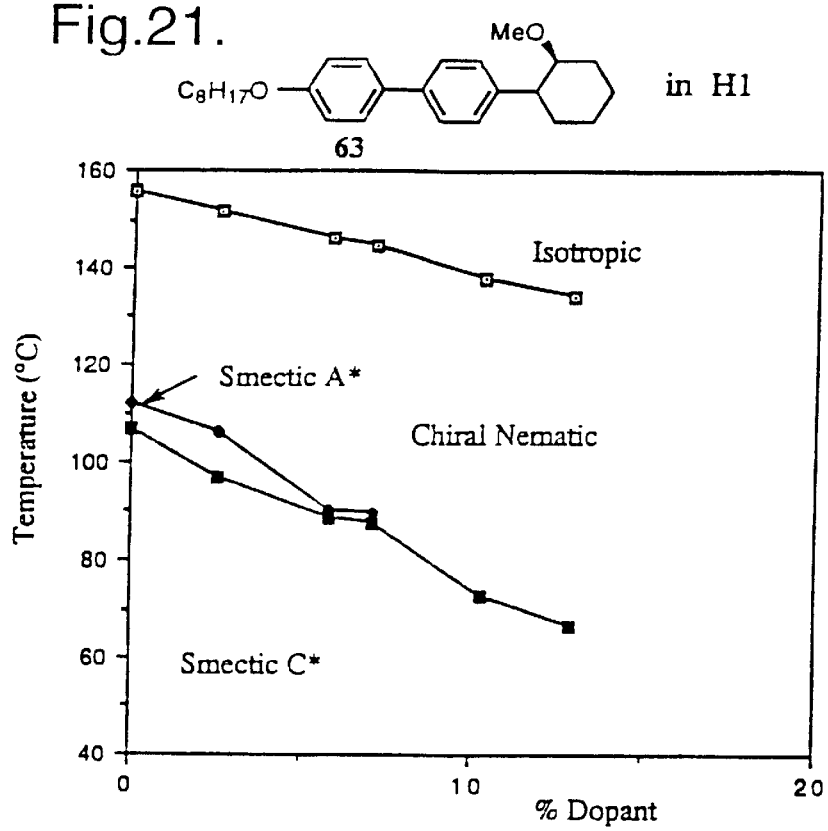
Fig.21. in H1
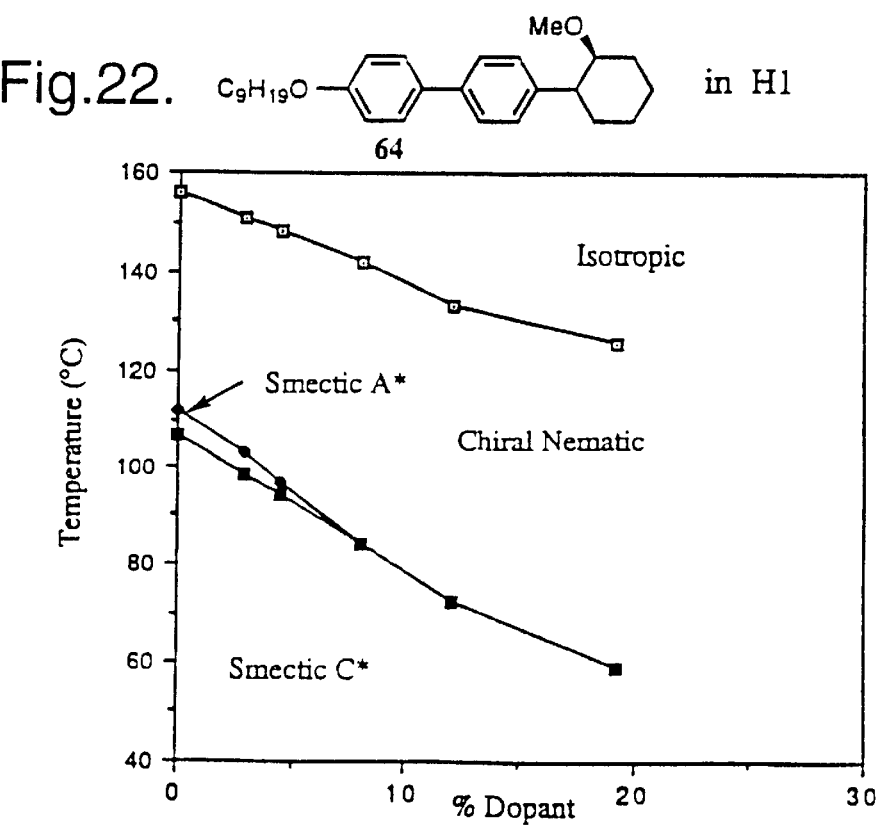
Fig.22. in H1 in H1
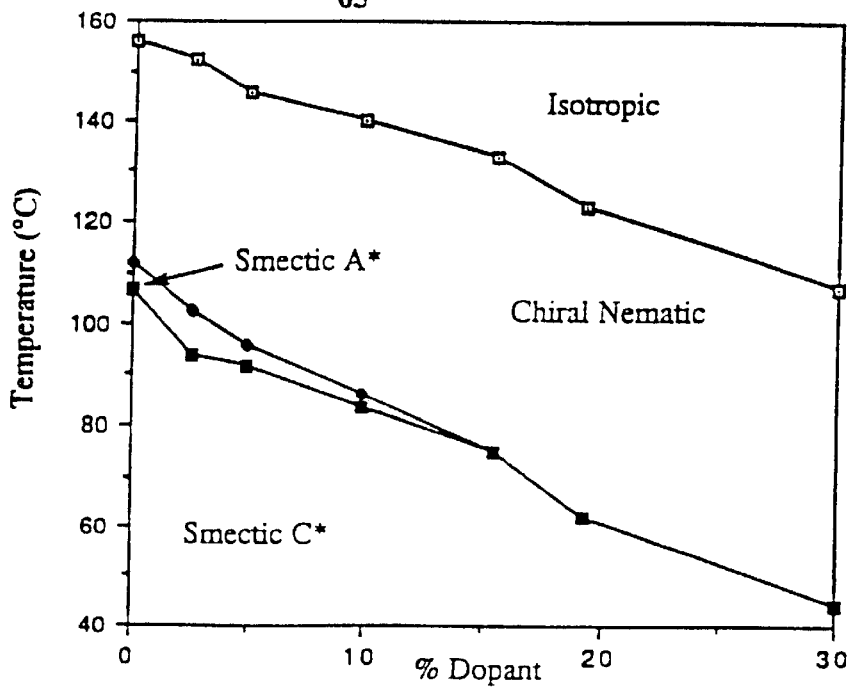
  in H1
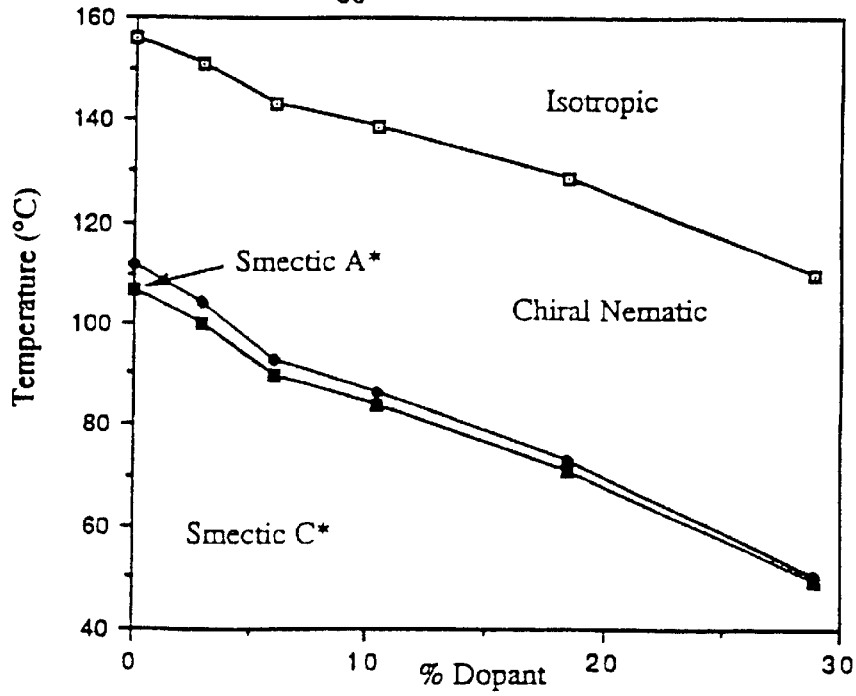

in H1
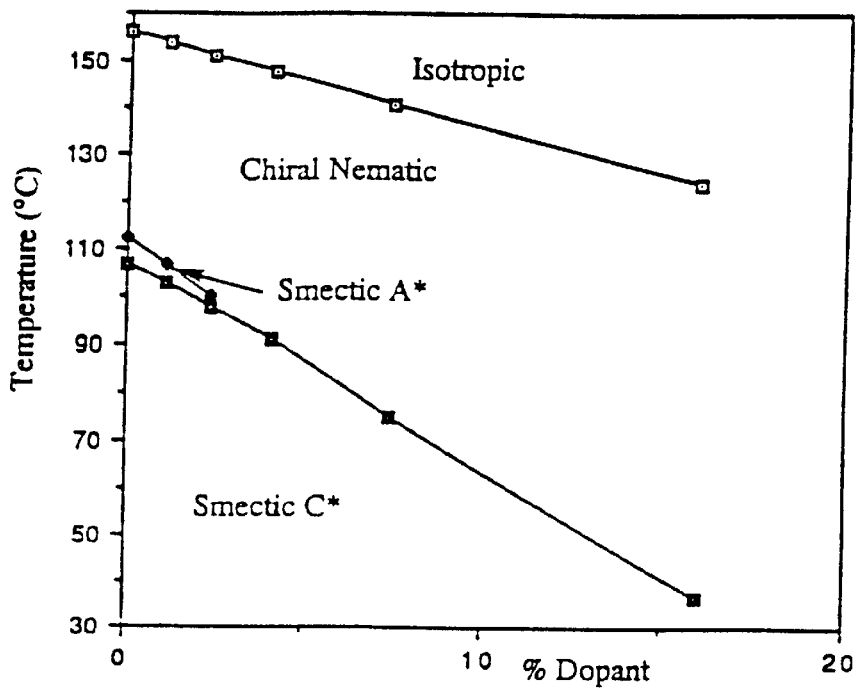
  in H1
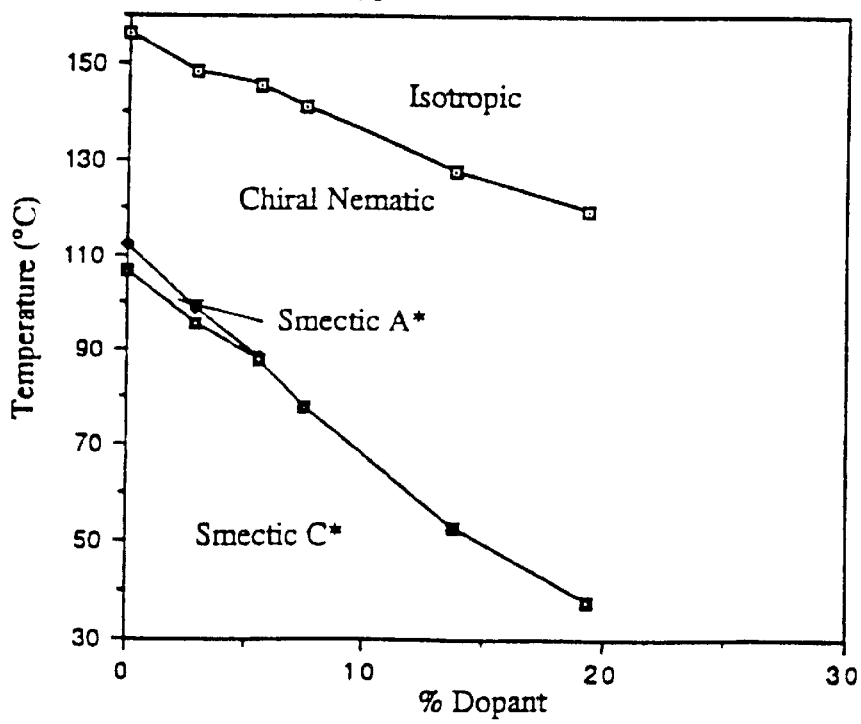

in H1
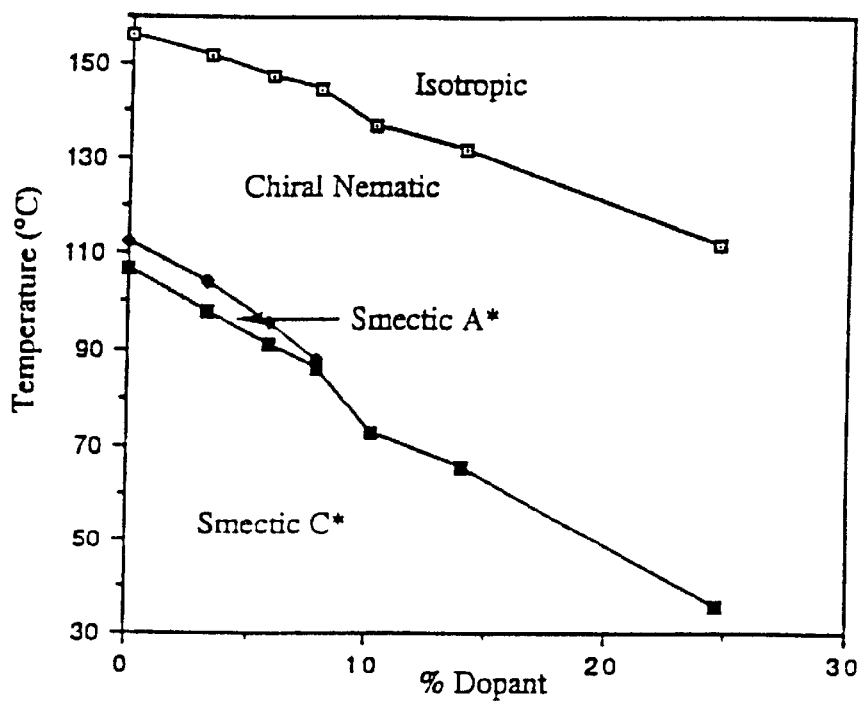
  in H1
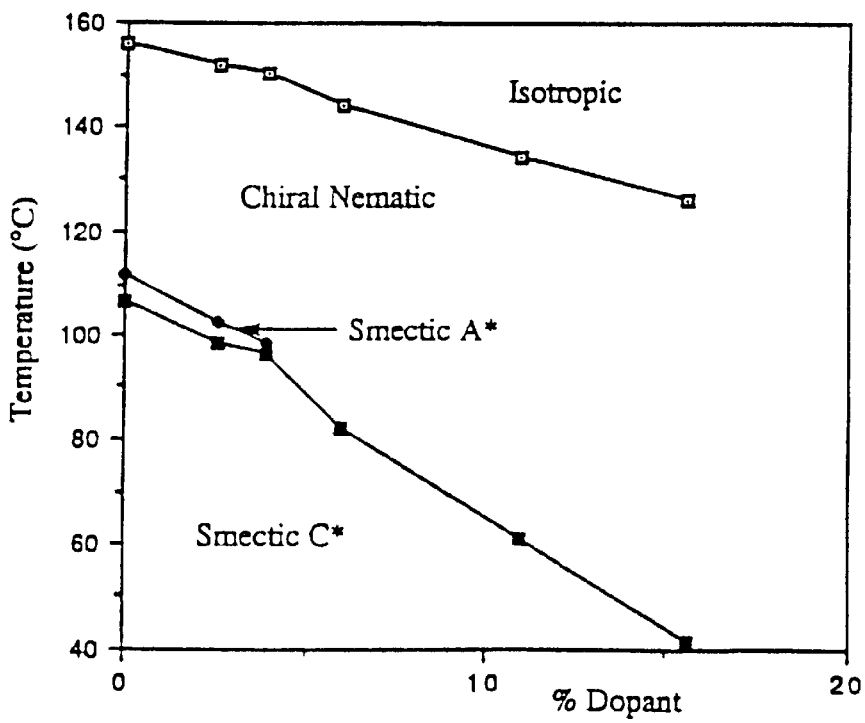

in H1
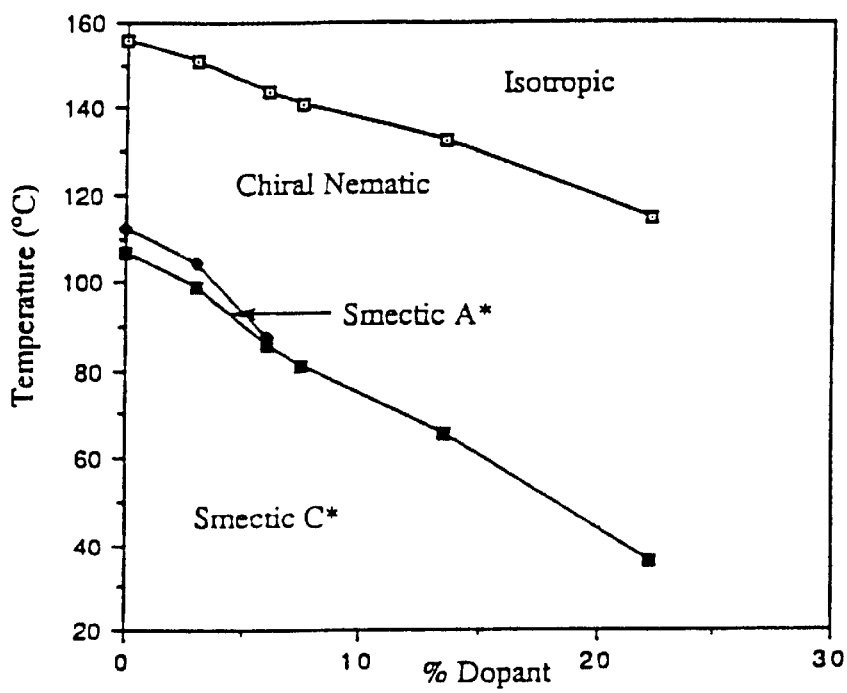
  in H1
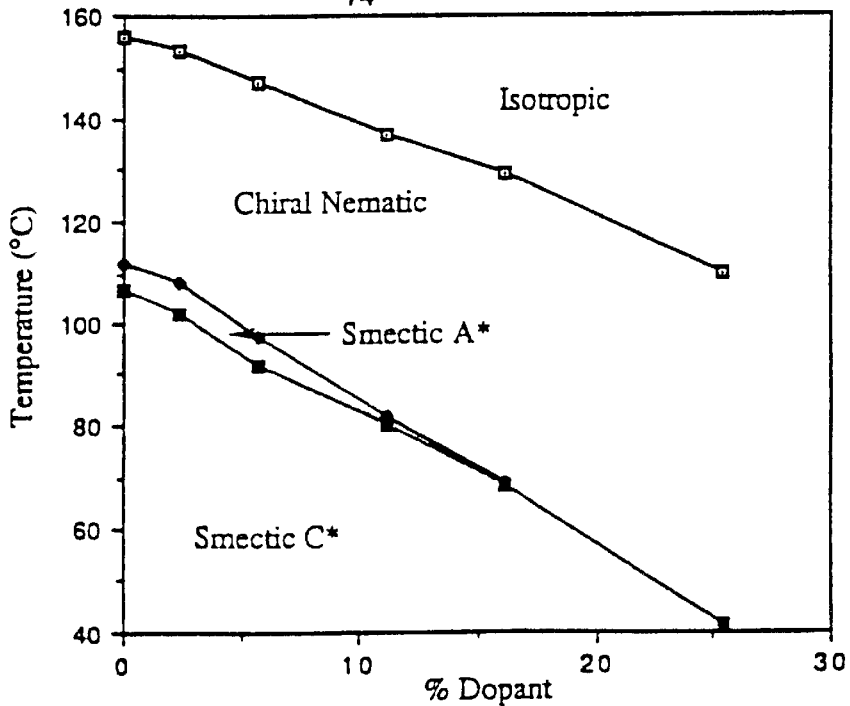

in H1
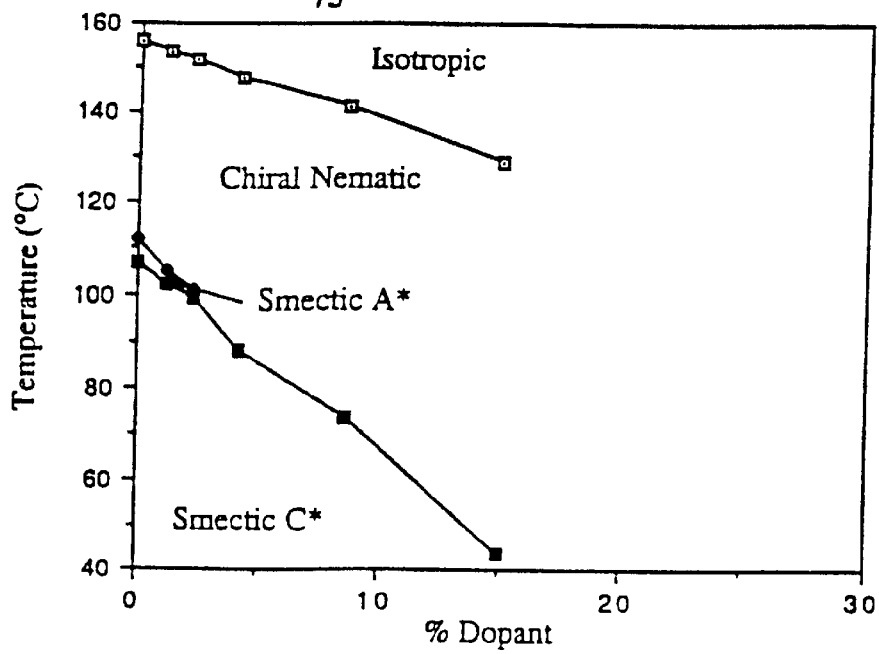
  in H1
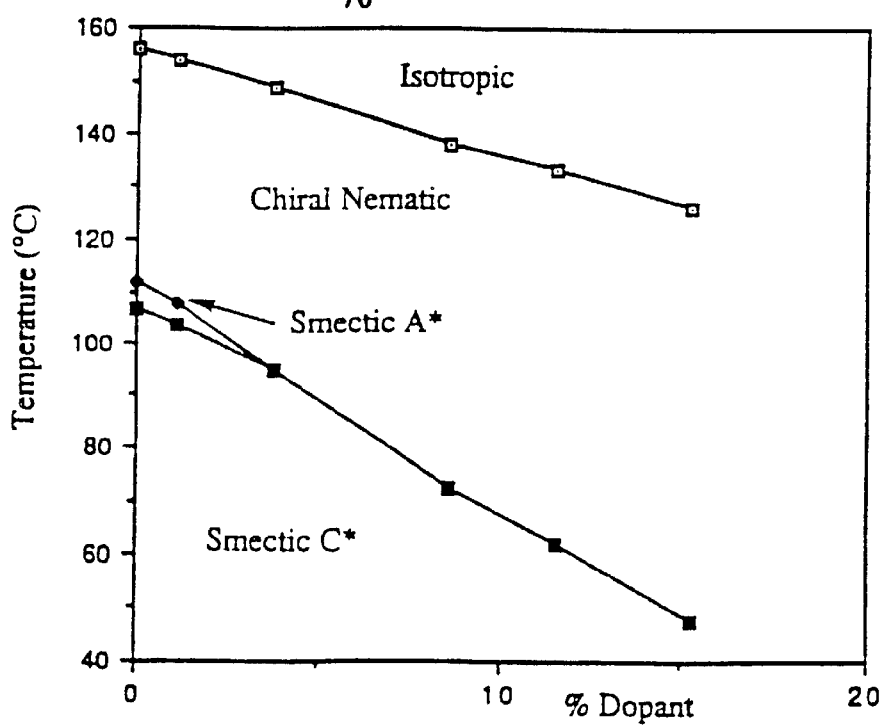

in H1
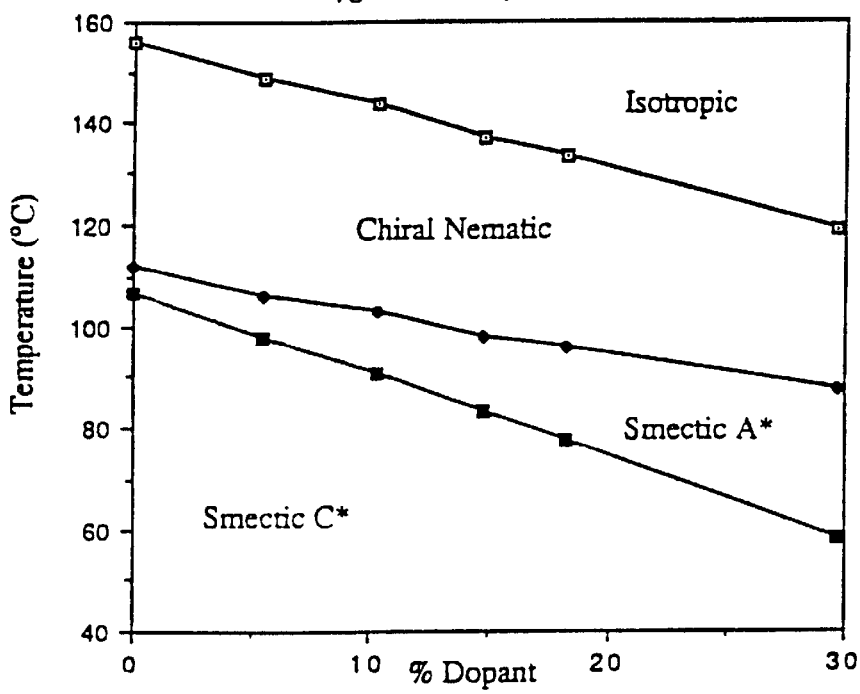
  in H1
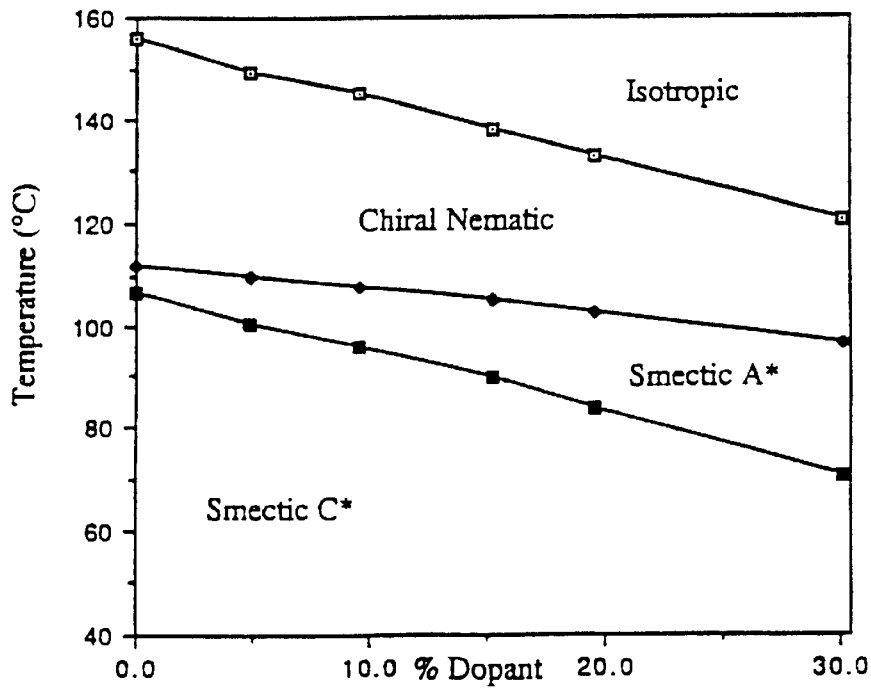

in H1
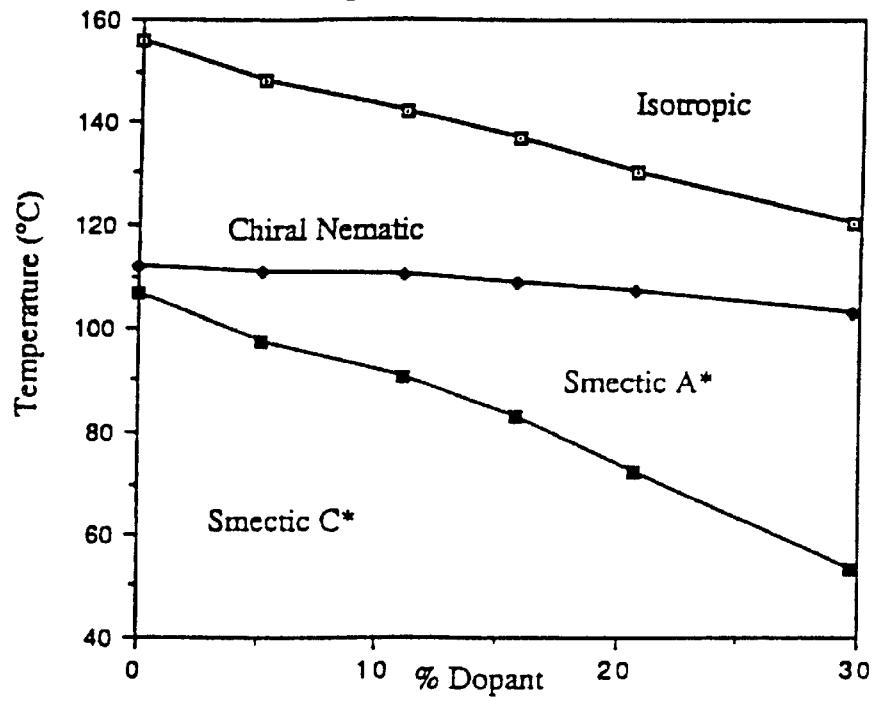
  in H1
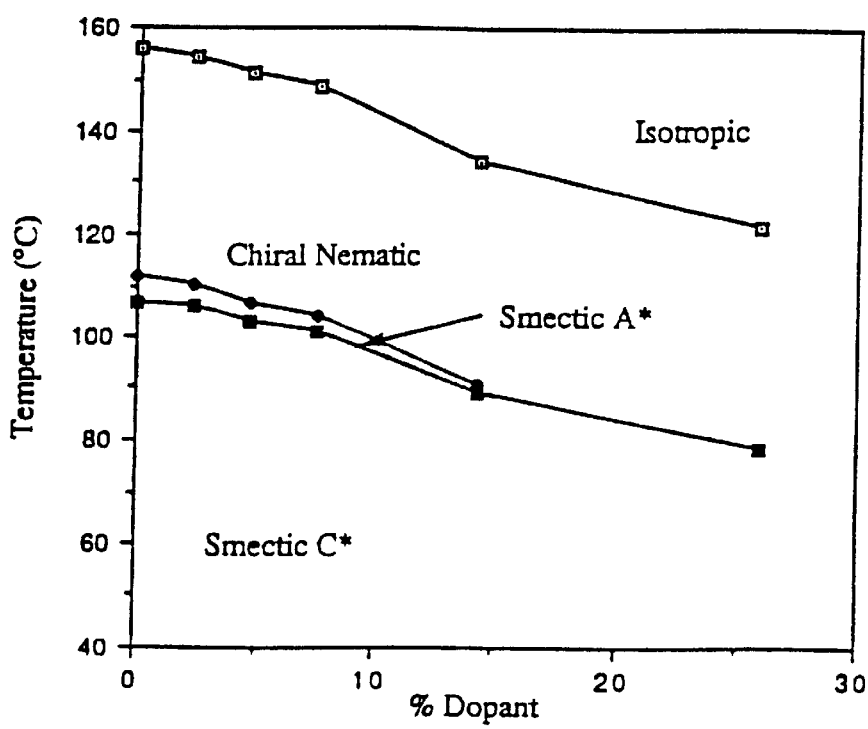

CHIRAL CYCLOHEXYL COMPOUNDS

This application is based on PCT/GB95/01538, filed Jun. 29, 1995 and GB 9412709.9, filed Jun. 29, 1994.

This invention relates to novel chiral compounds suitable for use in liquid crystal mixtures and their inclusion in liquid crystal devices.

Liquid crystals can exist in various phases. In essence there are three different classes of liquid crystalline material, each possessing a characteristic molecular arrangement. These classes are nematic, cholesteric and smectic. A wide range of smectic phases exists, for example smectic A and smectic C. Some liquid crystal materials possess a number of liquid crystal phases on varying the temperature, others have just one phase. For example, a liquid crystal material may show the following phases on being cooled from the isotropic phase:—isotropic—nematic—smectic A—smectic C—solid. If a material is described as being smectic A then it means that the material possesses a smectic A phase over a usefull working temperature range.

Most liquid crystal devices incorporate a mixture of materials selected to give desired operating characteristics. The present invention provides liquid crystal materials suitable for incorporating in a wide variety of mixtures to provide the desired characteristics suitable for use in a number of devices.

U.S. Pat. No. 4,846,998 discloses liquid crystal compounds comprising cyclohexane derivatives.

WO 86/05485 discloses liquid crystal compounds comprising cyclohexane derivatives. The cyclohexane may be substituted such that a chiral centre is present however the nature of the synthetic procedures described is such that only racemic mixtures are described. Mol. Cryst. Liq. Cryst. 1990, vol. 191, pp259–67 also discusses liquid crystal compounds comprising cyclohexane derivatives—this document is limited to use of a methyl substituent on the cyclohexane and there appears to be no discussion of stereochemistry.

According to this invention there are provided compounds having a general Formula I:

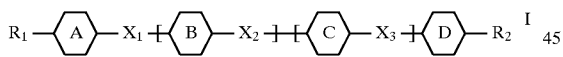

wherein A, B, C, D are independently selected from any of phenyl, pyridine, pyrimidine, cyclohexyl, substituted phenyl and at least one of the cyclohexyl groups:

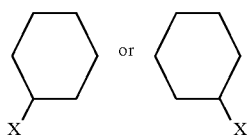

must be present:

wherein X may be any one of OH, $OR_3$, $R_3$, $CH_2OR_3F$, Cl, $OCF_3$, $CF_3$, $CH_2F$, $CHF_2$, CN, where $R_3$ is $C_{1-5}$ alkyl and may itself contain a chiral centre;

$R_1$ may be $C_{1-16}$ straight or branched chain alkyl or alkoxy and may contain a chiral centre;

$R_2$ may be $C_{1-16}$ straight or branched chain alkyl or alkoxy and may contain a chiral centre or $R_2$ is H;

substituted phenyl is given by the formula:

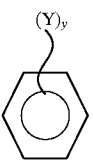

wherein Y may be individually selected from F, Cl or CN and y may be 1–4;

$X_1$, $X_2$ and $X_3$ are linking groups and are independently selected from single bond, $CH_2O$, $OCH_2$, COO, OCO, $CH_2CH_2$;

b and c are independently 0 or 1.

Preferably those groups A, B, C, D which are not given by the cyclohexyl groups:

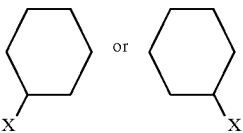

are phenyl or substituted phenyl;

Preferably X is selected from any one of OH, $OR_3$, $R_3$, F, $CF_3$, $CH_2F$, $CHF_2$, CN, wherein $R_3$ is a methyl group or an ethyl group;

Preferably $R_1$ is $C_{4-12}$ alkyl or alkoxy and $R_2$ is $C_{4-12}$ alkyl or alkoxy or H;

Y if present is F and y=1 or 2;

Preferably $X_1$, $X_2$ and $X_3$ are independently selected from single bond, $CH_2O$ or $OCH_2$;

Preferably the total of b and c is 1 or 2.

Compounds of Formula I can be included in a material, the material being a mixture of compounds.

The materials of this aspect of the invention may be used in many of the known forms of liquid crystal display devices, for example chiral smectic electro-optic devices. Such a device may comprise a layer of liquid crystal material contained between two spaced cell walls bearing electrode structures and surface treated to align liquid crystal material molecules. The liquid crystal mixtures may have many applications including in ferroelectric, thermochromic and electroclinic devices.

Ferroelectric smectic liquid crystal materials, which can be produced by mixing an archiral host and a chiral dopant, use the ferroelectric properties of the tilted chiral smectic C, F, G, H, I, J and K phases. The chiral smectic C phase is denoted $S_C^*$ with the asterisk denoting chirality. The $S_C$ phase is generally considered to be the most useful as it is the least viscous. Ferroelectric smectic liquid crystal materials should ideally possess the following characteristics: low viscosity, controllable spontaneous polarisation (Ps) and an $S_C$ phase that persists over a broad temperature range which should include ambient temperature and exhibits chemical and photochemical stability. Materials which possess these characteristics offer the prospect of very fast switching liquid crystal containing devices. Some applications of ferroelectric liquid crystals are described by J. S. Patel and J. W. Goodby in Opt. Eng., 1987, 26, 273.

In ferroelectric liquid crystal devices the molecules switch between different alignment directions depending on the polarity of an applied electric field. These devices can be arranged to exhibit bistability where the molecules tend to remain in one of two states until switched to the other switched state. Such devices are termed surface stabilised ferroelectric devices, eg as described in U.S. Pat. No. 5,061,047 and U.S. Pat. No. 4,367,924 and U.S. Pat. No. 4,563,059. This bistability allows the multiplex addressing of quite large and complex devices.

One common multiplex display has display elements, ie pixels, arranged in an X, y matrix format for the display of eg alpha numeric characters. The matrix format is provided by forming the electrodes on one slide as a series of column electrodes, and the electrodes on the other slide as a series of row electrodes. The intersections between each column and row form addressable elements or pixels. Other matrix layouts are known, eg seven bar numeric displays.

There are many different multiplex addressing schemes. A common feature involves the application of a voltage, called a strobe voltage to each row or line in sequence. Coincidentally with the strobe applied at each row, appropriate voltages, called data voltages, are applied to all column electrodes. The differences between the different schemes lies in the shape of the strobe and data voltage waveforms.

Other addressing schemes are described in GB-2,146, 473-A; GB-2,173,336-A; GB-2,173,337-A; GB-2,173629-A; WO 89/05025; Harada et al 1985 S.I.D. Paper 8.4 pp 131–134; Lagerwall et al 1985 I.D.R.C. pp 213–221 and P. Maltese et al in Proc 1988 I.D.R.C. pp 90–101 Fast Addressing for Ferroelectric LC Display Panels.

The material may be switched between its two states by two strobe pulses of opposite sign, in conjunction with a data waveform. Alternatively, a blanking pulse may be used to switch the material into one of its states. Periodically the sign of the blanking and the strobe pulses may be alternated to maintain a net d.c. value.

These blanking pulses are normally greater in amplitude and length of application than the strobe pulses so that the material switches irrespective of which of the two data waveforms is applied to any one intersection. Blanking pulses may be applied on a line by line basis ahead of the strobe, or the whole display may be blanked at one time, or a group of lines may be simultaneously blanked.

It is well known in the field of ferroelectric liquid crystal device technology that in order to achieve the highest performance from devices, it is important to use mixtures of compounds which give materials possessing the most suitable ferroelectric smectic characteristics for particular types of devices.

Devices can be assessed for speed by consideration of the response time vs pulse voltage curve. This relationship may show a minimum in the switching time ($t_{min}$) at a particular applied voltage ($V_{min}$). At voltages higher or lower than $V_{min}$ the switching time is longer than $t_{min}$. It is well understood that devices having such a minimum in their response time vs voltage curve can be multiplex driven at high duty ratio with higher contrast than other ferroelectric liquid crystal devices. It is preferred that the said minimum in the response time vs voltage curve should occur at low applied voltage and at short pulse length respectively to allow the device to be driven using a low voltage source and fast frame address refresh rate.

Typical known materials (where materials are a mixture of compounds having suitable liquid crystal characteristics) which do not allow such a minimum when included in a ferroelectric device include the commercially available materials known as SCE13 and ZLI-3654 (both supplied by Merck UK Ltd, Poole, Dorset). A device which does show such a minimum may be constructed according to PCT GB 88/01004 and utilising materials such as eg commercially available SCE8 (Merck UK Ltd). Other examples of prior art materials are exemplified by PCT/GB 86/00040, PCT GB 87/00441 and UK 2232416B.

Materials possessing a smectic A ($S_A$) phase may exhibit an electroclinic effect. The electroclinic effect was first described by S. Garoff and R. Meyer, Phys. Rev. Lett., 38, 848 (1977). An electroclinic device has also been described in UK patent application GB-2 244 566 A. This particular device helps to overcome the poor alignment problems of electroclinic (EC) devices using a surface alignment that gives a surface tilt within a small range of angles.

When a smectic A phase is composed of chiral molecules, it may exhibit an electroclinic effect, ie a direct coupling of molecular tilt to applied field. The origin of the electroclinic effect in a smectic A phase composed of chiral polar molecules has been described by Garoff and Meyer as follows. The application of an electric field parallel to the smectic layers of such a smectic A phase biases the free rotation of the transverse molecular dipoles and therefore produces a non-zero average of the transverse component of the molecular polarization. When such a dipole moment is present and coupled to the molecular chirality, a tilt of the long molecular axis (the director) is induced in a plane perpendicular to the dipole moment.

In thin samples for example 1–3 mm and with the smectic layers tilted or perpendicular with respect to the glass plates the electroclinic effect is detectable at low applied fields.

In an aligned smectic A sample a tilt of the director is directly related to a tilt of the optic axis. The electroclinic effect results in a linear electro-optic response. The electro-optic effect can manifest itself as a modulation of the effective birefringence of the device.

Electroclinic (EC) devices are useful, for example in spatial light modulators having an output that varies linearly with applied voltage. A further advantage of EC devices is that they have high speed response times, much faster than twisted nematic type devices. Unlike ferroelectric devices the EC device is not bistable and has an output that varies linearly with applied voltage.

The electroclinic effect is sometimes referred to as the soft-mode effect see G Andersson et al in Appl. Phys. Lett., 51, 9, (1987).

In general terms, regarding the electroclinic effect, it is advantageous if on applying a small voltage there results a large induced tilt. An increase in induced tilt may result in an increase in contrast ratio. It is also advantageous if a large induced tilt can be obtained at as low a voltage as possible.

It is also advantageous if the relationship between molecular induced tilt and applied voltage is temperature independent. When an increase in applied voltage results in little or no change in induced tilt then the material being tested is generally referred to as exhibiting a saturation voltage effect.

By $S_A^*$ is meant a $S_A$ phase which contains some proportion of chiral molecules. Cholesteric or chiral nematic liquid crystals possess a twisted helical structure which is capable of responding to a temperature change through a change in the helical pitch length. Therefore as the temperature is changed then the wavelength of the light reflected from the planar cholesteric structure will change and if the reflected light covers the visible range then distinct changes in colour occur as the temperature varies. This means that there are many possible applications including the areas of thermography and thermooptrics.

The cholesteric mesophase differs from the nematic phase in that in the cholesteric phase the director is not constant in space but undergoes a helical distortion. The pitch length for the helix is a measure of the distance for the director to turn through 360°.

By definition, a cholesteric material is chiral material. Cholesteric materials may also be used in electro-optical displays as dopants, for example in twisted nematic displays where they may be used to remove reverse twist defects, they may also be used in cholesteric to nematic dyed phase change displays where they may be used to enhance contrast by preventing wave-guiding.

Thermochromic applications of cholesteric liquid crystal materials usually use thin film preparations of the cholesterogen which are then viewed against a black background. These temperature sensing devices may be placed into a number of applications involving thermometry, medical thermography, non-destructive testing, radiation sensing and for decorative purposes. Examples of these may be found in D. G. McDonnell in Thermotropic Liquid Crystals, Critical Reports on Applied Chemistry, Vol 22, edited by G. W. Gray, 1987 pp 120–44; this reference also contains a general description of thermochromic cholesteric liquid crystals.

Generally, commercial thernochromic applications require the formulation of mixtures which possess low melting points, short pitch lengths and smectic transitions just below the required temperature-sensing region. Preferably the mixture or material should retain a low melting point and high smectic-cholesteric transition temperatures.

In general, thermochromic liquid crystal devices have a thin film of cholestergen sandwiched between a transparent supporting substrate and a black absorbing layer. One of the fabrication methods involves producing an 'ink' with the liquid crystal by encapsulating it in a polymer and using printing technologies to apply it to the supporting substrate. Methods of manufacturing the inks include gelatin microencapsulation. U.S. Pat. No. 3,585,318 and polymer dispersion, U.S. Pat. Nos. 1,161,039 and 3,872,050. One of the ways for preparing well-aligned thin-film structures of cholesteric liquid crystals involves laminating the liquid crystal between two embossed plastic sheets. This technique is described in UK patent 2,143,323.

The materials of the present invention may also be incorporated into polymer dispersed liquid crystal (PDLC) type devices such as those described in PCT/GB90/01947 and references therein. In such devices liquid crystal material is dispersed in a polymer matrix.

For a review of thermochromism in liquid crystals see J. G. Grabmaier in 'Applications of Liquid Crystals', G. Meier, E. Sackmann and J. G. Grabmaier, Springer-Verlag, Berlin and New York, 1975, pp 83–158.

For all the above applications it is not usual for a single compound to exhibit all of the properties highlighted, for example ferroelectric smectic liquid crystal materials generally consist of a mixture of compounds which when mixed together induce a chiral tilted smectic phase. Chiral dopants are added to a liquid crystalline mixture in order to induce the smectic mixture to become chiral smectic and to induce a Ps in the material, or if the material already possesses a Ps then the introduction of a chiral dopant should result in a change of value for Ps.

The invention will now be described by way of example only with reference to the accompanying drawings of which:

FIGS. 18–40 illustrate phase diagrams for compounds 60–82 in host material H1.

Figure 43:
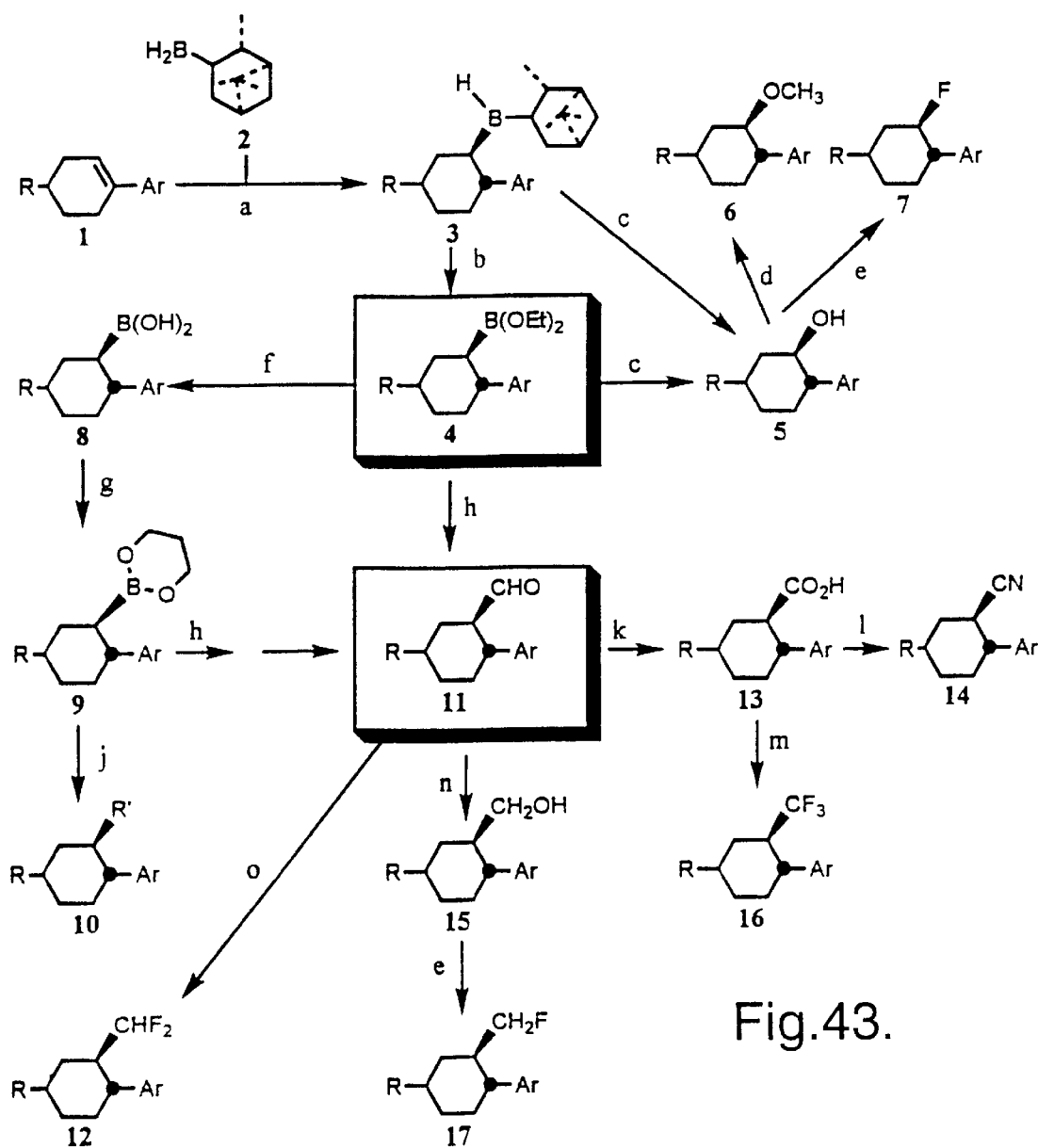
FIG. 43 illustrates synthetic schemes.
Figure 44:
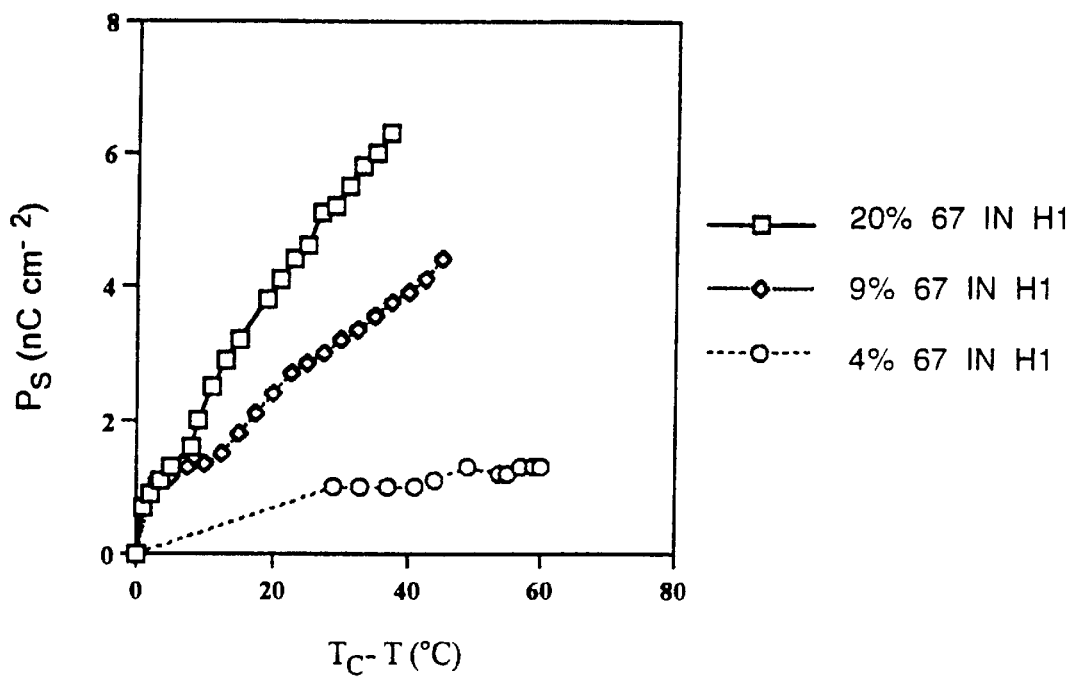
FIG. 44 illustrates the spontaneous polarisation (Ps) of ferroelectric mixtures of 67 in H1 as a function of temperature.
Figure 45:
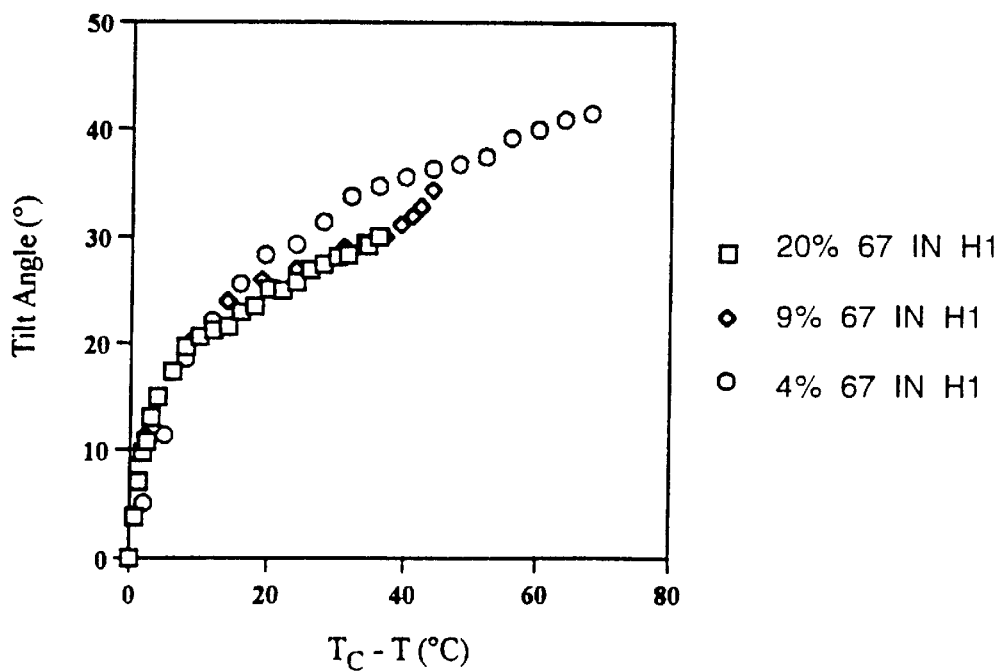
FIG. 45 illustrates the tilt angle of ferroelectric mixtures of chiral dopants in H1 as a function of temperature.

Reagents used in the synthetic routes of FIGS. 1 to 17b are shown below in corresponding schemes 1 to 17b. Scheme 18 refers to FIG. 43.

Scheme 1 a. n-Buli, −78° C., B(OMe)$_3$, HCl
b. H$_2$O$_2$, THF at reflux
c. R-Br, K$_2$CO$_3$, acetone at reflux
d. n-BuLi, −78° C., B(OMe)$_3$, HCl Scheme 2 a. R-Br, K$_2$CO$_3$, acetone at reflux
b. n-BuLi, −78° C., B(OMe)$_3$, HCl

Scheme 3 a. Bromine, glacial acetic acid, 5° C.
b. R-Br, K$_2$CO$_3$, acetone at reflux
c. n-BuLi, −78° C., B(OMe)$_3$, HCl Scheme 4 a. R-Br, K$_2$CO$_3$, acetone at reflux
b. (i) Mg in THF at reflux;
  (ii) at −78° C. B(OMe)$_3$, HCl
c. n-BuLi, −78° C., B(OMe)$_3$, HCl Scheme 5 a. 1-Bromododecane, K$_2$CO$_3$, acetone at reflux
b. n-BuLi, −78° C., B(OMe)$_3$, HCl Scheme 6 a. (i) n-BuLi, −78° C., cyclohexanone;
  (ii) p-Toluene sulphonic acid in toluene at reflux Scheme 7 a. BF$_3$.OEt$_2$ in THF under nitrogen at ambient temperature
b. (i) THF under nitrogen at ambient temperature for 7 days
  (ii) 3 Molar NaOH, 30% H$_2$O$_2$, reflux for 1 hour
c. NaH, MeI in DMF over night at ambient temperature Scheme 8 a. n-BuLi, −78° C., B(OMe)$_3$, HCl
b. Na$_2$CO$_3$, Pd(PPh$_3$)$_4$ in 1,2-dimethoxyethane, water at reflux, over night

Scheme 9 a. $BF_3.OEt_2$ in THF under nitrogen at ambient temperature
b. (i) THF under nitrogen at ambient temperature for 7 days
   (ii) 3 Molar NaOH, 30% $H_2O_2$, reflux for 1 hour
c. NaH, MeI in DMF over night at ambient temperature
d. n-BuLi, −78° C., $B(OMe)_3$, HCl
e. $Na_2CO_3$, $Pd(PPh_3)_4$ in 1,2-dimethoxyethane, water at reflux, over night

Scheme 10 a. $Na_2CO_3$, $Pd(PPh_3)_4$ in 1,2-dimethoxyethane, water at reflux, over night

Scheme 11 a. $Na_2CO_3$, $Pd(PPh_3)_4$ in 1,2-dimethoxyethane, water at reflux, over night
b. $Na_2CO_3$, $Pd(PPh_3)_4$ in 1,2-dimethoxyethane, water at reflux, over night

Scheme 12 a. $Na_2CO_3$, $Pd(PPh_3)_4$ in 1,2-dimethoxyethane, water at reflux, over night

Scheme 13 a. $Na_2CO_3$, $Pd(PPh_3)_4$ in 1,2-dimethoxyethane, water at reflux, over night
b. $Na_2CO_3$, $Pd(PPh_3)_4$ in 1,2-dimethoxyethane, water at reflux, over night
c. $Na_2CO_3$, $Pd(PPh_3)_4$ in 1,2-dimethoxyethane, water at reflux, over night
d. $Na_2CO_3$, $Pd(PPh_3)_4$ in 1,2-dimethoxyethane, water at reflux, over night

Scheme 14 a. $Na_2CO_3$, $Pd(PPh_3)_4$ in 1,2-dimethoxyethane, water at reflux, over night

Scheme 15 a. $Na_2CO_3$, $Pd(PPh_3)_4$ in 1,2-dimethoxyethane, water at reflux, over night
b. $Na_2CO_3$, $Pd(PPh_3)_4$ in 1,2-dimethoxyethane, water at reflux, over night
c. $Na_2CO_3$, $Pd(PPh_3)_4$ in 1,2-dimethoxyethane, water at reflux, over night

Scheme 16 a. $BF_3.OEt_2$ in THF under nitrogen at ambient temperature
b. (i) THF under nitrogen at ambient temperature for 5 days, methylcyclohex-1-ene
   (ii) 3 Molar NaOH, 30% $H_2O_2$, reflux for 1 hour -continued

Scheme 16 c. Bromo-iodo-benzene, $Na_2CO_3$, $Pd(PPh_3)_4$ in 1,2-dimethoxyethane, water at reflux, over night
d. $Na_2CO_3$, $Pd(PPh_3)_4$ in 1,2-dimethoxyethane, water at reflux, over night
e. n-BuLi, −78° C., $B(OMe)_3$, HCl
f. Bromo-iodo-benzene $Na_2CO_3$, $Pd(PPh_3)_4$ in 1,2-dimethoxyethane, water at reflux, over night

Scheme 17 a. $Na_2CO_3$, $Pd(PPh_3)_4$ in 1,2-dimethoxyethane, water at reflux, over night

Scheme 17b a. $Na_2CO_3$, $Pd(PPh_3)_4$ in 1,2-dimethoxyethane, water at reflux, over night

Scheme 18 a. THF
b. $CH_3CHO$
c. $H_2O_2$
d. (i) NaH
   (ii) $CH_3I$
e. DAST
f. (i) NaOH
   (ii) H*
g. $HO(CH_2)_3OH$, pentane
h. (i) Methoxymethylphenyl sulfide, sec-Buli
   (ii) $HgCl_2$
   (iii) $H_2O_2$
j. RI, Pd(O)
k. Chromic acid, ether
l. (i) Oxalyl chloride
   (ii) $NH_3$
   (iii) thionyl chloride, DMF
m. $SF_4$
n. $LiAlH_4$
o. (i) $HS(CH_2)_2SH$, $BF_3.2HOAc$
   (ii) HF/pyridine DAST = Diethylaminosulphurtrifluoride
FIG. 43/scheme 18 illustrates how the substituent at the chiral centre is varied.

Most of the synthetic schemes outlined are based on chiral hydroboration methods described by Brown and co-workers, see references, Rangaishenvi et al, J. Org. Chem., 1991, 56, 3286; Brown et al, J. Am. Chem. Soc., 1985, 107,4980; Brown et al Pure and Applied Chemistry. 1991,63,307.

Experimental

Confirmation of the structures of intermediates and products was obtained by $^1H$ NMR spectroscopy (JEOL JNM-GX270 spectrometer), infrared spectroscopy (Perkin-Elmer 783 spectrophotometer) and mass spectrometry (Finnigan-MAT 1020 GC/MS spectrometer). Elemental analysis (Fisons EA1108 CHN) was obtained for each final compound prepared. The progress of reactions was frequently monitored using a Perkin-Elmer 8320 capillary gas chromatograph fitted with a 12 m QC2/BPI-1.0 SGE column. Transition temperatures, spontaneous polarization ($P_S$) and tilt angle (q) were measured using a Mettler FP5 hot-stage and control unit in conjunction with an Olympus BH2 polarising microscope. Transition temperatures were confirmed using differential scanning calorimetry (Perkin-Elmer DSC-7 and IBM data station). Spontaneous polarization was measured using a Diamant bridge. The purities of intermediates were checked by GLC analysis (see above) and the purity of each final compound was checked by HPLC analysis (Microsorb C18 80-215-C5 RP column) and were found to be >99% pure in each case.

The enantiomeric excess of alcohols 52, 54, 57, 92 was determined from the preparation of diastereomeric Mosher esters using R-(+)-α-methoxy-(trifluoromethyl)-phenylacetic acid chloride (Mosher acid chloride) and was found to be 99%. The enantiomeric excess values of the subsequent chiral materials were assumed to be 99%.

Tetrakis(triphenylphosphine)palladium(0) was prepared according to the literature procedure. Compounds 25, 47 and 41 were purchased from Aldrich. H1 host material was purchased from Merck Limited (Poole, UK). Compounds 1, 10, 17, 44 were purchased from Fluorochem. Compound 38 was purchased from Avocado. Compound 18 is synthesised from 3-fluorophenol (Fluorochem Ltd, Old Glossop) by a fast bromination at −5° C. ($Br_2$, acetic acid). Methylcyclohex-1-ene was purchased from Merck.

2,3-Difluoro-phenylboronic acid (2). n-Butyllithium (53 ml, 2.5M in hexane, 0.133 mol) was added dropwise to a stirred, cooled (−78° C.) solution of compound 1 (15 g, 0.132 mol) in dry THF (140 ml) under dry nitrogen. The reaction mixture was maintained under these conditions for 2.5 h and then a solution of trimethyl borate (27.4 g, 0.264 mol) in dry THF (50 ml) was added dropwise at −78° C. The reaction mixture was allowed to warm to room temperature overnight and then stirred for 1 h with 10% hydrochloric acid (120 ml). The product was extracted into ether (twice), and the combined etheral extracts were washed with water and dried ($MgSO_4$). The solvent was removed in vacuo to yield a white solid.

Crude yield 18.3 g (88%); $^1$H NMR ($CDCl_3$) d 7.10(q), 7.15(t), 7.50(s, broad), 7.65(t); IR (KCl) vmax 3700–3000, 1625, 1470, 1360, 1270, 1045, 905 $cm^{-1}$; MS m/z 158 ($M^+$), 140, 125, 114.

2,3-Difluoro-phenol (3). 10% Hydrogen peroxide (135 ml, 0.396 mol) was added dropwise to a stirred refluxing solution of compound 2 (19.8 g, 0.126 mol) in ether. The stirred mixture was heated under reflux for 2.5 h and cooled. The ether layer was separated and the aqueous layer was washed with ether. The combined etheral layers were washed with sodium hydroxide (3×150 ml, 10%) and the separated aqueous layer extracted was acidified with hydrochloric acid (90 ml, 36%). The product was extracted into ether (twice), and the combined etheral extracts were washed with water and dried ($MgSO_4$). The solvent was removed in vacuo. This crude product was recrystallised from petroleum spirit (40°–60° C.) to give an off white solid.

Yield 9.84 g (60%); mp 29.5°–31.5° C.; $^1$H NMR ($CDCl_3$) d 5.35(1H, s), 6.65–6.80 (2H, m), 6.95(1H, q); IR (KCl) vmax 3700–3000, 1630, 1540, 1515, 1490, 1480, 1350, 1310, 1250, 1190, 1020 $cm^{-1}$; MS m/z 130 ($M^+$), 110, 101.

1,2-Difluoro-3-octyloxybenzene (4). A solution of 1-bromooctane (8.96 g, 0.054 mol) in acetone (20 ml) was added dropwise to a stirred refluxing mixture of compound 3 (7.00 g, 0.054 mol) and potassium carbonate (22.73 g, 0.165 mol) in acetone (150 ml). The stirred mixture was heated under reflux for 12 h. The potassium carbonate was filtered off, water was added to the filtrate and the product was extracted into ether (twice). The combined ether extracts were washed with water. 5% sodium hydroxide, water and dried ($MgSO_4$). The solvent was removed in vacuo to yield colourless liquid. This crude product was purifed by column chromatography (silica gel/dichloromethane).

Yield 11.02 g (84%); bp 108°–110° C. at 0.9 mmHg,$^1$H NMR ($CDCl_3$) d 0.85 (3H, t), 1.30 (10H, m), 1.80 (2H, quint), 4.00 (2H, t), 6.75 (2H, m), 6.95 (1H, m); IR (KCl) vmax 2920, 2860, 1630, 1510, 1460, 1390, 1310, 1295, 1250, 1210, 1090 $cm^{-1}$; MS m/z 242 ($M^+$), 130, 112, 83, 70.

1,2-Difluoro-3-decyloxybenzene (5). Quantities: compound 3 (7.00 g, 0.054 mol) in acetone (150 ml), 1-bromodecane (11.95 g, 0.054 mol) in acetone (20 ml), potassium carbonate (22.73 g, 0.165 mol). The experimental procedure was as described for the preparation of compound 4. This crude product was purified by column chromatography (silica gel/dichloromethane) to give a colourless liquid.

Yield 13.64 g (94%); bp 142°–144° C. at 1.5 mmHg; $^1$H NMR ($CDCl_3$) d 0.85 (3H, t), 1.30 (14H, m), 1.80 (2H, quint), 4.00 (2H, t), 6.70 (2H, m), 6.95 (1H, m); IR (KCl) vmax 2920, 2850, 1620, 1510, 1480, 1460, 1390, 1315, 1290, 1250, 1220, 1160, 1080 $cm^{-1}$; MS m/z 270 ($M^+$), 140, 130, 111, 97, 82.

1,2-Difluoro-3-dodecyloxybenzene (6). Quantities: compound 3 (7.00 g, 0.054 mol) in acetone (150 ml), 1-bromodecane (13.43 g, 0.054 mol) in acetone (20 ml), potassium carbonate (22.73 g, 0.165 mol). The experimental procedure was as described for the preparation of compound 4. This crude product was purified by column chromatography (silica gel/dichloromethane) to give a colourless solid.

Yield 15.24 g (95%); mp 19°–20° C.; $^1$H NMR ($CDCl_3$) d 0.85 (3H, t), 1.30 (18H, m), 1.75 (2H, quint), 4.00 (2H, t), 6.70 (2H, m), 6.95 (1H, m); IR (KCl) vmax 2920, 2850, 1620, 1510, 1480, 1460, 1390, 1310, 1295, 1250, 1210, 1170, 1090 $cm^{-1}$; MS m/z 298 ($M^+$), 168, 140, 130, 125, 111, 97, 83.

2,3-Difluoro-4-octyloxyphenylboronic acid (7). Quantities: compound 4 (7.26 g, 0.03 mol) in anhydrous THF (96 ml), n-butyllithium (15 ml, 2.5M in hexane, 0.0375 mol), trimethyl borate (6.25 g, 0.060 mol) in anhydrous THF (30 ml). The experimental procedure was as described for the preparation of compound 2.

Crude yield of an off white solid 6.43 g (75%); $^1$H NMR ($CDCl_3$) d 0.85 (3H, t), 1.30 (10H, m), 1.70 (2H, quint), 4.10 (2H, t), 6.90 (1H, m), 7.40 (1H,m), 8.10 (1H, broad s); IR (KCl) vmax 3100–3600, 2960, 2920, 2880, 1640, 1510, 1500, 1465, 1350, 1300, 1210, 1090, 1055, 1010 $cm^{-1}$; MS m/z 286 ($M^+$), 258, 174, 146, 130, 112, 83.

2,3-Difluoro-4-decyloxyphenylboronic acid (8). Quantities: compound 5 (5.48 g, 0.02 mol) in anhydrous THF (40 ml), n-butyllithium (8.1 ml. 2.5M in hexane, 0.02 mol), trimethyl borate (4.16 g, 0.04 mol) in anhydrous THF (50 ml). The experimental procedure was as described for the preparation of compound 2.

Crude yield of an off white solid 6.99 g (95%); $^1$H NMR ($CDCl_3$) d 0.85 (3H, t), 1.30 (14H, m), 1.70 (2H, quint), 4.05 (2H, t), 6.95 (1H, m), 7.30 (1H, m), 8.15 (1H, broad s); IR (KCl) vmax 3000–3700, 2950, 2920, 2850, 1620, 1565, 1510, 1500, 1460, 1350, 1300, 1220, 1160, 1130, 1110, 1080, 1060, 1030, 1020 $cm^{-1}$; MS m/z 314 ($M^+$), 286, 258, 146, 140, 130, 110, 96, 82, 69.

2,3-Difluoro-4-dodecyloxyphenylboronic acid (9). Quantities: compound 6 (13.33 g, 0.0447 mol) in anhydrous THF (150 ml), n-butyllithium (25 ml, 2.5M in hexane, 0.0625 mol), trimethyl borate (9.33 g, 0.09 mol) in anhydrous THF (25 ml). The experimental procedure was as described for the preparation of compound 2.

Crude yield of an off white solid 16.44 g (108%); $^1$H NMR (CDCl$_3$) d 0.85, (3H, t), 1.30 (18H, m), 1.70 (2H, quint), 4.05 (2H, t), 6.95 (1H, m), 7.30 (1H, m), 8.15 (1H, broad s); IR (KCl) vmax 3100–3600, 2990, 2960, 2915, 2880, 1620, 1505, 1500, 1465, 1355, 1300, 1210, 1125, 1085, 1060, 1025 cm$^{-1}$; MS m/z 347 (M$^+$), 315, 147, 130, 112, 98, 84.

1-Bromo-3-fluoro-4-octyloxybenzene (11). Quantities: compound 10 (20.80 g, 0.109 mol) in acetone (300 ml), 1-bromooctane (21.05 g, 0.109 mol) in acetone (30 ml), potassium carbonate (46 g, 0.33 mol). The experimental procedure was as described for the preparation of compound 4. This crude product was purified by column chromatography (silica gel/dichloromethane) to give a colourless liquid.

Yield 29.46 g (89%); bp 137°–139° C. at 1.3 mmHg; $^1$H NMR (CDCl$_3$) d 0.85 (3H, t), 1.30 (10H, m), 1.80 (2H, quint), 4.00 (2H, t), 6.80 (1H, t), 7.20 (2H, m); IR (KCl) vmax 2920, 2860, 1580, 1495, 1460, 1410, 1390, 1300, 1275, 1260, 1240, 1205, 1130, 1070, 1020 cm$^{-1}$; MS m/z 302 (M$^+$), 190, 161, 111, 94, 71, 63, 57.

1-Bromo-3-fluoro-4-decyloxybenzene (12). Quantities: compound 10 (20.80 g, 0.109 mol) in acetone (300 ml), 1-bromodecane (21.05 g, 0.109 mol) in acetone (30 ml), potassium carbonate (46 g, 0.33 mol). The experimental procedure was as described for the preparation of compound 4. This crude product was purified by column chromatography (silica gel/dichloromethane) to give a colourless liquid.

Yield 34.26 g (95%); bp 170°–172° C. at 2.8 mmHg; $^1$H NMR (CDCl$_3$) d 0.85 (3H, t), 1.30 (14H, m), 1.80 (2H, quint), 4.00 (2H, t), 6.80 (1H, t), 7.20 (2H, m); IR (KCl) vmax 2920, 2850, 1580, 1495, 1460, 1410, 1390, 1300, 1280, 1260, 1240, 1205, 1130, 1070, 1020 cm$^{-1}$; MS m/z 330 (M$^+$), 192, 163, 140, 111, 97, 83, 69.

1-Bromo-3-fluoro-4-dodecyloxybenzene (13). Quantities: compound 10 (20.80 g, 0.109 mol) in acetone (300 ml), 1-bromodecane (27.17 g, 0.109 mol) in acetone (30 ml), potassium carbonate (46 g, 0.33 mol). The experimental procedure was as described for the preparation of compound 4. This crude product was purified by column chromatography (silica gel/dichloromethane) to give a colourless liquid.

Yield 38.02 g (97%); bp 176°–178° C. at 1.1 mmHg; $^1$H NMR (CDCl$_3$) d 0.85 (3H, t), 1.30 (18H, m), 1.80 (2H, quint), 4.00 (2H, t), 6.80 (1H, t), 7.20 (2H, m); IR (KCl) vmax 2920, 2850, 1580, 1495, 1460, 1410, 1390, 1310, 1280, 1260, 1240, 1205, 1130, 1070, 1020 cm$^{-1}$; MS m/z 360 (M$^+$), 190, 111, 97, 883, 69, 63, 55.

3-Fluoro-4-octyloxyphenylboronic acid (14). Quantities: compound 11 (10.00 g, 0.033 mol) in anhydrous THF (132 ml), n-butyllithium (16 ml, 2.5M in hexane, 0.04 mol), trimethyl borate (6.87 g, 0.066 mol) in anhydrous THF (50 ml). The experimental procedure was as described for the preparation of compound 2.

Crude yield of an off white solid 8.72 g (99%); $^1$H NMR (CDCl$_3$) d 0.90 (3H, t), 1.30 (10H, m), 1.80 (2H, quint), 4.00 (2H, t), 7.00 (2H, m), 7.90 (1H,m), no obvious OH absorption; IR (KCl) vmax 3100–3600, 2990, 292, 2850, 1610, 1500, 1460, 1410, 1350, 1315, 1220, 1130, 1085, 1020 cm$^{-1}$; MS m/z 526, 414, 320, 138, 128, 112, 83, 69.

3-Fluoro-4-decyloxyphenylboronic acid (15). Quantities: compound 12 (9.84 g, 0.03 mol) in anhydrous THF (120 ml), n-butyllithium (12.5 ml, 2.5M in hexane, 0.031 mol), trimethyl borate (6.24 g, 0.06 mol) in anhydrous THF (50 ml). The experimental procedure was as described for the preparation of compound 2.

Crude yield of a colourless liquid 8.79 g (99%); $^1$H NMR (CDCl$_3$) d 0.90 (3H, t), 1.30 (14H, m), 1.80 (2H, quint), 4.00 (2H, t), 7.00 (2H, m), 7.90 (1H, m), no obvious OH absorption; IR (KCl) vmax 3100–3700, 2950, 2920, 2850, 1610, 1500, 1460, 1420, 1380, 1305, 1280, 1250, 1200, 1140, 1100, 1020 cm$^{-1}$; MS m/z 492, 414, 320, 190, 151, 112, 97, 83, 69.

3-Fluoro-4-dodecyloxyphenylboronic acid (16). Quantities: compound 13 (10.00 g, 0.039 mol) in anhydrous THF (150 ml), n-butyllithium (17 ml, 2.5M in hexane, 0.0425 mol), trimethyl borate (8.12 g, 0.078 mol) in anhydrous THF (50 ml). The experimental procedure was as described for the preparation of compound 2.

Crude yield of a colourless liquid 9.64 g (107%); $^1$H NMR (CDCl$_3$) d 0.90 (3H, t), 1.30 (18H, m), 1.80 (2H, quint), 4.00 (2H, t), 7.00 (2H, m), 7.80 (1H, m), no obvious OH absorption; IR (KCl) vmax 3100–3600, 2920, 2850, 1605, 1500, 1455, 1410, 1350, 1305, 1270, 1220, 1130, 1090, 1020 cm$^{-1}$; MS m/z 414, 320, 138, 128, 112, 97, 83, 69.

4-Bromo-2-fluorophenol (18). Bromine (72.12 g, 0.45 mol) in glacial acetic acid (40 ml) was added to a stirred solution of 17 (50.02 g, 0.45 mol) in glacial acetic acid (200 ml) over 5 min at 5° C. The mixture was stirred for 5 min and poured into water (1000 ml). The product was extracted into dichloromethane (twice), and the combined dichloromethane extracts were washed with brine (300 ml) and water (300 ml) and dried (MgSO$_4$). The solvent was removed in vacuo to yield a crude product which was recrystallised from petroleum spirit (40°–60° C.) at 0° C. to give an off white solid.

Yield 64.4 g (75%); mp 32.5°–33.5° C.; $^1$H NMR (CDCl$_3$) d 6.0 (1H, broad s), 1.30, 6.60 (2H, double doubet), 6.85 (1H, t); IR (KCl) vmax 3000–3500, 1605, 1595, 1495, 1455, 1380, 1350, 1295, 1250, 1225, 1155, 1120, 1040 cm$^{-1}$; MS m/z 192 (M$^+$), 111, 95, 83.

1-Bromo-2-fluoro-4-octyloxybenzene (19). Quantities: compound 18 (8.02 g, 0.042 mol) in acetone (116 ml), 1-bromooctane (8.11 g, 0.042 mol) in acetone (12 ml), potassium carbonate (17.73 g, 0.109 mol. The experimental procedure was as described for the preparation of compound 4. This crude product was purified by column chromatography (silica gel/dichloromethane) to give a colourless liquid.

Yield 11.96 g (94%); bp 142°–144° C. at 2.4 mmHg; $^1$H NMR (CDCl$_3$) d 0.85 (3H, t), 1.30 (10H, m), 1.80 (2H, quint), 3.90 (2H, t), 6.65 (2H, m), 7.40 (1H, t); IR (KCl) vmax 2920, 2860, 1600, 1570, 1485, 1460, 1390, 1320, 1290, 1260, 1240, 1170, 1140, 1120, 1060, 1050, 1040, 1020 cm$^{-1}$; MS m/z 304 (M$^+$), 192, 175, 112, 94, 83, 71, 57.

1-Bromo-2-fluoro-4-decyloxybenzene (20). Quantities: compound 18 (15.00 g, 0.079 mol) in acetone (215 ml), 1-bromodecane (17.39 g, 0.079 mol) in acetone (20 ml), potassium carbonate (33.16 g, 0.204 mol). The experimental procedure was as described for the preparation of compound 4. This crude product was purified by column chromatography (silica gel/dichloromethane) to give a colourless liquid.

Yield 22.36 g (65%); bp 160°–162° C. at 1.2 mmHg; $^1$H NMR (CDCl$_3$) d 0.90 (3H, t), 1.30 (14H, m), 1.80 (2H, quint), 3.95 (2H, t), 6.65 (2H, m), 7.40 (1H, t); IR (KCl) vmax 2920, 2860, 1600, 1580, 1485, 1460, 1380, 1320, 1290, 1260, 1165, 1140, 1020 cm$^{-1}$; MS m/z 330 (M$^+$), 203, 192, 175, 111, 94, 83, 69.

1-Bromo-2-fluoro-4-dodecyloxybenzene (21). Quantities: compound 18 (15.00 g, 0.078 mol) in acetone (215 ml), 1-bromodecane (19.56 g, 0.079 mol) in acetone (20 ml), potassium carbonate (33.16 g, 0.204 mol). The experimental procedure was as described for the preparation of compound 4. This crude product was purified by column chromatography (silica gel/dichloromethane) to give a colourless liquid.

Yield 24.77 g (89%); bp 180°–182° C. at 1.2 mmHg; $^1$H NMR (CDCl$_3$) d 0.85 (3H, t), 1.30 (18H, m), 1.75 (2H, quint), 3.90 (2H, t), 6.65 (2H, m), 7.40 (1H, t); IR (KCl) vmax 2920, 2850, 1600, 1580, 1485, 1460, 1430, 1420, 1380, 1320, 1290, 1260, 1240, 1165, 1140, 1120, 1050, 1015 cm$^{-1}$; MS m/z 360 (M$^+$), 190, 111, 97, 83, 69, 63, 57.

2-Fluoro-4-octyloxyphenylboronic acid (22). Quantities: compound 19 (8.00 g, 0.026 mol) in anhydrous THF (106 ml). n-butyllithium (13 ml. 2.5M in hexane, 0.033 mol), trimethyl borate (5.50 g, 0.053 mol) in anhydrous THF (50 ml). The experimental procedure was as described for the preparation of compound 2.

Crude yield of an off white solid 6.6 g (93%); $^1$H NMR (CDCl$_3$) d 0.90 (3H, t), 1.30 (10H, m), 1.80 (2H, quint), 3.95 (2H, t), 6.70 (2H, m), 7.50 (1H, t), 7.90 (1H, broad s); IR (KCl) vmax 3100–3600, 2920, 2850, 1620, 1560, 1500, 1460, 1430, 1380, 1350, 1290, 1230, 1150, 1120, 1030, 1010 cm$^{-1}$; MS m/z 268 (M$^+$), 156, 138, 128, 112, 83, 75, 71.

2-Fluoro-4-decyloxyphenylboronic acid (23). Quantities: compound 20 (8.28 g, 0.025 mol) in anhydrous THF (100 ml), n-butyllithium (10.5 ml, 2.5M in hexane, 0.026 mol), trimethyl borate (5.20 g, 0.050 mol) in anhydrous THF (20 ml). The experimental procedure was as described for the preparation of compound 2.

Crude yield of an off white solid 7.39 g (100%); $^1$H NMR (CDCl$_3$) d 0.90 (3H, t), 1.30 (14H, m), 1.70 (2H, quint), 4.00 (2H, t), 6.70 (2H, m), 7.50 (1H, t), 7.90 (2H, broad s); IR (KCl) vmax 3100–3700, 2920, 2850, 1610, 1560, 1470, 1430, 1380, 1350, 1290, 1230, 1150, 1120, 1030, 1020, 1010 cm$^{-1}$; MS m/z 296 (M$^+$), 253, 156, 128, 112, 97, 83, 69.

2-Fluoro-4-dodecyloxyphenylboronic acid (24). Quantities: compound 21 (8.00 g, 0.022 mol) in anhydrous THF (92 ml), n-butyllithium (10 ml, 2.5M in hexane, 0.025 mol), trimethyl borate (4.79 g, 0.045 mol) in anhydrous THF (35 ml). The experimental procedure was as described for the preparation of compound 2.

Crude yield of an off white solid 7.69 g (106%); $^1$H NMR (CDCl$_3$) d 0.85 (3H, t), 1.30 (18H, m), 1.70 (2H, quint), 4.00 (2H, t), 6.70 (2H, m), 7.50 (1H, t), 7.85 (2H, broad s); IR (KCl) vmax 3100–3700, 2920, 2850, 1615, 1560, 1465, 1425, 1380, 1345, 1290, 1230, 1145, 1110, 1025, 1005 cm$^{-1}$; MS m/z 324 (M$^+$), 296, 196, 156, 128, 112, 97, 83, 69, 57.

1-Bromo-4-octyloxybenzene (26). A solution of 1-bromooctane (21.05 g, 0.109 mol) in acetone (50 ml) was added dropwise to a stirred refluxing mixture of compound 25 (18.86 g, 0.109 mol) and potassium carbonate (46.00 g, 0.33 mol) in acetone (300 ml). The stirred mixture was heated under reflux for 12 h. The potassium carbonate was filtered off, water was added to the filtrate and the product was extracted into ether (twice). The combined ether extracts were washed with water, 5% sodium hydroxide, water and dried (MgSO$_4$). The solvent was removed in vacuo to yield a colourless liquid. The crude product was purified by column chromatography (silica gel/dichloromethane).

Yield 28.04 g (90%); bp 146°–148° C. at 1.2 mmHg; $^1$H NMR (CDCl$_3$) d 0.90 (3H, t), 1.30 (10H, m), 1.80 (2H, quint), 3.95 (2H, t), 6.75 (2H, d), 7.40 (1H, d); IR (KCl) vmax 2920, 2850, 1590, 1565, 1485, 1460, 1390, 1280, 1240, 1170, 1100, 1070, 1025, 1000 cm$^{-1}$; MS m/z 384 (M$^+$), 174, 157, 145, 113, 93, 83, 76, 57.

1-Bromo-4-nonyloxybenzene (27). Quantities: compound 25 (18.02 g, 0.109 mol) in acetone (300 ml), 1-bromononane (30.10 g, 0.109 mol) in acetone (30 ml), potassium carbonate (46.00 g, 0.33 mol). The experimental procedure was as described for the preparation of compound 26. The crude product was purified by column chromatography (silica gel/dichloromethane) to give a colourless liquid.

Yield 20.88 g (64%); bp 148°–150° C. at 1.7 mmHg; $^1$H NMR (CDCl$_3$) d 0.90 (3H, t), 1.30 (12H, m), 1.75 (2H, quint), 3.95 (2H, t), 6.75 (2H, d), 7.40 (1H, d); IR (KCl) vmax 2920, 2860, 1590, 1570, 1485, 1460, 1390, 1280, 1240, 1170, 1100, 1070, 1030, 1000 cm$^{-1}$; MS m/z 298 (M$^+$), 215, 172, 101, 85, 73, 65.

1-Bromo-4-decyloxybenzene (28). Quantities: compound 25 (18.86 g, 0.109 mol) in acetone (300 ml), 1-bromodecane (18.01 g. 0.109 mol) in acetone (30 ml), potassium carbonate (46.00 g, 0.33 mol). The experimental procedure was as described for the preparation of compound 26. The crude product was purified by column chromatography (silica gel/dichloromethane) to give a white solid.

Yield 23.61 g (68%); mp 21.5°–22° C.; $^1$H NMR (CDCl$_3$) d 0.90 (3H, t), 1.30 (14H, m), 1.80 (2H, quint), 3.90 (2H, t), 6.75 (2H, d), 7.40 (1H, d): IR (KCl) vmax 2920, 2850, 1585, 1570, 1485, 1460, 1385, 1370, 1295, 1280, 1240, 1170, 1120, 1100, 1070, 1020, 1045, 1000 cm$^{-1}$. MS m/z 314 (M$^+$), 172, 134, 93, 84, 75, 69.

1-Bromo-4-undecyloxybenzene (29). Quantities: compound 25(18.86 g, 0.109 mol) in acetone (300 ml), 1-bromoundecane (25.60 g, 0.109 mol) in acetone (50 ml), potassium carbonate (46.00 g, 0.33 mol). The experimental procedure was as described for the preparation of compound 26. The crude product was purified by column chromatography (silica gel/dichloromethane) to give a white solid.

Yield 29.44 g (83%); mp 23.5°–24.5° C.; $^1$H NMR (CDCl$_3$) d 0.90 (3H, t), 1.30 (16H, m), 1.80(2H, quint), 3.90 (2H, t), 6.75 (2H, d), 7.40 (1H, d), IR (KCl) vmax 2920, 2850, 1590, 1570, 1485, 1465, 1280, 1240, 1170, 1070, 1000 cm$^{-1}$, MS m/z 328 (M$^+$), 172, 155, 97, 85, 76, 65, 55.

1-Bromo-4-dodecyloxybenzene (30). Quantities: compound 25 (18.86 g, 0.109 mol) in acetone (300 ml), 1-bromodecane (27.17 g, 0.109 mol) in acetone (30 ml), potassium carbonate (46.00 g, 0.33 mol). The experimental procedure was as described for the preparation of compound 26. The crude product was purified by column chromatography (silica gel/dichloromethane) to give a white solid.

Yield 33.74 g (91%); mp 32°–33° C.; $^1$H NMR (CDCl$_3$) d 0.85 (3H, t), 1.30 (18H, m), 1.75 (2H, quint), 3.90 (2H, t), 6.75 (2H, d), 7.40 (2H, d); IR (KCl) vmax 2920, 2850, 1585, 1570, 1485, 1460, 1380, 1370, 1295, 1280, 1240, 1170, 1130, 1110, 1100, 1070, 1035, 1045, 1000 cm$^{-1}$; MS m/z 342 (M$^+$), 172, 157, 143, 93, 83, 69, 65, 55.

1-Bromo-4-tetradecyloxybenzene (31). Quantities: compound 25 (18.86 g, 0.109 mol) in acetone (300 ml), 1-bromotetradecane (30.10 g, 0.109 mol) in acetone (30 ml), potassium carbonate (46.00 g, 0.33 mol). The experimental procedure was as described for the preparation of compound 26. The crude product was purified by column chromatography (silica gel/dichloromethane) to give a white solid.

Yield 37.14 g (92%); mp 41.5°–42.5° C.; $^1$H NMR (CDCl$_3$) d 0.85 (3H, t), 1.30 (22H, m), 1.80 (2H, quint), 3.90 (2H, t), 6.75 (2H, d), 7.40 (2H, d); IR (KCl) vmax 2920, 2840, 1590, 1570, 1490, 1470, 1390, 1280, 1240, 1170, 1070, 1040, 1000 cm$^{-1}$; MS m/z 370 (M$^+$), 174, 157, 143, 85, 65, 57, 41.

4-Octyloxyphenylboronic acid (33). n-Butyllithium (23 ml, 2.5M in hexane, 0.058 mol) was added dropwise to a stirred, cooled (−78° C.) solution of compound 26 (15.00 g, 0.053 mol) in dry THF (168 ml) under dry nitrogen. The reaction mixture was maintained under these conditions for 2.5 h and then a solution of trimethyl borate (10.98 g, 0.106 mol) in dry THF (50 ml) was added dropwise at −78° C. The reaction mixture was allowed to warm to room temperature overnight and then stirred for 1 h with 10% hydrochloric acid (120 ml). The product was extracted into ether (twice), and the combined ethereal extracts were washed with water and dried (MgSO$_4$). The solvent was removed in vacuo to yield an off white solid.

Crude yield 11.56 g (88%); $^1$H NMR (CDCl$_3$) d 0.90 (3H, t), 1.40 (10H, m), 1.80 (2H, quint), 4.00 (2H, t), 7.00 (2H, m), 8.10 (2H, m), no obvious OH absorption; IR (KCl) vmax 3100–3400, 2920, 2860, 1600, 1565, 1510, 1460, 1410, 1350, 1305, 1290, 1245, 1170, 1115, 1070, 1030, 1010 cm$^{-1}$; MS m/z 248 (M$^+$), 222, 186, 110, 94, 81, 71, 65.

4-Nonyloxyphenylboronic acid (34). Quantities: compound 27 (14.70 g, 0.066 mol) in anhydrous THF (140 ml), n-butyllithium (30 ml, 2.5M in hexane, 0.075 mol), trimethyl borate (13.72 g, 0.132 mol) in anhydrous THF (50 ml). The experimental procedure was as described for the preparation of compound 33.

Crude yield of an off white solid 12.28 g (71%); $^1$H NMR (CDCl$_3$) d 0.90 (3H, t), 1.30 (12H, m), 1.80 (2H, quint), 4.00 (2H, t), 6.95 (2H, m), 8.15 (2H, m), no obvious OH absorption; IR (KCl) vmax 3100–3300, 2960, 2850, 1600, 1560, 1510, 1460, 1410, 1365, 1350, 1290, 1240, 1170, 1110, 1040, 1010 cm$^{-1}$; MS m/z 276, 248, 110, 94, 77, 71, 56, 43.

4-Decyloxyphenylboronic acid (35). Quantities: compound 28 (9.39 g, 0.03 mol) in anhydrous THF (100 ml), n-butyllithium (12.1 ml, 2.5M in hexane, 0.03 mol), trimethyl borate (6.24 g, 0.066 mol) in anhydrous THF (20 ml). The experimental procedure was as described for the preparation of compound 33.

Crude yield of an off white solid 7.54 g (89%); $^1$H NMR (CDCl$_3$) d 0.90 (3H, t), 1.30 (14H, m), 1.70 (2H, quint), 4.00 (2H, t), 6.85 (2H, m), 7.75 (2H, m), no obvious OH absorption. IR (KCl) vmax 3100–3700, 2920, 2850, 1600, 1560, 1510, 1480, 1460, 1410, 1365, 1350, 1300, 1290, 1270, 1240, 1170, 1110, 1040 cm$^{-1}$; MS m/z 360, 284, 234, 211, 111, 107, 94, 83, 77.

4-Undecyloxyphenylboronic acid (36). Quantities: compound 29 (15.36 g, 0.047 mol) in anhydrous THF (200 ml), n-butyllithium (26 ml, 2.5M in hexane, 0.065 mol), trimethyl borate (9.79 g, 0.094 mol) in anhydrous THF (26 ml). The experimental procedure was as described for the preparation of compound 33.

Crude yield of an off white solid 14.30 g (104%); $^1$H NMR (CDCl$_3$) d 0.90 (3H, t), 1.30 (10H, m), 1.80 (2H, quint), 3.95 (2H, t), 7.00 (2H, m), 8.10 (2H, m), no obvious OH absorption. IR (KCl) vmax 3100–3600, 2920, 2850, 1600, 1560, 1510, 1460, 1410, 1370, 1350, 1300, 1240, 1170, 1110 cm$^{-1}$; MS m/z 264, 248, 135, 110, 94, 85, 69, 58.

4-Dodecyloxyphenylboronic acid (37). Quantities: compound 30 (15.00 g, 0.047 mol) in anhydrous THF (150 ml), n-butyllithium (20 ml, 2.5M in hexane, 0.050 mol), trimethyl borate (9.79 g, 0.094 mol) in anhydrous THF (50 ml). The experimental procedure was as described for the preparation of compound 33.

Crude yield of an off white solid 13.05 g (91%); $^1$H NMR (CDCl$_3$) d 0.90 (3H, t), 1.30 (18H, m), 1.80 (2H, quint), 4.00 (2H, t), 7.00 (2H, m), 8.00 (2H, m), no obvious OH absorption; IR (KCl) vmax 3100–3600, 2920, 2850, 1600, 1565, 1510, 1470, 1410, 1370, 1350, 1305, 1250, 1180, 1110, 1080, 1050 cm$^{-1}$; MS m/z 304, 1278, 262, 110, 94, 81, 69.

4-Tetradecyloxyphenylboronic acid (32). Magnesium turnings (1.84 g, 0.08 mol) were added to a stirred solution, at room temperature under dry nitrogen, of compound 31 (15.00 g, 0.040 mol) in dry THF (150 ml) containing 1,2-dibromoethane (2 drops). The reaction mixture was maintained under these conditions for 1 h and then heated under reflux for 1 h. The reaction mixture was cooled to −78° C. and a solution of trimethyl borate (5.75 g, 0.08 mol) in dry THF (50 ml) was added dropwise. The reaction mixture was allowed to warm to room temperature overnight and then stirred for 1 h with 10% hydrochloric acid (100 ml). The product was extracted into ether (twice), and the combined ethereal extracts were washed with water and dried (MgSO$_4$). The solvent was removed in vacuo to yield a white solid.

Crude yield 11.87 g (89%); $^1$H NMR (CDCl$_3$) d 0.90 (3H, t), 1.30 (22H, m), 1.80 (2H, quint), 4.00 (2H, t), 6.95 (2H, m), 8.15 (2H, m), no obvious OH absorption, IR (KCl) vmax 3100–3600, 2960, 2850, 1600, 1560, 1515, 1470, 1410, 1375, 1350, 1280, 1240, 1170, 1110, 1040, 1020, 1010 cm$^{-1}$; MS m/z 513, 290, 125, 110, 93, 76, 69, 64.

4'-Bromo-4-dodecyloxybiphenyl (39). A solution of 1-bromodecane (10.02 g, 0.040 mol) in acetone (30 ml) was added dropwise to a stirred refluxing mixture of compound 38 (10.00 g, 0.040 mol) and potassium carbonate (29.00 g, 0.137 mol) in acetone (150 ml). The stirred mixture was heated under reflux for 12 h. The potassium carbonate was filtered off, water was added to the filtrate and the product was extracted into ether (twice). The combined ether extracts were washed with water, sodium hydroxide (200 ml, 5%), water and dried (MgSO$_4$). The solvent was removed in vacuo to yield a colourless liquid. This crude product was purified by column chromatography (silica gel/dichloromethane) to give a white solid.

Yield 9.89 g (59%); mp 111°–112° C.; $^1$H NMR (CDCl$_3$) d 0.85 (3H, t), 1.30 (18H, m), 1.75 (2H, quint), 4.00 (2H, t), 6.95 (2H, t), 7.50 (6H, m); IR (KCl) vmax 2920, 2850, 1600, 1580, 1510, 1470, 1410, 1390, 1305, 1285, 1245, 1195, 1145, 1125, 1095, 1025, 1000 cm$^{-1}$; MS m/z 416 (M$^+$), 248, 219, 169, 153, 139, 115.

4'-Dodecyl-4-phenylboronic acid (40). Quantities: compound 39 (6.00 g, 0.0144 mol) in anhydrous THF (500 ml), n-butyllithium (8 ml, 2.5M in hexane, 0.020 mol), trimethyl borate (4.00 g, 0.0385 mol) in anhydrous THF (20 ml). The experimental procedure was as described for the preparation of compound 55.

Crude yield of an off white solid 6.14 g (112%); $^1$H NMR (CDCl$_3$) d 0.85 (3H, t), 1.30 (18H, m), 1.70 (2H, quint), 4.00 (2H, t), 6.50 (1H, broad s), 7.00 (2H, d), 7.55 (4H, m), 7.85 (2H, d), 8.00 (1H, broad s); IR (KCl) vmax 3000–3600, 2910, 2840, 1600, 1575, 1525, 1470, 1390, 1310, 1280, 1250, 1210, 1180, 1125, 1025, 1000 cm$^{-1}$; MS m/z 380 (M$^+$), 447, 338, 183, 170, 152, 141, 127, 110, 97, 89, 77, 69, 57.

1-(4-Bromophenyl)cyclohex-1-ene (42). n-Butyllithium (42 ml, 2.5M in hexane, 0.105 mol) was added dropwise to a stirred, cooled (−78° C.) solution of compound 41 (24.81 g, 0.105 mol) in dry THF (180 ml) under dry nitrogen. The reaction mixture was maintained under these conditions for 40 min and then a solution of cyclohexanone (9.82 g, 0.100 mol) in dry THF (20 ml) was added dropwise at −78° C. The reaction mixture was allowed to warm to room temperature overnight and then washed with a saturated solution of ammonium chloride (300 ml), the product was extracted into ether (twice). The combined ethereal extracts were washed with water and dried ($MgSO_4$). The solvent was removed in vacuo to yield an orange liquid. To this crude intermediate, toluene-4-sulfonic acid (2.40 g, 0.0126 mol) in toluene (150 ml) was added and the reaction mixture was heated in a Dean-Stark apparatus for 1.5 h. The resulting solution was allowed to cool and washed with a saturated solution of sodium hydrogen carbonate (150 ml) and the product was extracted into ether (twice). The combined ethereal extracts were washed with water and dried ($MgSO_4$). The solvent was removed in vacuo to yield an off white solid which was recrystallized from petroleum spirit (40°–60° C.).

Yield 22.36 g (90%); mp 67°–68° C.; $^1H$ NMR ($CDCl_3$) d 1.70 (2H, m), 1.80 (2H, m), 2.20 (2H, m), 2.40 (2H, t), 6.10 (1H, t), 7.25 (2H, d), 7.45 (2H, d); IR (KCl) vmax 2920, 2860, 2830, 1630, 1480, 1450, 1430, 1395, 1350, 1270, 1240, 1135, 1105, 1080, 1000 $cm^{-1}$; MS m/z 236 ($M^+$), 221, 157, 141, 115, 101, 90, 76, 70, 63.

1-(4-Bromophenyl)-4-propylcyclohex-1-ene (46). n-Butyllithiun (42 ml, 2.5M in hexane. 0.105 mol) was added dropwise to a stirred, cooled (−78° C.) solution of compound 41 (24.80 g, 0.1 mol) in dry THF (180 ml) under dry nitrogen. The reaction mixture was maintained under these conditions for 2.5 h and then a solution of 4-propylcyclohex-1-one (3.92 g, 0.1 mol) in dry THF (20 ml) was added dropwise at −78° C. The reaction mixture was allowed to warm to room temperature overnight and then washed with a saturated solution of ammonium chloride (300 ml). The product was extracted into ether (twice) and the combined ethereal extracts were washed with water and dried ($MgSO_4$). The solvent was removed in vacuo to yield an orange liquid. To this crude intermediate toluene-4-sulfonic acid (2.40 g, 0.0126 mol) in toluene (150 ml) was added and the reaction mixture was heated in a Dean-Stark apparatus for 2 h. The resulting solution was allowed to cool and washed with a saturated solution of sodium hydrogen carbonate (150 ml) and the product was extracted into ether (twice). The combined ethereal extracts were washed with water and dried ($MgSO_4$). The solvent was removed in vacuo to yield an off white solid which was recrystallized from petroleum spirit (40°–60° C.).

Yield 18.91 g (68%): mp 61.5°–62.5° C.; $^1H$ NMR ($CDCl_3$) d 0.90 (3H, t), 1.30 (5H, m), 1.60 (1H, m), 1.75 (2H, m), 2.40 (3H, t), 5.95 (1H, m), 7.25 (2H, d), 7.40 (2H, d); IR (KCl) vmax 2940, 2920, 2880, 2860, 2830, 1630, 1480, 1460, 1450, 1430, 1395, 1370, 1135, 1100, 1070, 1000 $cm^{-1}$; MS m/z 278 ($M^+$), 249, 235, 221, 208, 198, 182, 169, 155, 141, 129, 115, 102, 91, 77, 63, 51.

1-(4-Bromo-2,3-difluorophenyl)cyclohex-1-ene (43). n-Butyllithium (68 ml, 2.5M in hexane, 0.170 mol) was added dropwise to a stirred, cooled (−78° C.) solution of compound 1 (17.5 g, 0.154 mol) in dry THF (280 ml) under dry nitrogen. The reaction mixture was maintained under these conditions for 2.5 h and then a solution of cyclohexanone (14.72 g, 0.154 mol) in dry THF (40 ml) was added dropwise at −78° C. The reaction mixture was allowed to warm to room temperature overnight and then washed with a saturated solution of ammonium chloride (600 ml). The product was extracted into ether (twice) and the combined etheral extracts were washed with water and dried ($MgSO_4$). The solvent was removed in vacuo to yield an orange liquid. This crude intermediate was dissolved in toluene (300 ml) and p-toluene sulphonic acid (5.20 g, 0.0273 mol) was added to the solution. This reaction mixture was refluxed in a Dean Stark apparatus for 1.5 h. The resulting solution was allowed to cool and washed with a saturated solution of sodium hydrogen carbonate (300 ml) and the product was extracted into ether (twice). The combined ethereal extracts were washed with water and dried ($MgSO_4$). The solvent was removed in vacuo to yield a colourless liquid which was purified by column chromatography (silica gel/dichloromethane).

Yield 17.6 g (59%); bp 84°–86° C. at 0.9 mmHg; $^1H$ NMR ($CDCl_3$) d 1.70 (4H, m), 2.20 (2H, m), 2.40 (2H, t), 5.95 (1H, t), 6.95 (3H, m); IR (KCl) vmax 2950, 2850, 1620, 1585, 1485, 1470, 1440, 1385, 1330, 1260, 1250, 1220, 1160, 1085, 1065, 1040, 1030 $cm^{-1}$; MS m/z 194 ($M^+$), 179, 165, 151, 146, 140, 133, 127, 119, 115, 107, 101, 94, 88, 67, 51.

1-(4-Bromo-2-fluorophenyl)cyclohex-1-ene (45). n-Butyllithium (16 ml, 2.5M in hexane, 0.040 mol) was added dropwise to a stirred, cooled (−78° C.) solution of compound 44 (12.00 g, 0.040 mol) in dry THF (80 ml) under dry nitrogen. The reaction mixture was maintained under these conditions for 1.5 h and then a solution of cyclohexanone (3.92 g, 0.040 mol) in dry THF (20 ml) was added dropwise at −78° C. The reaction mixture was allowed to warm to room temperature overnight and then washed with a saturated solution of ammonium chloride (115 ml). The product was extracted into ether (twice) and the combined etheral extracts were washed with water and dried ($MgSO_4$). The solvent was removed in vacuo to yield an orange liquid. This crude intermediate was dissolved in toluene (1100 ml) and p-toluene sulphonic acid (1.00 g, 0.0053 mol) was added to the solution. This reaction mixture was refluxed in a Dean Stark apparatus for 3 h. The resulting solution was allowed to cool and washed with a saturated solution of sodium hydrogen carbonate (60 ml) and the product was extracted into ether (twice). The combined ethereal extracts were washed with water and dried ($MgSO_4$). The solvent was removed in vacuo to yield the crude product which was purified by column chromatography (silica gel/dichloromethane) to give a colourless liquid.

Yield 9.48 g (93%); bp 106°–108° C. at 1.7 mmHg; $^1H$ NMR ($CDCl_3$) d 1.70 (4H, m), 2.20 (2H, m), 2.40 (2H, t), 5.95 (1H, t), 2.20 (3H, m); IR (KCl) vmax 2920, 2860, 2830, 1630, 1595, 1555, 1480, 1445, 1430, 1400, 1270, 1240, 1205, 1135, 1120, 1000 $cm^{-1}$; MS m/z 254 ($M^+$), 239, 226, 213, 200, 175, 160, 147, 133, 127, 119, 109, 99, 94, 87, 79, 73, 67.

trans-1R,2S-(+)-1-(4-Bromo-2-fluorophenyl)cyclohexan-2-ol (51). Quantities: boron trifluoride diethyl etherate (13 ml, 0.0916 mol), R-alpine boramide (20.15 g, 0.0483 mol) in anhydrous THF (50 ml), compound 45 (21.00 g, 0.077 mol), aqueous sodium hydroxide (36.5 ml, 10%) followed by aqueous hydrogen peroxide (78 ml, 12%). The experimental procedure was as described for the preparation of compound 57. The crude product was purified by column chromatography (silica gel/dichloromethane) to give a white solid.

Yield 11.50 g (55%); mp 64.5°–65.5° C.; $[a]_D$+17.36° (0.029 g/ml, 27° C.); $^1H$ NMR ($CDCl_3$) d 1.4–1.6 (5H, m), 1.8 (3H, m) 2.20 (1H, m), 2.80 (1H, m), 3.70 (1H, m), 7.25 (3H, m); IR (KCl vmax 3100–3600, 2915, 1700, 1600, 1570, 1480, 1445, 1405, 1260, 1210, 1130, 1060 $cm^{-1}$; MS m/z 272 ($M^+$), 254, 228, 215, 202, 189, 175, 160, 147, 134, 121, 109, 98, 82, 75, 71, 66, 62, 56.

trans-1R,2S-(+)-1-(4-Bromo-2-fluorophenyl)-2-methoxycyclohexane (54). Quantities: compound 51 (5.00 g, 0.0196 mol), sodium hydride (1.18 g, 80%, 0.039 mol) in DMF (20 ml), methyl iodide (2.79 g, 0.0196 mol) in DMF (20 ml). The experimental procedure was as described for the preparation of compound 58. The crude product was purified by column chromatography (silica gel/ dichloromethane) to give a colourless liquid.

Yield 3.56 g (47%); bp (short path) 186°–187° C. at 0.45 mmHg; $[a]_D$+14.8° (0.154 g/ml, 23° C.); $^1$H NMR (CDCl$_3$) d 1.2–1.6 (4H, m), 1.7–1.9 (3H, m), 2.30 (1H, m), 2.85 (1H, m), 3.15 (3H, s), 3.30 (1H, m), 7.20 (3H, m); IR (KCl) vmax 2915, 2850, 2820, 1600, 1570, 1480, 1445, 1405, 1375, 1355, 1340, 1325, 1260, 1230, 1210, 1170, 1130, 1100, 1070, 1040, 1010 cm$^{-1}$; MS m/z 286 (M$^+$), 256, 226, 202, 187, 175, 160, 147, 133, 120, 101, 81, 71, 58, 42.

trans-(1S,2R)-(+)-2-(4-Bromophenyl)cyclohexan-1-ol (49). Boron trifluoride diethyl etherate (5.0 ml, 0.0352 mol) was added dropwise over 2 min to a solution of (R)-Alpine-Boramine (7.70 g, 0.0185 mol) in anhydrous THF (20 ml) under dry nitrogen. This mixture was stirred under dry nitrogen for 2 h at room temperature. The mixture was then cooled down to 0° C. and a solution of compound 42 (7.5 g, 0.0315 mol) in anhydrous THF (20 ml) and the mixture allowed to heat up to room temperature overnight. The solution was stirred for a further 5 days at room temperature. Any solid present was removed by filtration. The filtrate was heated to reflux and aqueous sodium hydroxide (13.5 ml, 10%) followed by aqueous hydrogen peroxide (11.25 ml, 30%) was added. This mixture was refluxed for 1 h and then allowed to cool to room temperature. The solution was then saturated with potassium carbonate and the product was extracted into ether (twice). The combined ethereal extracts were washed with water and dried (MgSO$_4$). The solvent was removed in vacuo to yield a colourless liquid. This crude product was purified by column chromatography (silica gel/dichloromethane) to give a white solid.

Yield 5.20 g (65%); mp 106°–107° C.; $[a]_D$+8.5° (0.045 g/ml, 27° C.); $^1$H NMR (CDCl$_3$) d 1.45 (5H, m), 1.80 (3H, m), 2.20 (1H, m), 2.40 (1H, q), 3.60 (1H, m), 7.20 (2H, d), 7.45 (2H, d); IR (KCl) vmax 3000–3500, 2920, 2880, 2860, 2830, 1485, 1440, 1430, 1405, 1340, 1300, 1240, 1200, 1130, 1120, 1095, 1065, 1055, 1005 cm$^{-1}$; MS m/z 254 (M$^+$), 236, 210, 195, 182, 169, 157, 142, 129, 115, 103, 98, 91, 85, 77, 71, 63, 57, 51.

trans-(1R,2S)-(+)-2-(4-Bromophenyl)-4-propylcyclohexan-2-ol (50). Quantities: boron trifluoride diethyl etherate (6.4 ml, 0.0451 mol), (R)-Alpine-Boramine (10.26 g, 0.0246 mol), compound 46 (11.67 g, 0.042 mol), aqueous sodium hydroxide (18 ml, 10%) followed by aqueous hydrogen peroxide (15 ml, 30%). The experimental procedure was as described for the preparation of compound 49. The crude product was purified by column chromatography (silica gel/dichloromethane) to give a white solid.

Yield of cis/trans mixture 6.77 g (55%); mp 39°–40° C.; $[a]_D$+6.4° (0.037 g/ml, 27° C.); $^1$H NMR (CDCl$_3$) d 0.9–2.2 (15H, m), 2.40 (1H, m), 3.60–3.80 (1H, m), 7.20 (2H, m), 7.45 (2H, d); IR (KCl) vmax 3100–3600, 2950, 2920, 2880, 1485, 1440, 1405, 1375, 1130, 1100, 1070, 1050, 1005 cm$^{-1}$; MS m/z 296 (M$^+$), 280, 252, 237, 223, 209, 195, 183, 171, 156, 141, 128, 115, 98, 90, 83, 76, 66, 62.

trans-(1R,2S)-(+)-1-(4-Bromophenyl)-2-methoxycyclohexane (52). Compound 49 (15.00 g, 0.0585 mol) was added to a solution of sodium hydride (3.60 g, 80%, 0.117 mol) in DMF (40 ml) under dry nitrogen. This mixture was stirred for 15 min and a solution of methyl iodide (8.46 g, 0.0585 mol) in DMF (30 ml) was added. The reaction mixture was stirred for 12 h at room temperature and water (20 ml) was added slowly. The solution was extracted (twice) with ether. The combined ethereal extracts were washed with water and dried (MgSO$_4$). The solvent was removed in vacuo to yield a colourless liquid. This crude product was purified by column chromatography (silica gel/dichloromethane) to give a white solid.

Yield 10.55 g (67%); mp 38.5°–39.5° C.; $[a]_D$+8.9° (0.024 g/ml, 27° C.); $^1$H NMR (CDCl$_3$) d 1.45 (4H, m), 1.80 (3H, m), 2.20 (1H, m), 2.50 (1H, q), 3.10 (3H, s), 3.20 (1H, m), 7.10 (2H, d), 7.40 (2H, d); IR (KCl) vmax 2915, 2860, 2820, 1485, 1445, 1405, 1360, 1340, 1300, 1250, 1190, 1115, 1100, 1075, 1005 cm$^{-1}$; MS m/z 270 (M$^+$), 238, 210, 197, 184, 171, 157, 142, 129, 115, 98, 89, 77, 71, 67, 63, 58, 51.

trans-(1R,2S)-(+)-1-(4-Bromophenyl)-2-methoxy-4-propylcyclohexane (53). Quantities: compound 50 (6.05 g, 0.0204 mol), sodium hydride (1.23 g, 80%, 0.041 mol) in DMF (20 ml), methyl iodide (2.94 g, 0.0204 mol) in DMF (20 ml). The experimental procedure was as described for the preparation of compound 52. The crude product was purified by column chromatography (silica gel/ dichloromethane) to give a white solid.

Yield of cis/trans mixture 3.85 g (61%); mp 39°–40° C.; $[a]_D$+12.0° (0.038 g/ml, 26° C.); $^1$H NMR (CDCl$_3$) d 0.9–2.2 (14H, m), 2.50 (1H, m), 3.1 (3H, s), 3.60–3.80 (1H, m), 7.10 (2H, m), 7.40 (2H, m): IR (KCl) vmax 2950, 2920, 2885, 2820, 1485, 1450, 1405, 1380, 1190, 1130, 1100, 1075, 1050, 1010 cm$^{-1}$; MS m/z 310 (M$^+$), 267, 235, 209, 182, 171, 156, 141, 129, 113, 103, 97, 89, 77, 71, 55.

4-[trans-(1R,2S)-Methoxycyclohexyl]phenylboronic acid (55). n-Butyllithium (17 ml, 2.5M in hexane, 0.0425 mol) was added dropwise to a stirred. cooled (−78° C.) solution of compound 52 (10.00 g, 0.037 mol) in dry THF (150 ml) under dry nitrogen. The reaction mixture was maintained under these conditions for 2.5 h and then a solution of trimethyl borate (7.96 g, 0.0759 mol) in anhydrous THF (50 ml) was added dropwise at −78° C. The reaction mixture was allowed to warm to room temperature overnight and then stirred for 1 h with 10% hydrochloric acid (120 ml). The product was extracted into ether (twice), and the combined etheral extracts were washed with water and dried (MgSO$_4$). The solvent was removed in vacuo to yield an off white solid.

Crude yield of an off white solid 9.22 g (107%); $^1$H NMR (CDCl$_3$) d 1.45–2.0 (7H, m), 2.25 (1H, m), 2.60 (1H, m), 3.10 (3H, s), 3.40 (1H, m), 7.40 (2H, d), 8.20 (2H, d), no obvious OH absorption; IR (KCl) vmax 3000–3700, 2920, 2850, 2820, 1610, 1510, 1450, 1410, 1370, 1335, 1295, 1265, 1185, 1150, 1130, 1100, 1095, 1020, 1000 cm$^{-1}$; MS m/z 234 (M$^+$), 284, 274, 246, 206, 190, 174, 158, 143, 130, 117, 99, 91, 81, 77, 71, 67.

trans-1S,2R-(+)-1-Methoxy-2-(4'-bromobiphen-4-yl)cyclohexane (56). Bromoiodobenzene (7.64 g, 0.027 mol) in 1,2-dimethoxyethane (25 ml) was added to an aqueous solution of sodium bicarbonate (67.5 ml, 2M) under dry nitrogen. Tetrakis(triphenylphosphine)palladium(0) (1.50 g, 1.20 mmol) followed by compound 55 (8.00 g, 0.0342 mol) in 1,2-dimethoxyethane (25 ml) was added. The reaction mixture was refluxed for 12 h, allowed to cool to room temperature and extracted (three times) with ether. The combined etheral extracts were washed with water and dried (MgSO$_4$). The solvent was removed in vacuo to yield a dark brown solid. This crude product was purified by column chromatography (silica gel/dichloromethane) and recrystallised from ethanol to yield a white solid.

Yield 5.94 g (64%); mp 94°–96° C.; $[a]_D$+7.42° (0.0258 g/ml, 25° C.); $^1$H NMR (CDCl$_3$) d 1.45 (5H, m), 1.80 (3H, m), 2.25 (1H, m), 2.55 (1H, q), 3.15 (3H, s), 3.30 (1H, m), 7.20 (2H, m), 7.50 (6H, m); IR (KCl) vmax 2920, 2850, 2820, 1480, 1445, 1390, 1355, 1305, 1250, 1190, 1130, 1110, 1095, 1075, 1040, 1000 cm$^{-1}$; MS m/z 334 (M$^+$), 285, 258, 247, 204, 191, 178, 165, 152, 129, 115, 99, 89, 82, 71.

trans -1R,2S-(+)-1-(2,3-Difluorophenyl)-cyclohexan-2-ol (57). Boron trifluoride diethyl etherate (6.0 ml, 0.0423 mol) was added dropwise over 2 min to a solution of (R)-Alpine boramide™ (9.43 g, 0.0226 mol) in anhydrous THF (20 ml) under dry nitrogen. This mixture was stirred under dry nitrogen for 2 h at room temperature. The mixture was then cooled down to 0° C. and a solution of compound 43 (7.5 g, 0.0386 mol) in anhydrous THF (20 ml) was added. This mixture was then allowed to heat up to room temperature overnight and was stirred for a further 5 days. Any solid then present was removed by filtration. The filtrate was heated to reflux and aqueous sodium hydroxide (16 ml, 10%) followed by aqueous hydrogen peroxide (13.5 ml, 30%) was added. This mixture was refluxed for 1 h and then allowed to cool to room temperature. The solution was saturated with potassium carbonate and the product was extracted into ether (twice). The combined etheral extracts were washed with water and dried (MgSO$_4$). The solvent was removed in vacuo to yield a colourless liquid. This crude product was purified by column chromatography (silica gel/ dichloromethane) to give a white solid.

Yield 5.48 g (67%); bp 108°–110° C. at 2.4 mmHg; [a]$_D$+9.0° (0.024 g/ml, 26° C.); $^1$H NMR (CDCl$_3$) d 1.4–1.6 (5H, m), 1.8 (3H, m) 2.20 (1H, m), 2.80 (1H, m), 3.75 (1H, m), 7.00 (3H, m); IR(KCl) vmax 3100–3600, 2915, 2855, 1700, 1620, 1590, 1480, 1445, 1405, 1345, 1310, 1280, 1235, 1195, 1160, 1070, 1055, 1020 cm$^{-1}$; MS m/z 212 (M$^+$), 194, 179, 174, 169, 156, 153, 146, 140, 133, 127, 119, 113, 107, 101, 98, 95, 91, 75, 67, 63.

trans-1R,2S-(+)-1-(2,3-Difluorophenyl)-2-methoxycyclohexane (58). Compound 57 (5.00 g, 0.0236 mol) was added to a solution of sodium hydride (1.42 g, 80%, 0.047 mol) in DMF (15 ml) under dry nitrogen. This mixture was stirred for 15 min and a solution of methyl iodide (3.40 g, 0.02365 mol) in DMF (15 ml) was added. The reaction mixture was stirred for 12 h at room temperature and water (20 ml) was added slowly. The solution was extracted (twice) with ether. The combined etheral extracts were washed with water and dried (MgSO$_4$). The solvent was removed in vacuo to yield a colourless liquid. The crude product was purified by column chromatography (silica gel/dichloromethane) to give a colourless liquid.

Yield 3.16 g (59%); bp (short path) 140°–142° C. at 1.0 mmHg: [a]$_D$+20.4° (0.032 g/ml, 25° C.); $^1$H NMR (CDCl$_3$) d 1.2–1.6 (4H, m), 1.7–2.0 (3H, m) 2.25 (1H, m), 2.90 (1H, m). 3.18 (3H, s), 3.35 (1H, m), 7.00 (3H, m); IR (KCl) vmax 2915, 2855, 2820, 1620, 1590, 1480, 1445, 1375, 1355, 1345, 1320, 1275, 1255, 1235, 1210, 1190, 1160, 1120, 1100, 1060, 1045, 1020 cm$^{-1}$; MS m/z 226 (M$^+$), 194, 166, 127, 71, 67, 58, 45.

2,3-Difluoro-4-[trans-(1R,2S)-methoxycyclohexyl] phenylboronic acid (59). Quantities: compound 58 (4.5 g, 0.02 mol) in anhydrous THF (100 ml), n-butyllithium (9 ml, 2.5M in hexane, 0.0225 mol), trimethyl borate (4.30 g, 0.041 mol) in anhydrous THF (30 ml). The experimental procedure was as described for the preparation of compound 2.

Crude yield of a yellow clear liquid 5.71 g (106%); [a]$_D$+16.6° (0.020 g/ml, 25° C.); $^1$H NMR (CDCl$_3$) d 0.8–1.8 (7H, m), 2.20 (1H, m), 2.80 (1H, m), 3.10 (3H, s), 3.35 (1H, m), 7.20 (2H, m), 8.25 (2H, broad s); IR (KCl) vmax 3100–3600, 2915, 2855, 2820, 1625, 1495, 1450, 1380, 1345, 1345, 1290, 1270, 1250, 1235, 1220, 1190, 1160, 1140, 1120, 1100, 1070, 1020 cm$^{-1}$; MS m/z 242 (M$^+$), 226, 194, 166, 140, 127, 98, 85, 77, 71, 67, 63.

trans-1S,2R-(+)-1-Methoxy-2-(2,3-difluoro-4'-octyloxybiphen-4-yl)cyclohexane (60). Quantities: compound 59 (1.00 g, 0.0037 mol) in 1,2-dimethoxyethane (3 ml), aqueous solution of sodium bicarbonate (7 ml, 2M), tetrakis(triphenylphosphine)palladium(0) (0.15 g, 0.12 mmol), compound 26 (0.8 g, 0.0028 mol) in 1,2-dimethoxyethane (2.5 ml). The experimental procedure was as described for the preparation of compound 75. The crude product was purified by column chromatography (silica gel/dichloromethane) and recrystallised from ethanol to yield a white solid.

Yield 0.36 g (30%); mp 35°–36° C.; [a]$_D$+2.4° (0.0196 g/ml, 27° C.); $^1$H NMR (CDCl$_3$) d 0.9 (3H, t), 1.2–1.6 (14H, m), 1.7–1.9 (5H, m), 2.30 (1H, m), 2.90 (1H, m), 3.20 (3H, s), 3.40 (1H, m), 4.00 (2H, t), 6.95–7.15 (4H, m), 7.50 (2H, m); IR (KCl) vmax 2925, 2860, 1610, 1520, 1490, 1460, 1410, 1370, 1310, 1285, 1250, 1190, 1180, 1125, 1100, 1045, 1025 cm$^{-1}$; MS m/z 430 (M$^+$), 318, 286, 271, 258, 238, 232, 219, 201, 190, 177, 159, 143, 125, 111, 97, 84, 71.

trans-1S,2R-(+)-1-Methoxy-2-(4'-decyloxy-2,3-difluorobiphen-4-yl)cyclohexane (61). Quantities: compound 59 (1.00 g, 0.0037 mol) in 1,2-dimethoxyethane (3 ml), aqueous solution of sodium bicarbonate (7 ml, 2M), tetrakis(triphenylphosphine)palladium(0) (0.20 g, 0.16 mmol), compound 28 (0.87 g, 0.0028 mol) in 1,2-dimethoxyethane (2.5 ml). The experimental procedure was as described for the preparation of compound 75. The crude product was purified by column chromatography (silica gel/dichloromethane) and recrystallised from ethanol to yield a white solid.

Yield 0.52 g (41%). mp 39°–40° C.; [a]$_D$+2.5° (0.0191 g/ml, 26° C.); $^1$H NMR (CDCl$_3$) d 0.9 (3H, t), 1.2–1.6 (22H, m), 1.7–1.9 (5H, m), 2.30 (1H, m), 2.90 (1H, m), 3.20 (3H, s), 3.40 (1H, m), 4.00 (2H, t), 6.95–7.15 (4H, m), 7.45 (2H, m); IR (KCl) vmax 2920, 2850, 1610, 1580, 1520, 1490, 1460, 1410, 1395, 1375, 1355, 1310, 1285, 1250, 1190, 1180, 1125, 1100, 1030, 1000 cm$^{-1}$; MS m/z 486 (M$^+$), 318, 286, 258, 232, 219, 201, 190, 138, 121, 106, 93, 78, 71, 65, 55, 45; CHN analysis requires: C, 75.40%; H, 9.42%; found: C, %; H, %.

trans-1S,2R-(+)-1-Methoxy-2-(2,3-difluoro-4'-dodecyloxybiphen-4-yl)cyclohexane (62). Quantities: compound 59 (1.20 g, 0.0049 mol) in 1,2-dimethoxyethane (7 ml), aqueous solution sodium bicarbonate (7 ml, 2M), tetrakis(triphenylphosphine)palladium(0) (0.30 g, 0.24 mmol), compound 30 (0.95 g, 0.0028 mol) in 1,2-dimethoxyethane (2.5 ml). The experimental procedure was as described for the preparation of compound 75. The crude product was purified by column chromatography (silica gel/dichloromethane) and recrystallised from ethanol to yield a white solid.

Yield 1.02 g (75%); mp 42°–43° C.; [a]$_D$+18.1° (0.0264 g/ml, 27° C.); $^1$H NMR (CDCl$_3$) d 0.9 (3H, t), 1.2–1.6 (18H, m), 1.7–1.9 (5H, m), 2.30 (1H, m), 2.90 (1H, m), 3.20 (3H, s), 3.40 (1H, m), 4.00 (2H, t), 6.95–7.15 (4H, m), 7.45 (2H, m); IR (KCl) vmax 2920, 2850, 1610, 1580, 1520, 1490, 1460, 1410, 1370, 1360, 1310, 1285, 1250, 1190, 1180, 1125, 1100, 1050, 1025 cm$^{-1}$; MS m/z 458 (M$^+$), 318, 286, 245, 232, 219, 214, 201, 197, 188, 177, 169, 159, 152, 143, 123, 111, 97, 91, 83, 71: CHN analysis requires: C, 76.25%; H, 9.14%; found: C, 76.25%; H, 9.14%.

trans-(1S,2R)-(+)-1-Methoxy-2-(4'-octyloxybiphen-4-yl) cyclohexane (63). Compound 52 (0.76 g, 0.0028 mol) in 1,2-dimethoxyethane (2.5 ml) was added to an aqueous solution of sodium carbonate (7 ml, 2M) under dry nitrogen. Tetrakis(triphenylphosphine)palladium(0) (0.15 g, 0.12 mmol) followed by compound 33 (0.94 g, 0.0037 mol) in 1,2-dimethoxyethane (2.5 ml) was added. The reaction mixture was refluxed for 12 h. allowed to cool to room temperature and extracted (three times) with ether. The combined ethereal extracts were washed with water and dried (MgSO$_4$). The solvent was removed in vacuo to yield a dark brown solid. This crude product was purified by column chromatography (silica gel/dichloromethane) and recrystallized from ethanol to yield a white solid.

Yield 0.51 g (46%); mp 61°–62° C.; [a]$_D$+5.7° (0.0293 g/ml, 26.5° C.); $^1$H NMR (CDCl$_3$) d 0.9 (3H, t), 1.2–1.6 (14H, m), 1.7–1.9 (5H, m), 2.30 (1H, m), 2.85 (1H, m), 3.15 (3H, s), 3.30 (1H, m), 4.00 (2H, t), 6.95 (2H, d), 7.25 (2H, d), 7.5 (4H, m); IR (KCl) vmax 2915, 2850, 1600, 1580, 1495, 1465, 1450, 1390, 1280, 1250, 1200, 1190, 1180, 1130, 1105, 1095, 1010 cm$^{-1}$; MS m/z 394 (M$^+$), 378, 309, 282, 250, 235, 221, 209, 196, 183, 165, 152, 141, 128, 115, 107, 97, 91, 81, 71; CHN analysis requires: C, 82.18%; H, 9.71%; found: C, 82.09%; H, 9.62%.

trans-(1S,2R)-(+)-1-Methoxy-2-(4'-nonyloxybiphenyl-4-yl)cyclohexane (64). Quantities: compound 52 (0.75 g, 0.0028 mol) in 1,2-dimethoxyethane (3 ml), aqueous solution of sodium carbonate (7 ml, 2M), tetrakis (triphenylphosphine)palladium(0) (0.25 g, 0.21 mmol), compound 34 (1.11 g, 0.0044 mol) in 1,2-dimethoxyethane (5 ml). The experimental procedure was as described for the preparation of compound 63. The crude product was purified by column chromatography (silica gel/dichloromethane) and recrystallized from ethanol to yield a white solid.

Yield 0.36 g (31%); mp 64°–65° C.; [a]$_D$+9.8° (0.0195 g/ml, 25.5° C.); $^1$H NMR CDCl$_3$) d 0.9 (3H, t), 1.2–1.6 (16H, m), 1.7–1.9 (5H, m), 2.30 (1H, m), 2.60 (1H, m), 3.15 (3H, s), 3.30 (1H, m), 4.00 (2H, t), 6.95 (2H, d), 7.25 (2H, d), 7.5 (4H, m); IR (KCl) vmax 2915, 2850, 1600, 1580, 1495, 1470, 1455, 1390, 1355, 1300, 1280, 1250, 1210, 1180, 1130, 1100, 1040, 1020, 1010, 1000 cm$^{-1}$; MS m/z 408 (M$^+$), 282, 265, 250, 235, 222, 209, 196, 183, 165, 152, 141, 128, 107, 91, 81, 71, 55, 45; CHN analysis requires: C, 82.30%; H, 9.87%; found: C, 82.17%; H, 9.75%.

trans-(1R,2S)-(+)-1-(4'-Decyloxybiphenyl-4-yl)-2-methoxycyclohexane (65). Quantities: compound 52 (0.76 g, 0.0028 mol) in 1,2-dimethoxyethane (2.5 ml), aqueous solution of sodium carbonate (7 ml, 2M). tetrakis (triphenylphosphine)palladium(0) (0.14 g, 0.11 mmol), compound 35 (1.08 g, 0.0035 mol) in 1,2-dimethoxyethane (2.5 ml). The experimental procedure was as described for the preparation of compound 63. The crude product was purified by column chromatography (silica gel/ dichloromethane) and recrystallized from ethanol to yield a white solid.

Yield 0.50 g (42%); 53°–54° C.; [a]$_D$+8.4° (0.0186 g/ml. 26.5° C.); $^1$H NMR (CDCl$_3$) d 0.9 (3H, t), 1.2–1.6 (18H, m), 1.7–1.9 (5H, m), 2.30 (1H, m), 2.55 (1H, m), 3.15 (3H, s), 3.30 (1H, m), 4.00 (2H, t), 6.95 (2H, d), 7.25 (2H, d), 7.5 (4H, m); IR (KCl) vmax 2920, 2850, 1600, 1485, 1465, 1450, 1385, 1280, 1250, 1200, 1190, 1180, 1130, 1105, 1095, 1070 cm$^{-1}$; MS m/z 422 (M$^+$), 400, 323, 282, 250, 235, 222, 209, 196, 183, 166, 152, 138, 128, 121, 115, 107, 91, 83, 71, 55, 43; CHN analysis requires: C, 82.41%; H, 10.02%; found: C, 82.39%; H, 9.95%.

trans-(1S,2R)-(+)-1-Methoxy-2-(4'-undecyloxybiphenyl-4-yl)cyclohexane (66). Quantities: compound 52 (0.75 g, 0.0028 mol) in 1,2-dimethoxyethane (3 ml), aqueous solution of sodium carbonate (7 ml, 2M), tetrakis (triphenylphosphine)palladium(0) (0.25 g, 0.21 mmol), compound 36 (1.22 g, 0.0046 mol) in 1,2-dimethoxyethane (5 ml). The experimental procedure was as described for the preparation of compound 63. The crude product was purified by column chromatography (silica gel/dichloromethane) and recrystallized from ethanol to yield a white solid.

Yield 0.78 g (64%); mp 68°–69° C.; [a]$_D$+6.0° (0.0259 g/ml, 25.5° C.); $^1$H NMR (CDCl$_3$) d 0.9 (3H, t), 1.2–1.6 (20H, m), 1.7–1.9 (5H, m), 2.25 (1H, m), 2.55 (1H, m), 3.15 (3H, s), 3.30 (1H, m), 4.00 (2H, t), 6.95 (2H, d), 7.25 (2H, d), 7.5 (4H, m); IR (KCl) vmax 2920, 2850, 1605, 1495, 1470, 1390, 1355, 1305, 1280, 1265, 1250, 1210, 1180, 1105, 1095, 1050, 1030, 1010, 1000 cm$^{-1}$; MS m/z 436 (M$^+$), 406, 295, 283, 250, 235, 221, 209, 196, 183, 165, 152, 141, 128, 121, 115, 101, 91, 83, 71, 58; CHN requires: C, 82.52%; H, 10.15%; found: C, 82.40%; H, 9.98%.

trans-(1R,2S)-(+)-1-(4'-Dodecyloxybiphenyl-4-yl)-2-methoxycyclohexane (67). Quantities: compound 52 (0.76 g, 0.0028 mol) in 1,2-dimethoxyethane (3 ml), aqueous solution of sodium carbonate (7 ml, 2M), tetrakis (triphenylphosphine)palladium(0) (0.15 g, 0.12 mmol), compound 37 (1.12 g, 0.0047 mol) in 1,2-dimethoxyethane (4 ml). The experimental procedure was as described for the preparation of compound 63. The crude product was purified by column chromatography (silica gel/dichloromethane) and recrystallized from ethanol to yield a white solid.

Yield 0.74 g (47%); mp 67°–68° C.; [a]$_D$+8.0° (0.0234 g/ml at 22° C.); $^1$H NMR (CDCl$_3$) d 0.9 (3H, t), 1.2–1.6 (22H, m), 1.7–1.9 (5H, m), 2.30 (1H, m), 2.55 (1H, m), 3.15 (3H, s), 3.30 (1H, m), 4.00 (2H, t), 6.95 (2H, d), 7.25 (2H, d), 7.5 (4H, m); IR (KCl) vmax 2920, 2850, 1605, 1495, 1470, 1450, 1390, 1280, 1250, 1210, 1180, 1130, 1105, 1095, 1040, 1000 cm$^{-1}$; MS m/z 450 (M$^+$), 351, 282, 250, 235, 221, 209, 196, 183, 165, 152, 141, 128, 107, 91, 83, 71, 55, 45; CHN analysis requires: C, 8.61%; H, 10.29%; found: C, 82.58%; H, 10.16%.

trans-(1S,2R)-(+)-1-Methoxy-2-(4'-tetradecyloxybiphenyl-4-yl)cyclohexane (68). Quantities: compound 52 (0.75 g, 0.0028 mol) in 1,2-dimethoxyethane (3 ml), aqueous solution of sodium carbonate (7 ml, 2M), tetrakis(triphenylphosphine)palladium(0) (0.25 g, 0.21 mmol), compound 32 (1.64 g, 0.0051 mol) in 1,2-dimethoxyethane (5 ml). The experimental procedure was as described for the preparation of compound 63. The crude product was purified by column chromatography (silica gel/dichloromethane) and recrystallized from ethanol to yield a white solid.

Yield 0.77 g (56%); mp 73°–74° C.; [a]$_D$+6.3° (0.0187 g/ml, 30° C.); $^1$H NMR (CDCl$_3$) d 0.9 (3H, t), 1.2–1.6 (26H, m), 1.7–1.9 (5H, m), 2.30 (1H, m), 2.55 (1H, m), 3.15 (3H, s), 3.30 (1H, m), 4.00 (2H, t), 6.95 (2H, d), 7.25 (2H, d), 7.5 (4H, m); IR (KCl) vmax 2920, 2850, 1600, 1495, 1465, 1390, 1280, 1250, 1210, 1190, 1180, 1130, 1105, 1095, 1040, 1020, 1000 cm$^{-1}$; MS m/z 478 (M$^+$), 446, 282, 250, 239, 222, 209, 196, 183, 165, 152, 141, 128, 107, 91, 83, 71, 55; CHN analysis requires: C, 82.79%; H, 10.53%; found: C, 82.78%; H, 10.50%.

trans-(1R,2S)-(+)-1-(4'-Dodecyloxybiphenyl-4-yl)-2-methoxy-4-propylcyclohexane (68a). Quantities: compound 53 (1.00 g, 0.0032 mol) in 1,2-dimethoxyethane (5 ml), aqueous solution of sodium carbonate (7 ml, 2M). tetrakis (triphenylphosphine)palladium(0) (0.25 g, 0.20 mmol), compound 37 (1.47 g, 0.0049 mol) in 1,2-dimethoxyethane (5 ml). The experimental procedure was as described for the preparation of compound 63.

The crude product was purified by column chromatography (silica gel/dichloromethane) and recrystallized from ethanol to yield a white solid.

Yield of cis/trans mixture 0.27 g (18%); $[a]_D$+5.7° (0.0208 g/ml at 26° C.); $^1$H NMR (CDCl$_3$) d 0.8–1.0 (6H, t), 1.2–1.6 (25H, m), 1.7–1.9 (5H, m), 2.30 (1H, m), 2.5–2.7 (1H, m), 3.15 (3H, d), 3.3–3.6 (1H, m), 4.00 (2H, t), 6.95 (2H, d), 7.25 (2H, q), 7.5 (4H, m); IR (KCl) vmax 2920, 2850, 1605, 1580, 1495, 1470, 1395, 1275, 1250, 1210, 1180, 1130, 1100, 1080, 1040, 1000 cm$^{-1}$; MS m/z 493 (M$^+$), 378, 352, 325, 263, 235, 223, 209, 196, 183, 165, 152, 141, 121, 113, 97, 91, 83, 71, 55, 45; CHN analysis requires: C, 82.87%; H, 10.64%; found: C, 82.78%; H, 10.60%.

trans-1S,2R-(+)-1-Methoxy-2-(3'-fluoro-4-octyloxybiphen-4-yl)cyclohexane (69). Quantities compound 52 (0.77 g, 0.0028 mol) in 1,2-dimethoxyethane (3 ml), aqueous solution of sodium bicarbonate (7 ml, 2M). tetrakis(triphenylphosphine)palladium(0) (0.20 g, 0.16 mmol), compound 14 (1.00 g, 0.0042 mol) in 1,2-dimethoxyethane (5 ml). The experimental procedure was as described for the preparation of compound 75. The crude product was purified by column chromatography (silica gel/dichloromethane) and recrystallised from ethanol to yield a white solid.

Yield 0.56 g (49%); mp 46°–47° C.; $[a]_D$+5.9° (0.0204 g/ml, 26.5° C.); $^1$H NMR (CDCl$_3$) d 0.9 (3H, t), 1.2–1.6 (14H, m), 1.7–1.9 (5H, m), 2.30 (1H, m), 2.55 (1H, m), 3.15 (3H, s), 3.30 (1H, m), 4.00 (2H, t), 7.00 (1H, t), 7.3 (4H, m), 7.5 (2H, d); IR (KCl) vmax 2915, 2860, 1620, 1580, 1560, 1530, 1500, 1485, 1465, 1400, 1320, 1290, 1275, 1250, 1230, 1190, 1130, 1105, 1095, 1040, 1020, 1000 cm$^{-1}$; MS m/z 412 (M$^+$), 313, 300, 268, 253, 240, 227, 201, 179, 165, 151, 139, 125, 115, 97, 91, 79, 71; CHN analysis requires: C, 78.04%; H, 9.69%. found: C, %; H, %.

trans-1S,2R-(+)-1-Methoxy-2-(4'-decyloxy-3'-fluorobiphen-4-yl)cyclohexane (70). Quantities: compound 52 (0.76 g, 0.0028 mol) in 1,2-dimethoxyethane (2.5 ml), aqueous solution of sodium bicarbonate (7 ml, 2M), tetrakis (triphenylphosphine)palladium(0) (0.14 g, 0.11 mmol), compound 15 (1.04 g, 0.0035 mol) in 1,2-dimethoxyethane (2.5 ml). The experimental procedure was as described for the preparation of compound 75. The crude product was purified by column chromatography (silica gel/dichloromethane) and recrystallised from ethanol to yield a white solid.

Yield 0.40 g (33%); mp 40°–41° C.; $[a]_D$+5.5° (0.0220 g/ml, 26° C.); $^1$H NMR (CDCl$_3$) d 0.9 (3H, t), 1.2–1.6 (18H, m), 1.7–1.9 (5H, m), 2.30 (1H, m), 2.55 (1H, m), 3.15 (3H, s), 3.30 (1H, m), 4.00 (2H, t), 7.00 (1H, t), 7.3 (4H, m), 7.5 (2H, d); IR (KCl) vmax 2920, 2860, 1620, 1580, 1560, 1530, 1500, 1485, 1465, 1400, 1310, 1290, 1275, 1245, 1210, 1190, 1130, 1105, 1095, 1070, 1040, 1020 cm$^{-1}$; MS m/z 440 (M$^+$), 300, 268, 253, 240, 227, 214, 207, 201, 179, 165, 150, 125, 78, 71; CHN analysis requires: C, 78.46%; H, 10.05%; found: C, %; H, %.

trans-1S,2R-(+)-1-Methoxy-2-(4'-dodecyloxy-3'-fluorobiphen-4-yl)cyclohexane (71). Quantities: compound 52 (0.76 g, 0.0028 mol) in 1,2-dimethoxyethane (3 ml), aqueous solution of sodium bicarbonate (7 ml, 2M), tetrakis (triphenylphosphine)palladium(0) (0.15 g, 0.12 mmol), compound 16 (1.22 g, 0.0035 mol) in 1,2-dimethoxyethane (4 ml). The experimental procedure was as described for the preparation of compound 75. The crude product was purified by column chromatography (silica gel/dichloromethane) and recrystallised from ethanol to yield a white solid.

Yield 0.53 g (41%); mp 50°–51° C.; $[a]_D$+7.1° (0.0203 g/ml, 25° C.), $^1$H NMR (CDCl$_3$) d 0.9 (3H, t), 1.2–1.6 (22H, m), 1.7–1.9 (5H, m), 2.30 (1H, m), 2.55 (1H, m), 3.15 (3H, s), 3.30 (1H, m), 4.05 (2H, t), 7.00 (1H, t), 7.3 (4H, m), 7.5 (2H, d); IR (KCl) vmax 2920, 2860, 1615, 1580, 1560, 1530, 1500, 1485, 1465, 1450, 1400, 1310, 1290, 1270, 1260, 1245, 1210, 1190, 1130, 1105, 1095, 1070, 1040, 1020 cm$^{-1}$; MS m/z 469 (M$^+$), 300, 268, 240, 227, 214, 201, 150, 125, 97, 83, 71; CHN analysis requires: C, 79.44%; H, 9.67%; found: C, 79.14%; H, 9.84%.

trans-1S,2R-(+)-1-Methoxy-2-(2-fluoro-4'-octyloxybiphen-4-yl)cyclohexane (72). Quantities: compound 52 (0.76 g, 0.0028 mol) in 1,2-dimethoxyethane (3 ml), aqueous solution of sodium bicarbonate (7 ml, 2M), tetrakis(triphenylphosphine)palladium(0) (0.15 g, 0.12 mmol), compound 22 (0.94 g, 0.0035 mol) in 1,2-dimethoxyethane (3 ml). The experimental procedure was as described for the preparation of compound 75. The crude product was purified by column chromatography (silica gel/dichloromethane) and recrystallised from ethanol to yield a white solid.

Yield 0.55 g (48%); mp 53°–54° C.; $[a]_D$+7.4° (0.0195 g/ml, 26.5° C.); $^1$H NMR (CDCl$_3$) d 0.9 (3H, t), 1.2–1.6 (14H, m), 1.7–1.9 (5H, m), 2.30 (1H, m), 2.55 (1H, m), 3.15 (3H, s), 3.30 (1H, m), 4.00 (2H, t), 6.70 (2H, m), 7.35 (5H, m); IR (KCl) vmax 2915, 2850, 1620, 1570, 1495, 1465, 1405, 1390, 1355, 1310, 1290, 1270, 1230, 1185, 1160, 1115, 1100, 1040, 1000 cm$^{-1}$; MS m/z 412 (M$^+$), 313, 300, 283, 268, 240, 227, 214, 183, 165, 150, 133, 125, 115, 92, 79, 71, 57, 45; CHN analysis requires: C, 78.04%; H, 9.69%; found: C, %; H, %.

trans-1S,2R-(+)-1-Methoxy-2-(4'-decyloxy-2'-fluorobiphen-4-yl)cyclohexane (73). Quantities: compound 52 (0.76 g, 0.0028 mol) in 1,2-dimethoxyethane (2.5 ml), aqueous solution of sodium bicarbonate (7 ml, 2M), tetrakis (triphenylphosphine)palladium(0) (0.15 g, 0.12 mmol), compound 23 (1.05 g 0.0035 mol) in 12-dimethoxyethane (2.5 ml). The experimental procedure was as described for the preparation of compound 75. The crude product was purified by column chromatography (silica gel/dichloromethane) and recrystallised from ethanol to yield a white solid.

Yield 0.50 g (41%): mp 40°–41° C.; $[a]_D$+6.6° (0.0182 g/ml, 26° C.); $^1$H NMR (CDCl$_3$) d 0.9 (3H, t), 1.2–1.6 (18H, m), 1.7–1.9 (5H, m), 2.30 (1H, m), 2.55 (1H, m), 3.15 (3H, s), 3.30 (1H, m), 4.00 (2H, t), 6.70 (2H, m), 7.30–7.50 (5H, m); IR (KCl) vmax 2920, 2850, 1620, 1570, 1520, 1495, 1465, 1405, 1390, 1355, 1315, 1290, 1260, 1230, 1185, 1165, 1125, 1100, 1070, 1050, 1030, 1020, 1005 cm$^{-1}$; MS m/z 440 (M$^+$), 341, 300, 283, 268, 253, 240, 237, 220, 214, 201, 183, 172, 159, 141, 133, 125, 115, 97, 91, 83, 71; CHN analysis requires: C, 78.46%; H, 10.05%; found: C, %; H, %.

trans-1S,2R-(+)-1-Methoxy-2-(4'-dodecyloxy-2'-fluorobiphen-4-yl)cyclohexane (74). Quantities: compound 52 (0.76 g, 0.0028 mol) in 1,2-dimethoxyethane (3 ml), aqueous solution of sodium bicarbonate (7 ml, 2M), tetrakis (triphenylphosphine)palladium(0) (0.15 g, 0.12 mmol), compound 24 (1.13 g, 0.0035 mol) in 1,2-dimethoxyethane (3 ml). The experimental procedure was as described for the preparation of compound 75. The crude product was purified by column chromatography (silica gel/dichloromethane) and recrystallised from ethanol to yield a white solid.

Yield 0.30 g (23%); mp 47°–48° C.; $[a]_D$+8.4° (0.0172 g/ml, 27° C.); $^1$H NMR (CDCl$_3$) d 0.9 (3H, t), 1.2–1.6 (18H, m), 1.70–1.90 (5H, m), 2.30 (1H, m), 2.55 (1H, m), 3.15 (3H, s), 3.30 (1H, m), 3.95 (2H, t), 6.70 (H, m), 7.25–7.50 (5H, m); IR (KCl) vmax 2920, 2850, 1620, 1575, 1520, 1495, 1470, 1405, 1395, 1355, 1315, 1095, 1040, 1000 cm$^{-1}$; MS m/z 446 (M$^+$), 300, 268, 240, 227, 214, 201, 183, 150, 125, 115, 97, 83, 71; CHN analysis requires: C, 78.84%. H, 10.37%; found: C, %; H, %.

trans-1S,2R-(+)-1-Methoxy-2-(2',3'-difluoro-4'-octyloxybiphen-4-yl)cyclohexane (75). Compound 52 (0.77 g, 0.0028 mol) in 1,2-dimethoxyethane (3 ml) was added to an aqueous solution of sodium bicarbonate (7 ml, 2M) under dry nitrogen. Tetrakis(triphenylphosphine)palladium(0) (0.20 g, 0.16 mmol) followed by compound 7 (1.00 g, 0.0035 mol) in 1,2-dimethoxyethane (3 ml) was added. The reaction mixture was refluxed for 12 h, allowed to cool to room temperature and extracted (three times) with ether. The combined etheral extracts were washed with water and dried (MgSO$_4$). The solvent was removed in vacuo to yield a dark brown solid. The crude product was purified by column chromatography (silica gel/dichloromethane) and distilled under reduced pressure to yield a white solid.

Yield 0.92 g (76%); mp 56°–57° C.; [a]$_D$+6.1° (0.0395 g/ml, 27° C.); $^1$H NMR (CDCl$_3$) d 0.9 (3H, t), 1.2–1.6 (14H, m), 1.7–1.9 (5H, m), 2.30 (1H, m), 2.55 (1H, m), 3.15 (3H, s), 3.30 (1H, m), 4.05 (2H, t), 6.80 (1H, m), 7.10 (1H, m), 7.30 (2H, m), 7.45 (2H, m); IR (KCl) vmax 2915, 2850, 1625, 1490, 1465, 1405, 1310, 1295, 1195, 1130, 1095, 1075 cm$^{-1}$; MS m/z 430 (M$^+$), 399, 318, 286, 271, 245, 232, 219, 201, 188, 170, 151, 143, 128, 115, 91, 79, 71, 57, 45; CHN analysis requires: C, 74.82%; H, 9.04%; found: C, %; H, %.

trans-1S,2R-(+)-1-Methoxy-2-(4'-decyloxy-2',3'-difluorobiphen-4-yl)cyclohexane (76). Quantities: compound 52 (0.76 g, 0.0028 mol) in 1,2-dimethoxyethane (2.5 ml), aqueous solution of sodium bicarbonate (7 ml, 2M), tetrakis(triphenylphosphine)palladium(0) (0.14 g, 0.11 mmol), compound 8 (1.10 g, 0.0035 mol) in 1,2-dimethoxyethane (2.5 ml). The experimental procedure was as described for the preparation of compound 75. The crude product was purified by column chromatography (silica gel/dichloromethane) and distilled under reduced pressure to yield a white solid.

Yield 0.87 g (68%); mp 41°–42° C.; [a]$_D$+6.5° (0.0367 g/ml, 26° C.); $^1$H NMR (CDCl$_3$) d 0.9 (3H, t), 1.2–1.6 (18H, m), 1.70–1.95 (5H, m), 2.30 (1H, m), 2.55 (1H, m), 3.15 (3H, s), 3.30 (1H, m), 4.05 (2H, t), 6.80 (1H, m), 7.10 (1H, m), 7.30 (2H, m), 7.45 (2H, m); IR (KCl) vmax 2920, 2850, 1625, 1500, 1465, 1410, 1380, 1310, 1295, 1195, 1130, 1095, 1075 cm$^{-1}$; MS m/z 458 (M$^+$), 318, 286, 271, 258, 245, 232, 219, 201, 190, 177, 159, 146, 136, 128, 115, 91, 83, 71, 55; CHN analysis requires: C, 75.40%; H, 9.42%; found: C, %; H, %.

trans-1S,2R-(+)-1-Methoxy-2-(2',3'-difluoro-4'-dodecyloxybiphen-4-yl)cyclohexane (77). Quantities: compound 52 (0.76 g, 0.0028 mol) in 1,2-dimethoxyethane (3 ml), aqueous solution of sodium bicarbonate (7 ml, 2M), tetrakis(triphenylphosphine)palladium(0) (0.15 g, 0.12 mmol), compound 9 (1.20 g, 0.0035 mol) in 1,2-dimethoxyethane (3 ml). The experimental procedure was as described for the preparation of compound 75. The crude product was purified by column chromatography (silica gel/dichloromethane) and recrystallised from ethanol to yield a white solid.

Yield 0.60 g (44%); mp 39°–40° C.; [a]$_D$+2.3° (0.0205 g/ml, 27° C.); $^1$H NMR (CDCl$_3$) d 0.9 (3H, t), 1.2–1.6 (22H, m), 1.7–1.9 (5H, m), 2.30 (1H, m), 2.55 (1H, m), 3.15 (3H, s), 3.30 (1H, m), 4.05 (2H, t), 6.80 (1H, m), 7.10 (1H, m), 7.30 (2H, m), 7.45 (2H, m); IR (KCl) vmax 2920, 2850, 1625, 1500, 1470, 1410, 1400, 1315, 1295, 1195, 1130, 1095, 1075 cm$^{-1}$; MS m/z 487 (M$^+$), 318, 286, 258, 245, 232, 219, 203, 183, 170, 151, 143, 128, 115, 91, 83, 71; CHN analysis requires: C, 76.54%: H, 9.11%: found: C, 76.14%; H, 9.25%.

trans-1S,2R-(+)-1-Methoxy-2-(4'-dodecyloxy-3-fluorobiphen-4-yl)cyclohexane (81). Quantities: compound 54 (0.81 g, 0.003 mol) in 1,2-dimethoxyethane (3 ml), aqueous solution of sodium bicarbonate (7 ml, 2M), tetrakis(triphenylphosphine)palladium(0) (0.25 g, 0.21 mmol), compound 30 (1.25 g, 0.0053 mol) in 1,2-dimethoxyethane (4 ml). The experimental procedure was as described for the preparation of compound 75. The crude product was purified by column chromatography (silica gel/dichloromethane) and recrystallised from ethanol to yield a white solid.

Yield 0.78 g (56%); mp 58°–59° C.; [a]$_D$+4.7° (0.0202 g/ml at 22° C.); $^1$H NMR (CDCl$_3$) d 0.9 (3H, t), 1.2–1.6 (22H, m), 1.7–1.9 (5H, m), 2.30 (1H, m), 2.85 (1H, m), 3.20 (3H, s), 3.40 (1H, m), 4.00 (2H, t), 6.95 (2H, d), 7.25 (3H, m), 7.5 (2H, d); IR (KCl) vmax 2920, 2850, 1605, 1580, 1555, 1520, 1495, 1470, 1450, 1390, 1350, 1285, 1265, 1245, 1210, 1185, 1170, 1125, 1100, 1095, 1040, 1020 cm$^{-1}$; MS m/z 468 (M$^+$), 369,300, 253, 239, 234, 227, 220, 214, 201, 183, 172, 159, 146, 133, 121, 107, 97, 91, 83, 71; CHN analysis requires: C, 79.44%; H, 9.68%; found: C, 79.29%; H, 9.90%.

trans-1S,2R-(+)-2-(3-Fluoro-4-octyloxybiphen-4-yl) cyclohexane-1-ol (78). Quantities compound 51 (0.83 g, 0.0033 mol) in 1,2-dimethoxyethane (3 ml), aqueous solution of sodium bicarbonate (7 ml, 2M), tetrakis(triphenylphosphine)palladium(0) (0.25 g, 0.20 mmol), compound 26 (1.10 g, 0.0044 mol) in 1,2-dimethoxyethane (10 ml). The experimental procedure was as described for the preparation of compound 75. The crude product was purified by column chromatography (silica gel/dichloromethane) and distilled under reduced pressure to yield a white solid.

Yield 0.39 g (30%); mp 80.5°–81.5° C.; [a]$_D$+3.2° (0.0224 g/ml, 23° C.); $^1$H NMR (CDCl$_3$) d 0.9 (3H, t), 1.2–1.6 (15H, m), 1.7–1.9 (5H, m), 2.20 (1H, m), 2.85 (1H, m), 3.80 (1H, m), 4.00 (2H, t), 6.95 (2H, d), 7.30 (3H, m), 7.50 (2H, d); IR (KCl) vmax 3100–3700, 2920, 2850, 1605, 1580, 1550, 1520, 1495, 1465, 1430, 1395, 1295, 1280, 1235, 1185, 1170, 1135, 1125, 1055, 1000 cm$^{-1}$; MS m/z 398 (M$^+$), 381, 313, 299, 286, 268, 253, 227, 214, 201, 183, 170, 159, 146, 133, 127, 117, 101, 81, 73; CHN analysis requires: C, 77.80%; H, 9.49%: found: C, %; H, %.

trans-1S,2R-(+)-2-(4'-Decyloxy-3-fluorobiphen-4-yl) cyclohexane-1-ol (79). Quantities: compound 51 (0.76 g, 0.003 mol) in 1,2-dimethoxyethane (3 ml), aqueous solution of sodium bicarbonate (7 ml, 2M), tetrakis(triphenylphosphine)palladium(0) (0.25 g, 0.20 mmol), compound 28 (1.08 g, 0.0039 mol) in 1,2-dimethoxyethane (11 ml). The experimental procedure was as described for the preparation of compound 75. The crude product was purified by column chromatography (silica gel/dichloromethane) and distilled under reduced pressure to yield a white solid.

Yield 0.44 g (34%); mp 91°–92° C.; [a]$_D$+14.8° (0.0309 g/ml, 23° C.); $^1$H NMR (CDCl$_3$) d 0.9 (3H, t), 1.2–1.6 (19H, m), 1.7–1.9 (5H, m), 2.20 (1H, m), 2.85 (1H, m), 3.80 (1H, m), 4.00 (2H, t), 6.95 (2H, d), 7.30 (3H, m), 7.50 (2H, d); IR (KCl) vmax 3100–3700, 2920, 2850, 1605, 1580, 1550, 1520, 1495, 1465, 1430, 1395, 1295, 1280, 1250, 1225, 1185, 1170, 1135, 1125, 1055, 1020 cm$^{-1}$; MS m/z 426 (M$^+$), 286, 268, 258, 227, 214, 201, 183, 172, 159, 146, 133, 107, 94, 85, 69, 57, 43; CHN analysis requires: C, 78.26%; H, 9.87%; found: C, %; H, %.

trans-1S,2R-(+)-2-(4'-Dodecyloxy-3-fluorobiphen-4-yl) cyclohexane-1-ol (80). Quantities: compound 51 (0.76 g, 0.003 mol) in 1,2-dimethoxyethane (3 ml), aqueous solution sodium bicarbonate (7 ml, 2M), tetrakis (triphenylphosphine)palladium(0) (0.25 g, 0.20 mmol), compound 30 (1.15 g, 0.0038 mol) in 1,2-dimethoxyethane (16 ml). The experimental procedure was as described for the preparation of compound 75. The crude product was purified by column chromatography (silica gel/ dichloromethane) and recrystallised from ethanol to yield a white solid.

Yield 0.57 g (42%); mp 94°–95° C.; $[a]_D$+11.7° (0.0205 g/ml, 27° C.); $^1$H NMR (CDCl$_3$) d 0.9 (3H, t), 1.2–1.6 (23H, m), 1.7–1.9 (5H, m), 2.15 (1H, m), 2.85 (1H, m), 3.80 (1H, m), 4.00 (2H, t), 6.95 (2H, d), 7.30 (3H, m), 7.50 (2H, d): IR (KCl) vmax 3100–3700, 2920, 2850, 1605, 1580, 1555, 1525, 1495, 1465, 1430, 1395, 1280, 1250, 1225, 1210, 1200, 1185, 1170, 1135, 1125, 1110, 1100, 1080, 1060, 1045, 1035, 1020, 1005 cm$^{-1}$; MS m/z 454 (M$^+$), 286, 267, 240, 227, 214, 201, 183, 171, 133, 97, 83, 69; CHN analysis requires: C, 78.66%; H, 10.21%; found: C, %; H, %.

trans-1S,2R-(+)-2-(4'-Dodecyloxybiphen-4-yl) cyclohexane-1-ol (82). Quantities: compound 49 (0.77 g, 0.003 mol) in 1,2-dimethoxyethane (3 ml), aqueous solution of sodium bicarbonate (7 ml, 2M), tetrakis (triphenylphosphine)palladium(0) (0.25 g, 0.20 mmol), compound 30 (1.15 g, 0.0038 mol) in 1,2-dimethoxyethane (16 ml). The experimental procedure was as described for the preparation of compound 75. The crude product was purified by column chromatography (silica gel/ dichloromethane) and recrystallised from ethanol to yield a white solid.

Yield 0.75 g (57%); mp 90°–91° C.; $[a]_D$+5.8° (0.0247 g/ml, 22° C.); $^1$H NMR (CDCl$_3$) d 0.9 (3H, t), 1.2–1.6 (23H, m), 1.7–1.9 (5H, m), 2.15 (1H, m), 2.50 (1H, m), 3.70 (1H, m), 4.00 (2H, t), 6.95 (2H, d), 7.30 (2H, d), 7.50 (4H, m); IR (KCl) vmax 3100–3700, 2920, 2850, 1605, 1580, 1525, 1495, 1465, 1390, 1280, 1250, 1180, 1130, 1110, 1100, 1060, 1040, 1000 cm$^{-1}$; MS m/z 436 (M$^+$), 420, 351, 268, 221, 209, 196, 183, 165, 153, 141, 128, 107, 97, 77, 69; CHN analysis requires: C, 81.86%; H, 10.88%; found: C, %; H, %.

trans-1S,2R-(+)-2-(4"-dodecyloxyterphen-4-yl) cyclohexane-1-ol (82a). Quantities: compound 49 (1.00 g, 0.00387 mol) in 1,2-dimethoxyethane (5 ml), aqueous solution of sodium bicarbonate (9 ml, 2M), tetrakis (triphenylphosphine)palladium(0) (0.25 g, 0.20 mmol) in 1,2-dimethoxyethane (5 ml), compound 40 (2.00 g, 0.0052 mol) in 1,2-dimethoxyethane (20 ml). The experimental procedure was as described for the preparation of compound 56. The crude product was purified by column chromatography (silica gel/dichloromethane) and recrystallised from ethanol to yield a white solid.

Yield 0.35 g (18%); $^1$H NMR (CDCl$_3$) d 0.9 (3H, t), 1.2–1.6 (21H, m), 1.70–1.95 (5H, m), 2.15 (1H, m), 2.50 (1H, m), 3.70 (1H, m), 4.00 (2H, t), 7.00 (2H, d), 7.35 (1H, m), 7.6 (8H, m); IR (KCl) vmax 3100–3600, 2920, 2850, 1605, 1580, 1490, 1470, 1390, 1285, 1255, 1180, 1115, 1060, 1040, 1030, 1000 cm$^{-1}$; MS m/z 512 (M$^+$), 414, 344, 297, 285, 272, 259, 246, 230, 215, 202, 183, 170, 152, 139, 123, 115, 107, 95, 91, 83, 69; CHN analysis requires: C, %; H, %; found: C, %; H, % trans-1S,2R-(+)-2-(4"-dodecyloxy-3-fluoroterphen-4-yl) cyclohexane-1-ol (82b). Quantities: compound 51 (0.75 g, 0.00275 mol) in 1,2-dimethoxyethane (5 ml), aqueous solution of sodium bicarbonate (7 ml, 2M), tetrakis (triphenylphosphine)palladium(0) (0.20 g, 0.16 mmol) in 1,2-dimethoxyethane (5 ml), compound 40 (1.43 g, 0.0037 mol) in 1,2-dimethoxyethane (13 ml). The experimental procedure was as described for the preparation of compound 56. The crude product was purified by column chromatography (silica gel/dichloromethane) and recrystallised from ethanol to yield a white solid.

Yield 0.87 g (60%); $[a]_D$+4.8° (0.0245 g/ml, 26° C.); $^1$H NMR (CDCl$_3$) d 0.9 (3H, t), 1.2–1.6 (20H, m), 1.70–1.95 (5H, m), 2.30 (1H, m), 2.90 (1H, m), 3.20 (3H, s), 3.45 (1H, m), 4.00 (2H, t), 7.00 (2H, d), 7.35 (3H, m), 7.6 (6H, m); IR (KCl) vmax 2920, 2850, 1600, 1580, 1540, 1510, 1485, 1465, 1390, 1290, 1250, 1230, 1180, 1130, 1105, 1095, 1030, 1010, 1000 cm$^{-1}$; MS m/z 545 (M$^+$), 446, 377, 345, 317, 304, 291, 278, 262, 248, 233, 220, 209, 196, 183, 165, 152, 139, 121, 111, 97, 83, 71; CHN analysis requires: C, %; H, %; found: C, %; H, %.

trans-1S,2R-(+)-1-Methoxy-2-(4'-dodecyloxy-3-fluoroterphen-4-yl)cyclohexane (82c). Quantities: compound 54 (0.75 g, 0.00262 mol) in 1,2-dimethoxyethane (5 ml), aqueous solution of sodium bicarbonate (7 ml, 2M), tetrakis(triphenylphosphine)palladium(0) (0.25 g, 0.20 mmol) in 1,2-dimethoxyethane (5 ml), compound 40 (1.37 g, 0.0036 mol) in 1,2-dimethoxyethane (10 ml). The experimental procedure was as described for the preparation of compound 56. The crude product was purified by column chromatography (silica gel/dichloromethane) and recrystallised from ethanol to yield a white solid.

Yield 0.91 g (64%); $[a]_D$+2.3° (0.0483 g/ml, 26° C.); $^1$H NMR (CDCl$_3$) d 0.9 (3H, t), 1.2–1.6 (21H, m), 1.70–1.95 (5H, m), 2.20 (1H, m), 2.85 (1H, m), 3.80 (1H, m), 4.00 (2H, t), 7.00 (2H, d), 7.35 (3H, m), 7.6 (6H, m); IR (KCl) vmax 3100–3600, 2920, 2850, 1600, 1580, 1550, 1510, 1490, 1465, 1390, 1290, 1255, 1210, 1180, 1130, 1060, 1040, 1000 cm$^{-1}$; MS m/z 530 (M$^+$), 363, 320, 306, 276, 259, 214, 196, 185, 175, 161, 151, 133, 121, 104, 97, 83, 77, 69, 55, 41; CHN analysis requires: C, %; H, %; found: C, %; H, %.

trans-1S,2R-(+)-1-methoxy-2-(4"-octyloxyterphen-4-yl) cyclohexane (83). Quantities: compound 58 (0.86 g, 0.026 mol) in 1,2-dimethoxyethane (3 ml), aqueous solution of sodium bicarbonate (7 ml, 2M), tetrakis (triphenylphosphine)palladium(0) (0.30 g, 0.24 mmol) in 1,2-dimethoxyethane (5 ml), compound 33 (0.85 g, 0.0034 mol) in 1,2-dimethoxyethane (5 ml). The experimental procedure was as described for the preparation of compound 58. The crude product was purified by column chromatography (silica gel/dichloromethane) and recrystallised from ethanol to yield a white solid.

Yield 0.52 g (44%); $[a]_D$+2.7° (0.0222 g/ml, 23° C.); $^1$H NMR (CDCl$_3$) d 0.9 (3H, t), 1.2–1.6 (14H, m), 1.70–1.95 (5H, m), 2.30 (1H, m), 2.60 (1H, m), 3.15 (3H, s), 3.30 (1H, m), 4.00 (2H, t), 6.95 (2H, d), 7.30 (2H, d), 7.6 (8H, m); IR (KCl) vmax 2920, 2850, 1600, 1575, 1490, 1470, 1450, 1390, 1350, 1280, 1250, 1200, 1190, 1175, 1130, 1105, 1095, 1040, 1030, 1000 cm$^{-1}$; MS m/z 470 (M$^+$), 439, 371, 272, 259, 250, 243, 230, 215, 202, 183, 165, 141, 128, 107, 101, 91, 81, 71; CHN analysis requires: C, %; H, %; found: C, %; H, %.

trans-1S,2R-(+)-1-Methoxy-2-(4'-nonyloxyterphen-4-yl) cyclohexane (84). Quantities: compound 58 (0.70 g, 0.0020 mol) in 1,2-dimethoxyethane (3 ml), aqueous solution of sodium bicarbonate (7 ml, 2M), tetrakis (triphenylphosphine)palladium(0) (0.25 g, 0.12 mmol) in 1,2-dimethoxyethane (5 ml), compound 34 (0.81 g, 0.0031 mol) in 1,2-dimethoxyethane (5 ml). The experimental procedure was as described for the preparation of compound 58.

The crude product was purified by column chromatography (silica gel/dichloromethane) and recrystallised from ethanol to yield a white solid.

Yield 0.42 g (43%); $[a]_D$+4.7° (0.0203 g/ml, 25.5° C.); $^1$H NMR (CDCl$_3$) d 0.9 (3H, t), 1.2–1.6 (16H, m), 1.70–1.95 (5H, m), 2.30 (1H, m), 2.60 (1H, m), 3.15 (3H, s), 3.30 (1H, m), 4.00 (2H, t), 6.95 (2H, d), 7.30 (2H, d), 7.6 (8H, m); IR (KCl) vmax 2920, 2850, 1600, 1575, 1490, 1470, 1450, 1390, 1280, 1250, 1190, 1175, 1130, 1105, 1095, 1040, 1030, 1000 cm$^{-1}$; MS m/z 484 (M$^+$), 359, 326, 297, 285, 273, 252, 230, 215, 202, 183, 165, 151, 141, 129, 107, 97, 85, 71; CHN analysis requires: C, %; H, %; found: C, %; H, %.

trans-1S,2R-(+)-1-Methoxy-2-(4"-decyloxyterphen-4-yl)cyclohexane (85). Quantities: compound 58 (0.86 g, 0.0025 mol) in 1,2-dimethoxyethane (3 ml), aqueous solution of sodium bicarbonate (7 ml, 2M), tetrakis (triphenylphosphine)palladium(0) (0.15 g, 0.12 mmol) in 1,2-dimethoxyethane (5 ml), compound 35 (1.00 g, 0.0036 mol) in 1,2-dimethoxyethane (6 ml). The experimental procedure was as described for the preparation of compound 58. The crude product was purified by column chromatography (silica gel/dichloromethane) and recrystallised from ethanol to yield a white solid.

Yield 0.76 g (61%); $[a]_D$+3.7° (0.0196 g/ml, 22° C.); $^1$H NMR (CDCl$_3$) d 0.9 (3H, t), 1.2–1.6 (16H, m), 1.70–1.95 (5H, m), 2.60 (1H, m), 3.15 (3H, s), 3.30 (1H, m), 4.00 (2H, t), 6.95 (2H, d), 7.30 (2H, d), 7.6 (8H, m); IR (KCl) vmax 2920, 2850, 1600, 1575, 1490, 1470, 1390, 1280, 1245, 1190, 1175, 1130, 1105, 1095, 1040, 1030, 1000 cm$^{-1}$; MS m/z 498 (M$^+$), 358, 326, 298, 285, 267, 259, 243, 230, 214, 197, 183, 141, 115, 91, 83, 71, 57, 43; CHN analysis requires: C, %; H, %; found: C, %. H, %.

trans-1S,2R-(+)-1-Methoxy-2-(4'-undecyloxyterphen-4-yl)cyclohexane (86). Quantities compound 58 (0.70 g, 0.0020 mol) in 1,2-dimethoxyethane (3 ml), aqueous solution of sodium bicarbonate (7 ml, 2M), tetrakis (triphenylphosphine)palladium(0) (0.25 g, 0.21 mmol) in 1,2-dimethoxyethane (5 ml), compound 36 (0.89 g, 0.0031 mol) in 1,2-dimethoxyethane (5 ml). The experimental procedure was as described for the preparation of compound 58. The crude product was purified by column chromatography (silica gel/dichloromethane) and recrystallised from ethanol to yield a white solid.

Yield 0.43 g (41%); $[a]_D$+4.2° (0.0227 g/ml, 25.5° C.); $^1$H NMR (CDCl$_3$) d 0.9 (3H, t), 1.2–1.6 (18H, m), 1.70–1.95 (5H, m), 2.30 (1H, m), 2.60 (1H, m), 3.15 (3H, s), 3.35 (1H, m), 4.00 (2H, t), 6.95 (2H, d), 7.30 (2H, d), 7.6 (8H, m); IR (KCl) vmax 2920, 2850, 1600, 1575, 1490, 1470, 1390, 1280, 1245, 1190, 1175, 1130, 1105, 1095, 1040, 1030, 1000 cm$^{-1}$; MS m/z 512 (M$^+$), 482, 359, 325, 297, 286, 273, 259, 239, 226, 215, 202, 183, 155, 141, 128, 115, 91, 83, 71, 58, 43; CHN analysis requires: C, %; H, %; found: C, %; H, %.

trans-1S,2R-(+)-1-Methoxy-2-(4"-dodecyloxyterphen-4-yl)cyclohexane (87). Quantities: compound 58 (0.86 g, 0.0025 mol) in 1,2-dimethoxyethane (3 ml), aqueous solution of sodium bicarbonate (7 ml, 2M), tetrakis (triphenylphosphine)palladium(0) (0.15 g, 0.12 mmol) in 1,2-dimethoxyethane (5 ml), compound 37 (0.96 g, 0.0033 mol) in 1,2-dimethoxyethane (6 ml). The experimental procedure was as described for the preparation of compound 58. The crude product was purified by column chromatography (silica gel/dichloromethane) and recrystallised from ethanol to yield a white solid.

Yield 0.50 g (38%); $[a]_D$+10.5° (0.0183 g/ml, 27.5° C.); $^1$H NMR (CDCl$_3$) d 0.9 (3H, t), 1.2–1.6 (20H, m), 1.70–1.95 (5H, m), 2.30 (1H, m), 2.60 (1H, m), 3.15 (3H, s), 3.30 (1H, m), 4.00 (2H, t), 6.95 (2H, d), 7.30 (2H, d), 7.6 (8H, m);, IR (KCl) vmax 2920, 2850, 1600, 1575, 1490, 1470, 1390, 1280, 1245, 1190, 1175, 1130, 1105, 1095, 1040, 1025, 1000 cm$^{-1}$; MS m/z 526 (M$^+$), 494, 427, 358, 325, 297, 285, 272, 259, 243, 230, 215, 202, 183, 156, 141, 129, 115, 97, 83, 71, 57; CHN analysis requires: C, %; H, %; found: C, %; H, %.

trans-1S,2R-(+)-1-Methoxy-2-(4"-tetradecyloxyterphen-4-yl)cyclohexane (88). Quantities: compound 58 (0.70 g, 0.0020 mol) in 1,2-dimethoxyethane (3 ml), aqueous solution of sodium bicarbonate (7 ml, 2M), tetrakis (triphenylphosphine)palladium(0) (0.25 g, 0.20 mmol) in 1,2-dimethoxyethane (5 ml). compound 32 (1.36 g, 0.0043 mol) in 1,2-dimethoxyethane (6 ml). The experimental procedure was as described for the preparation of compound 58. The crude product was purified by column chromatography (silica gel/dichloromethane) and recrystallised from ethanol to yield a white solid.

Yield 0.63 g (56%); $[a]_D$+4.6° (0.0339 g/ml, 25.5° C.); $^1$H NMR (CDCl$_3$) d 0.9 (3H, t), 1.2–1.6 (26H, m), 1.70–1.95 (5H, m), 2.30 (1H, m), 2.60 (1H, m), 3.15 (3H, s), 3.30 (1H, m), 4.00 (2H, t), 6.95 (2H, d), 7.30 (2H, d), 7.6 (8H, m); IR (KCl) vmax 2920, 2840, 1600, 1580, 1490, 1465, 1390, 1285, 1250, 1190, 1180, 1130, 1105, 1095, 1040, 1025, 1000 cm$^{-1}$; MS m/z 554 (M$^+$), 455, 371, 358, 326, 297, 285, 272, 259, 244, 230, 215, 202, 183, 165, 141, 128, 107, 91, 83, 71; CHN analysis requires: C, %; H, %; found: C, %; H, %.

trans-1S,2R-(+)-1-Methoxy-2-(4'-dodecyloxy-3-fluoroterphen-4-yl)cyclohexane (89). Quantities: compound 58 (0.86 g, 0.0025 mol) in 1,2-dimethoxyethane (3 ml), aqueous solution of sodium bicarbonate (7 ml, 2M), tetrakis (triphenylphosphine)palladium(0) (0.15 g, 0.12 mmol) in 1,2-dimethoxyethane (5 ml), compound 16 (1.09 g, 0.0034 mol) in 1,2-dimethoxyethane (6 ml). The experimental procedure was as described for the preparation of compound 58. The crude product was purified by column chromatography (silica gel/dichloromethane) and recrystallised from ethanol to yield a white solid.

Yield 0.70 g (52%); $[a]_D$+2.2° (0.0221 g/ml, 22° C.); $^1$H NMR (CDCl$_3$) d 0.9 (3H, t), 1.2–1.6 (20H, m), 1.70–1.95 (5H, m), 2.30 (1H, m), 2.60 (1H, m), 3.15 (3H, s), 3.30 (1H, m), 4.00 (2H, t), 7.05 (1H, t), 7.30 (4H, m), 7.6 (6H, m); IR (KCl) vmax 2920, 2850, 1610, 1580, 1530, 1515, 1490, 1460, 1390, 1305, 1295, 1270, 1240, 1190, 1130, 1105, 1095, 1070, 1040, 1000 cm$^{-1}$; MS m/z 544 (M$^+$), 445, 376, 344, 316, 303, 290, 277, 261, 239, 201, 179, 157, 120, 107, 91, 83, 71; CHN analysis requires: C, %; H, %; found: C, %; H, %.

trans-1S,2R-(+)-1-Methoxy-2-(4"-dodecyloxy-2"-fluoroterphen-4-yl)cyclohexane (90). Quantities: compound 58 (0.74 g, 0.00215 mol) in 1,2-dimethoxyethane (3 ml), aqueous solution of sodium bicarbonate (7 ml, 2M), tetrakis (triphenylphosphine)palladium(0) (0.25 g, 0.20 mmol) in 1,2-dimethoxyethane (5 ml), compound 24 (1.10 g, 0.0034 mol) in 1,2-dimethoxyethane (6 ml). The experimental procedure was as described for the preparation of compound 58. The crude product was purified by column chromatography (silica gel/dichloromethane) and recrystallised from ethanol to yield a white solid.

Yield 0.30 g (26%); $[a]_D$+2.9° (0.0253 g/ml, 21° C.); $^1$H NMR (CDCl$_3$) d 0.9 (3H, t), 1.2–1.6 (20H, m), 1.70–1.95 (5H, m), 2.30 (1H, m), 2.60 (1H, m), 3.15 (3H, s), 3.30 (1H, m), 4.00 (2H, t), 6.75 (2H, m), 7.35 (3H, m), 7.6 (6H, m); IR (KCl) vmax 2920, 2850, 1620, 1580, 1490, 1470, 1450, 1395, 1320, 1310, 1290, 1270, 1230, 1190, 1170, 1130, 1105, 1095, 1080, 1060, 1040, 1025, 1000 cm$^{-1}$; MS m/z 544 (M⁺), 445, 376, 315, 303, 290, 277, 262, 248, 214, 197, 183, 165, 152, 128, 115, 91, 83, 71, 57; CHN analysis requires: C, %; H, %; found: C, %; H, %.

trans-1S,2R-(+)-1-Methoxy-2-(2",3"-difluoro-4"-dodecyloxyterphen-4-yl)cyclohexane (91). Quantities: compound 58 (0.86 g, 0.0025 mol) in 1,2-dimethoxyethane (3 ml), aqueous solution of sodium bicarbonate (7 ml, 2M), tetrakis(triphenylphosphine)palladium(0) (0.15 g, 0.12 mmol) in 1,2-dimethoxyethane (10 ml), compound 9 (1.07 g, 0.0032 mol) in 1,2-dimethoxyethane (6 ml). The experimental procedure was as described for the preparation of compound 58. The crude product was purified by column chromatography (silica gel/dichloromethane) and recrystallised from ethanol to yield a white solid.

Yield 0.21 g (15%); $[a]_D$+1.2° (0.0195 g/ml, 27° C.); $^1$H NMR (CDCl$_3$) d 0.9 (3H, t), 1.2–1.6 (20H, m), 1.70–1.95 (5H, m), 2.30 (1H, m), 2.60 (1H, m), 3.15 (3H, s), 3.30 (1H, m), 4.10 (2H, t), 6.80 (1H, m), 7.15 (1H, m), 7.30 (2H, m), 7.6 (6H, m); IR (KCl) vmax 2920, 2850, 1630, 1490, 1465, 1390, 1315, 1295, 1225, 1190, 1130, 1105, 1095, 1070, 1000 cm$^{-1}$; MS m/z 562 (M⁺), 395, 363, 334, 321, 308, 295, 282, 257, 219, 205, 191, 165, 143, 128, 111, 91, 83, 71; CHN analysis requires: C, %, H, %; found: C, %; H, %.

trans-1S,2R-(−)-2-Methyl-cyclohexan-1-ol (92). Boron trifluoride diethyl etherate (14 ml, 0.0987 mol) was added dropwise over 2 min to a solution of (R)-Alpine-Boramine™ (22.86 g, 0.0548 mol) in anhydrous THF (20 ml) under dry nitrogen. This mixture was stirred under dry nitrogen for 2 h at room temperature. The mixture was then cooled down to 0° C. and a solution of methylcyclohex-1-ene (9.00 g, 0.0938 mol) in anhydrous THF (20 ml) and the mixture allowed to heat up to room temperature overnight. The solution was stirred for a further 5 days at room temperature. Any solid present was removed by filtration. The filtrate was heated to reflux and aqueous sodium hydroxide (81.5 ml, 10%) followed by aqueous hydrogen peroxide (168.4 ml, 12%) was added. This mixture was refluxed for 1 h and then allowed to cool to room temperature. The solution was then saturated with potassium carbonate and the product was extracted into ether (twice). The combined ethereal extracts were washed with water and dried (MgSO$_4$). The solvent was removed in vacuo to yield a colourless liquid. This crude product was purified by column chromatography (silica gel/dichloromethane) to give a colourless liquid.

Yield 13.98 g, (65.4%); bp 68°–69° C. at 0.6 mmHg; $[a]_D$−3.36° (0.021 g/ml, 26° C.); $^1$H NMR (CDCl$_3$) d 0.9–1.2 (8H, m), 1.60–2.00 (4H, m), 2.40–2.60 (1H, m), 4.10 (1H, m); IR (KCl) vmax MS m/z 254 (M⁺), 236, 210, 195, 182, 169, 157, 142, 129, 115, 103, 98, 91, 85, 77, 71, 63, 57, 51.

R-(+)-(trans)-4-Bromobenzyloxy-(2-Methyl-cyclohexane) (93). Compound 92 (3.75 g, 0.033 mol) was added to a solution of sodium hydride (1.96 g, 80%, 0.066 mol) in DMF (20 ml) under dry nitrogen. This mixture was stirred for 15 min and a solution of methyl iodide 4-bromobenzyl bromide (8.25 g, 0.033 mol) in DMF (10 ml) was added. The reaction mixture was stirred for 12 h at room temperature and water (20 ml) was added slowly. The solution was extracted (twice) with ether. The combined ethereal extracts were washed with water and dried (MgSO$_4$). The solvent was removed in vacuo to yield a colourless liquid. This crude product was purified by column chromatography (silica gel/dichloromethane) to give a colourless solid.

Yield 6.92 g, (74%); bp 172°–173° C.;

R-(+)-4-Dodecyl-4'-[(trans)-Methylcyclohexyloxymethylene]-biphenyl (94). Compound 93 (0.79 g, 0.0028 mol) in 1,2-dimethoxyethane (3 ml) was added to an aqueous solution of sodium carbonate (7 ml, 2M) under dry nitrogen. Tetrakis(triphenylphosphine) palladium(0) (0.15 g, 0.12 mmol) in 1,2-dimethoxyethane (10 ml) followed by compound 37 (1.08 g, 0.0035 mol) in 1,2-dimethoxyethane (6 ml) was added. The reaction mixture was refluxed for 12 h, allowed to cool to room temperature and extracted (three times) with ether. The combined ethereal extracts were washed with water and dried (MgSO$_4$). The solvent was removed in vacuo to yield a dark brown solid. This crude product was purified by column chromatography (silica gel/dichloromethane) and recrystallized from ethanol to yield a white solid.

Yield 0.67 g (52%); mp 80°–81° C.; $[a]_D$; $^1$H NMR (CDCl$_3$) d 0.9 (3H, t), 1.2–1.6 (20H, m), 1.70–1.95 (5H, m), 2.30 (1H, m), 2.90 (1H, m), 3.20 (3H, s), 3.45 (1H, m), 4.00 (2H, t), 7.00 (2H, d), 7.35 (3H, m), 7.6 (6H, m); IR (KCl) vmax 2920, 2850, 1700, 1600, 1580, 1520, 1495, 1479, 1460, 1390, 1285, 1270, 1250, 1195, 1180, 1160, 1105, 1030, 1015, 1000 cm$^{-1}$; MS m/z 464 (M⁺), 352, 214, 197, 183, 165, 153, 135, 121, 109, 97, 91, 83, 71; CHN analysis requires: C, %; H, %; found: C, %; H, %.

R-(+)-(trans)-4-(2-Methyl-cyclohexane)phenylboronic acid (95). n-Butyllithium (13 ml, 2.5M in hexane, 0.033 mol) was added dropwise to a stirred, cooled (−78° C.) solution of compound 93 (8.00 g, 0.028 mol) in anhydrous THF (100 ml) under dry nitrogen. The reaction mixture was maintained under these conditions for 2.5 h and then a solution of trimethyl borate (5.90 g, 0.057 mol) in anhydrous THF (30 ml) was added dropwise at −78° C. The reaction mixture was allowed to warm to room temperature overnight and then stirred for 1 h with 10% hydrochloric acid (120 ml). The product was extracted into ether (twice), and the combined ethereal extracts were washed with water and dried (MgSO$_4$). The solvent was removed in vacuo to yield an off white solid.

Crude yield of an off white solid 8.14 g (116%);

R-(+)-4-Bromo-4'-[(trans)-Methylcyclohexyloxymethylene]-biphenyl (96). Quantities: bromo-iodobenzene (6.50 g, 0.0225 mol) in 1,2-dimethoxyethane (30 ml), aqueous solution of sodium bicarbonate (56 ml, 2M), tetrakis(triphenylphosphine)palladium (0) (1.60 g, 1.28 mmol), compound 95 (7.00 g, 0.0283 mol) in 1,2-dimethoxyethane (30 ml). The experimental procedure was as described for the preparation of compound 94. The crude product was purified by column chromatography (silica gel/dichloromethane) and recrystallised from ethanol to yield a white solid.

Yield 6.35 g (79%);

R-(+)-4-Octyloxy-4"-[(trans)-Methylcyclohexyloxymethylene]-terphenyl (99). Quantities: compound 96 (0.8 g, 0.00224 mol) in 1,2-dimethoxyethane (5 ml), aqueous solution of sodium bicarbonate (7 ml, 2M), tetrakis(triphenylphosphine) palladium(0) (0.25 g, 0.20 mmol) in 1,2-dimethoxyethane (5 ml), compound 33 (0.83 g, 0.00332 mol) in 1,2-dimethoxyethane (5 ml). The experimental procedure was as described for the preparation of compound 94. The crude product was purified by column chromatography (silica gel/dichloromethane) and recrystallised from ethanol to yield a white solid.

Yield 0.52 g (48%); $[a]_D$+5.7° (0.0209 g/ml, 26° C.); $^1$H NMR (CDCl$_3$) d 0.9 (3H, t), 1.05 (3H, d), 1.2–1.6 (16H, m), 1.70–1.95 (4H, m), 2.30 (1H, m), 2.95 (1H, m), 4.00 (2H, t), 4.60 (2H, m), 7.00 (2H, d), 7.40–7.70 (10H, m); IR (KCl) vmax 2920, 2850, 1600, 1580, 1530, 1510, 1490, 1465, 1390, 1285, 1250, 1200, 1185, 1180, 1095, 1020, 1000 cm$^{-1}$; MS m/z 485 (M$^+$), 372, 274, 259, 247, 230, 225, 202, 189, 178, 165, 152, 130, 121, 107, 97, 91, 77, 69, 55, 43; CHN analysis requires: C, %; H, %; found: C, %; H, %.

R-(+)-4-Nonyloxy-4"-[(trans)-Methylcyclohexyloxymethylene]-terphenyl (100). Quantities: compound 96 (1.00 g, 0.0028 mol) in 1,2-dimethoxyethane (5 ml), aqueous solution of sodium bicarbonate (7 ml, 2M), tetrakis(triphenylphosphine) palladium(0) (0.25 g, 0.20 mmol) in 1,2-dimethoxyethane (5 ml), compound 34 (1.04 g, 0.00441 mol) in 1,2-dimethoxyethane (5 ml). The experimental procedure was as described for the preparation of compound 94. The crude product was purified by column chromatography (silica gel/dichloromethane) and recrystallised from ethanol to yield a white solid.

Yield 0.54 g (39%); [a]$_D$+4.4° (0.0268 g/ml, 26° C.); $^1$H NMR (CDCl$_3$) d 0.9 (3H, t), 1.05 (3H, d), 1.2–1.6 (18H, m), 1.70–1.95 (4H, m), 2.15 (1H, m), 2.95 (1H, m), 4.00 (2H, t), 4.60 (2H, m), 7.00 (2H, d), 7.40–7.70 (10H, m); IR (KCl) vmax 2920, 2850, 1600, 1580, 1530, 1510, 1490, 1465, 1390, 1285, 1250, 1205, 1185, 1180, 1095, 1040, 1020, 1000 cm$^{-1}$; MS m/z 498 (M$^+$), 386, 274, 259, 242, 230, 215, 202, 186, 165, 152, 135, 121, 107, 91, 83, 69, 55, 43; CHN analysis requires: C, %; H, %; found: C, %; H, %.

R-(+)-4-Decyloxy-4"-[(trans)-Methylcyclohexyloxymethylene]-terphenyl (97). Quantities: compound 96 (0.8 g, 0.00224 mol) in 1,2-dimethoxyethane (5 ml), aqueous solution of sodium bicarbonate (7 ml, 2M), tetrakis(triphenylphosphine) palladium(0) (0.25 g, 0.20 mmol) in 1,2-dimethoxyethane (5 ml), compound 35 (0.93 g, 0.00335 mol) in 1,2-dimethoxyethane (5 ml). The experimental procedure was as described for the preparation of compound 94. The crude product was purified by column chromatography (silica gel/dichloromethane) and recrystallised from ethanol to yield a white solid.

Yield 0.45 g (39%); [a]$_D$+10.35° (0.0252 g/ml, 26° C.); $^1$H NMR (CDCl$_3$) d 0.9 (3H, t), 1.05 (3H, d), 1.2–1.6 (20H, m), 1.70–1.95 (4H, m), 2.15 (1H, m), 2.95 (1H, m), 4.00 (2H, t), 4.60 (2H, m), 7.00 (2H, d), 7.40–7.70 (10H, m); IR (KCl) vmax 2920, 2850, 1600, 1580, 1530, 1510, 1490, 1465, 1390, 1370, 1350, 1290, 1250, 1200, 1185, 1180, 1105, 1095, 1050, 1020, 1000 cm$^{-1}$; MS m/z 512 (M$^+$), 467, 400, 274, 259, 242, 230, 215, 202, 186, 165, 155, 121, 107, 97, 91, 83, 69, 55, 45; CHN analysis requires: C, %; H, %; found: C, %; H, %.

R-(+)-4-Undecyloxy-4"-[(trans)-Methylcyclohexyloxymethylene]-terphenyl (101). Quantities: compound 96 (0.94 g, 0.0026 mol) in 1,2-dimethoxyethane (3 ml), aqueous solution of sodium bicarbonate (7 ml, 2M), tetrakis(triphenylphosphine) palladium(0) (0.25 g, 0.20 mmol) in 1,2-dimethoxyethane (3 ml), compound 36 (1.23 g, 0.00421 mol) in 1,2-dimethoxyethane (5 ml). The experimental procedure was as described for the preparation of compound 94. The crude product was purified by column chromatography (silica gel/dichloromethane) and recrystallised from ethanol to yield a white solid.

Yield 0.53 g (39%); [a]$_D$+10.2° (0.0209 g/ml, 33° C.); $^1$H NMR (CDCl$_3$) d 0.9 (3H, t), 1.05 (3H, d), 1.2–1.6 (22H, m), 1.70–1.95 (4H, m), 2.15 (1H, m), 2.95 (1H, m), 4.00 (2H, t), 4.60 (2H, m), 7.00 (2H, d), 7.40–7.70 (10H, m); IR (KCl) vmax 2920, 2840, 1605, 1580, 1530, 1510, 1490, 1465, 1390, 1365, 1350, 1290, 1255, 1200, 1180, 1105, 1095, 1040, 1020, 1010, 1000 cm$^{-1}$; MS m/z 526 (M$^+$), 414, 274, 259, 230, 97, 91, 83, 69, 55; CHN analysis requires: C, %; H, %; found: C, %; H, %.

R-(+)-4-Dodecyloxy-4"-[(trans)-Methylcyclohexyloxymethylene]-terphenyl (98). Quantities: compound 96 (0.70 g, 0.00196 mol) in 1,2-dimethoxyethane (5 ml), aqueous solution of sodium bicarbonate (5 ml, 2M), tetrakis(triphenylphosphine) palladium(0) (0.14 g, 0.11 mmol) in 1,2-dimethoxyethane (3 ml). compound 37 (0.80 g, 0.00294 mol) in 1,2-dimethoxyethane (5 ml). The experimental procedure was as described for the preparation of compound 94. The crude product was purified by column chromatography (silica gel/dichloromethane) and recrystallised from ethanol to yield a white solid.

Yield 0.58 g (48%); [a]$_D$+° (g/ml, °C.); $^1$H NMR (CDCl$_3$) d 0.9 (3H, t), 1.05 (3H, d), 1.2–1.6 (24H, m), 1.70–1.95 (4H, m), 2.15 (1H, m), 2.95 (1H, m), 4.00 (2H, t), 4.60 (2H, m), 7.00 (2H, d), 7.40–7.70 (10H, m); IR (KCl) vmax 2920, 2840, 1605, 1580, 1530, 1510, 1490, 1465, 1390, 1370, 1350, 1290, 1255, 1200, 1180, 1105, 1095, 1040, 1020, 1000 cm$^{-1}$; MS m/z 540 (M$^+$), 428, 258, 247, 230, 215, 202, 165, 155, 120, 97, 83, 69, 57; CHN analysis requires: C, %; H, %; found: C, %; H, %.

R-(+)-4-Tetradecyloxy-4"-[(trans)-Methylcyclohexyloxymethylene]-terphenyl (102). Quantities: compound 96 (1.00 g, 0.0028 mol) in 1,2-dimethoxyethane (3 ml), aqueous solution of sodium bicarbonate (7 ml, 2M), tetrakis(triphenylphosphine) palladium(0) (0.39 g, 0.31 mmol) in 1,2-dimethoxyethane (3 ml), compound 32 (1.40 g, 0.00419 mol) in 1,2-dimethoxyethane (5 ml). The experimental procedure was as described for the preparation of compound 94. The crude product was purified by column chromatography (silica gel/dichloromethane) and recrystallised from ethanol to yield a white solid.

Yield 0.46 g (29%); [a]$_D$+19.4° (0.0183 g/ml, 33° C.); $^1$H NMR (CDCl$_3$) d 0.9 (3H, t), 1.05 (3H, d), 1.2–1.6 (28H, m), 1.70–1.95 (4H, m), 2.15 (1H, m), 2.95 (1H, m), 4.00 (2H, t), 4.60 (2H, m), 7.00 (2H, d), 7.40–7.70 (10H, m); IR (KCl) vmax 2920, 2840, 1605, 1580, 1530, 1510, 1490, 1465, 1390, 1365, 1350, 1290, 1250, 1200, 1175, 1105, 1085, 1045, 1020, 1005 cm$^{-1}$; MS m/z 568 (M$^+$), 455, 274, 259, 242, 230, 215, 202, 165, 152, 129, 115, 97, 83, 69, 55; CHN analysis requires: C, %; H, %; found: C, %; H, %.

R-(+)-3-Fluoro-4-dodecyloxy-4"-[(trans)-Methylcyclohexyloxymethylene]-terphenyl (103). Quantities: compound 96 (0.8 g, 0.00224 mol) in 1,2-dimethoxyethane (7 ml), aqueous solution of sodium bicarbonate (7 ml, 2M), tetrakis(triphenylphosphine) palladium(0) (0.25 g, 0.20 mmol) in 1,2-dimethoxyethane (5 ml), compound 16 (1.09 g, 0.00337 mol) in 1,2-dimethoxyethane (10 ml). The experimental procedure was as described for the preparation of compound 94. The crude product was purified by column chromatography (silica gel/dichloromethane) and recrystallised from ethanol to yield a white solid.

Yield 0.29 g (23%); [a]$_D$+3.2° (0.022 g/ml, 26° C.); $^1$H NMR (CDCl$_3$) d 0.9 (3H, t), 1.05 (3H, d), 1.2–1.6 (24H, m), 1.70–1.95 (4H, m), 2.15 (1H, m), 2.95 (1H, m), 4.00 (2H, t), 4.60 (2H, m), 7.00 (1H, t), 7.30–7.70 (10H, m); IR (KCl) vmax 2920, 2840, 1610, 1575, 1530, 1515, 1490, 1465, 1390, 1305, 1270, 1245, 1200, 1185, 1130, 1095, 1040, 1020, 1000 cm$^{-1}$; MS m/z 558 (M$^+$), 446, 391, 292, 277, 248, 165, 152, 115, 97, 91, 83, 77, 69; CHN analysis requires: C, %; H, %; found: C, %; H, %.

R-(+)-2-Fluoro-4-dodecyloxy-4"-[(trans)-Methylcyclohexyloxymethylene]-terphenyl (104). Quantities: compound 96 (0.8 g, 0.00224 mol) in 1,2-dimethoxyethane (7 ml), aqueous solution of sodium bicarbonate (7 ml, 2M), tetrakis(triphenylphosphine) palladium(0) (0.25 g, 0.20 mmol) in 1,2-dimethoxyethane (5 ml), compound 24 (1.09 g, 0.00337 mol) in 1,2-dimethoxyethane (10 ml). The experimental procedure was as described for the preparation of compound 94. The crude product was purified by column chromatography (silica gel/dichloromethane) and recrystallised from ethanol to yield a white solid.

Yield 0.10 g (8%); [a]$_D$+2.9° (0.022 g/ml, 26° C.); $^1$H NMR (CDCl$_3$) d 0.9 (3H, t), 1.05 (3H, d), 1.2–1.6 (24H, m), 1.70–1.95 (4H, m), 2.15 (1H, m), 2.95 (1H, m), 4.00 (2H, t), 4.60 (2H, m), 6.75 (1H, t), 7.30–7.70 (10H, m); IR (KCl) vmax 2920, 2840, 1620, 1575, 1490, 1465, 1395, 1330, 1305, 1285, 1265, 1230, 1200, 1170, 1130, 1095, 1080, 1040, 1020, 1000 cm$^{-1}$; MS m/z 558 (M$^+$), 446, 391, 292, 277, 265, 248, 167, 152, 139, 128, 112, 97, 85, 69; CHN analysis requires: C, %; H, %; found: C, %; H, %.

R-(+)-2,3-Difluoro-4-dodecyloxy-4"-[(trans)-Methylcyclohexyloxymethylene]-terphenyl (105). Quantities: compound 96 (0.8 g, 0.00224 mol) in 1,2-dimethoxyethane (7 ml), aqueous solution of sodium bicarbonate (7 ml, 2M), tetrakis(triphenylphosphine) palladium(0) (0.25 g, 0.20 mmol) in 1,2-dimethoxyethane (5 ml), compound 9 (1.15 g, 0.00337 mol) in 1,2-dimethoxyethane (10 ml). The experimental procedure was as described for the preparation of compound 94. The crude product was purified by column chromatography (silica gel/dichloromethane) and recrystallised from ethanol to yield a white solid.

Yield 0.11 g (9%); [a]$_D$+° (0.0 g/ml, °C.); $^1$H NMR (CDCl$_3$) d 0.9 (3H, t), 1.05 (3H, d), 1.2–1.6 (24H, m), 1.70–1.95 (4H, m), 2.15 (1H, m), 2.95 (1H, m), 4.00 (2H, t), 4.60 (2H, m), 6.8 (1H, m), 7.15 (1H, m), 7.40–7.70 (8H, m); IR (KCl) vmax 2920, 2850, 1630, 1510, 1490, 1465, 1390, 1305, 1290, 1250, 1220, 1190, 1105, 1080, 1060, 1020, 1000 cm$^{-1}$; MS m/z 558 (M$^+$), 446, 391, 292, 277, 265, 248, 167, 152, 139, 128, 112, 97, 85, 69; CHN analysis requires: C, %; H, %; found: C, %; H, %.

Compounds of formula I may be mixed with a wide range of hosts, for example smectic hosts to form a useful liquid crystal composition. Such compositions can have a range of PS values. Compounds of formula I may be mixed with one or more of the types of hosts VIII–XIII. These different types of hosts may be mixed together to which the compound of general formula I may also be added.

Typical hosts include:

The compounds described in PCT/GB86/00040, eg of formula VIII

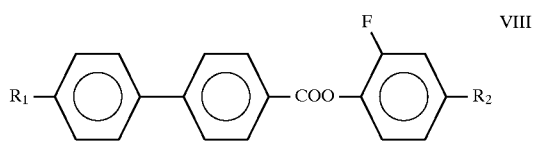

where R$_1$ and R$_2$ are independently C$_3$–C$_{12}$ alkyl or alkoxy.

The fluoro-terphenyls described in EPA 84304894.3 and GBA 8725928, eg of formula IX

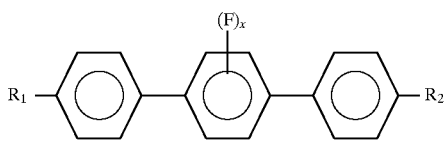

where R$_1$ and R$_2$ are independently C$_3$–C$_{12}$ alkyl or alkoxy, x is 1 and F may be on any of the available substitution positions on the phenyl ring specified.

The difluoro-terphenyls described in GBA 8905422.5, eg of formula X

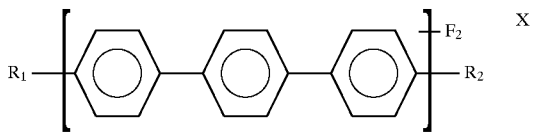

where R$_1$ and R$_2$ are independently C$_3$–C$_{12}$ alkyl or alkoxy.

The phenyl-pyrimidines described in WO 86/00087, eg of formula XI.

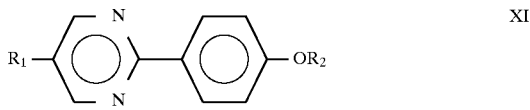

including those compounds where R$_1$ is C$_3$–C$_{12}$ alkyl and R$_2$ is given by the general formula (CH$_2$)$_n$—CHXCH$_2$CH$_3$, where n is 1 to 5 and X is CN or Cl.

The compounds described by R. Eidenschink et al in Cyclohexane derivative mit Getilteneten Smektischen Phasen at the 16$^{th}$ Freiberg Liquid Crystal Conference. Freiberg, Germany, p8. Available from E. Merck Ltd, Germany, eg of formula XII.

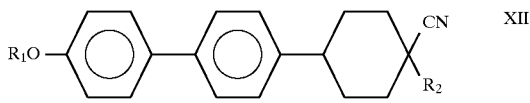

including those compounds where R$_1$ and R$_2$ are independently C$_1$–C$_{15}$ alkyl.

The difluoro-phenyl pyriridines described at the 2$^{nd}$ International Symposium on Ferroelectric Liquid Crystals, G öteborg, Sweden June 1989 by Reiffenrath et al, eg of formula XIII

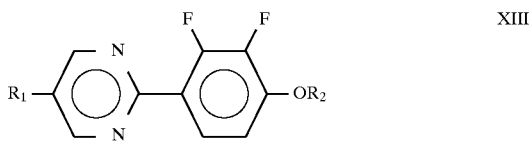

including those compounds where R$_1$ and R$_2$ are independently C$_3$–C$_9$ alkyl.

Figure 1:
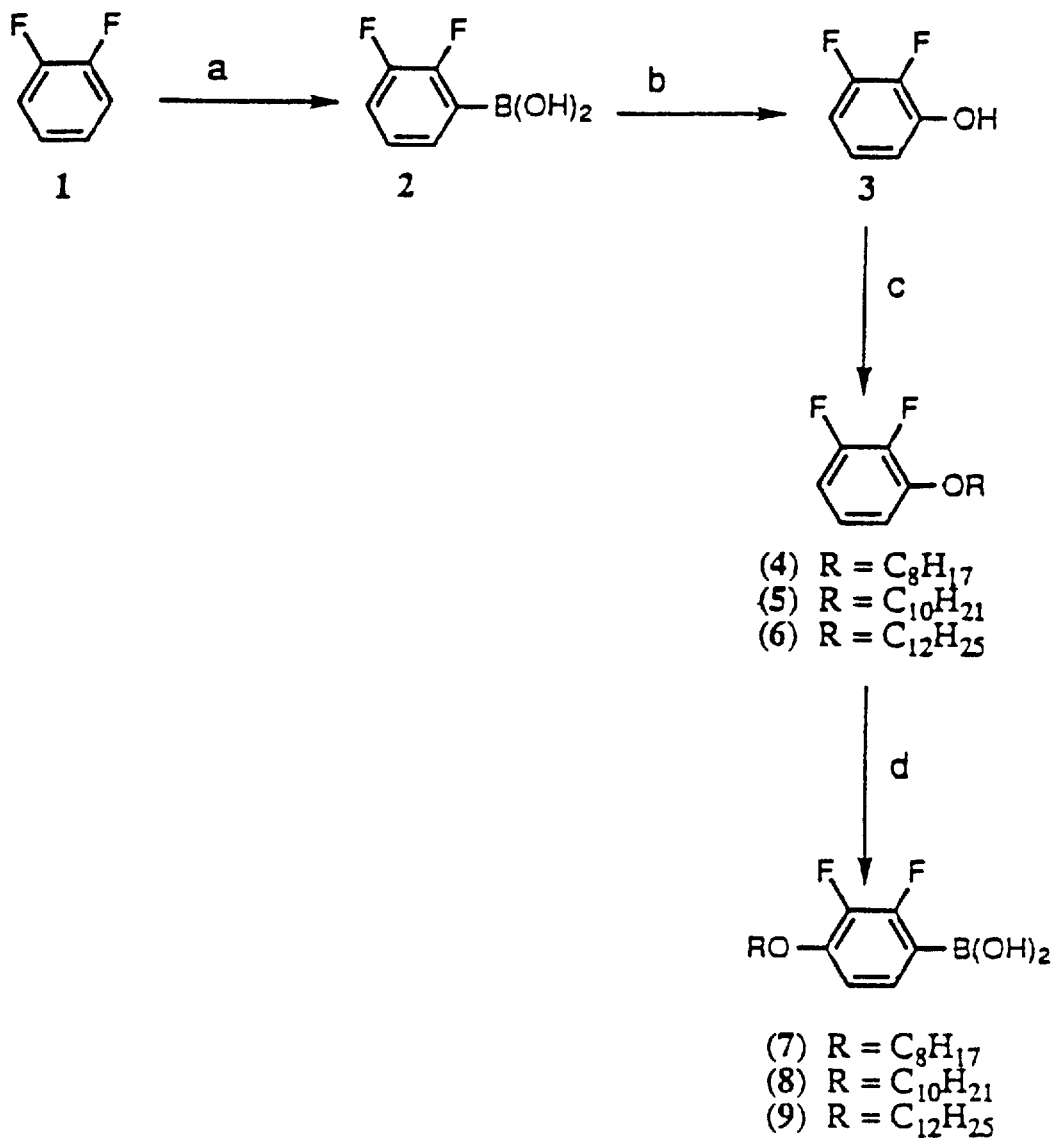
FIGS. 1–17b illustrate synthetic schemes for the synthesis of compounds.
Figure 2:
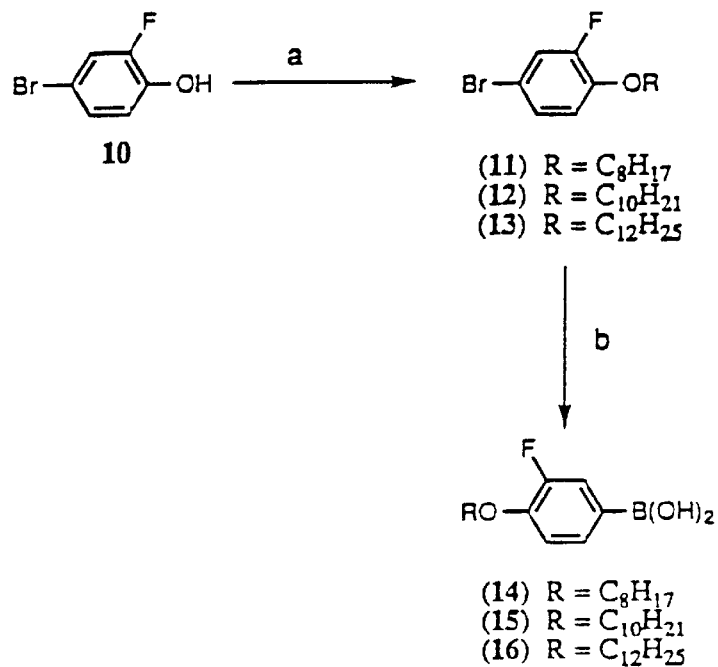
Figure 3:
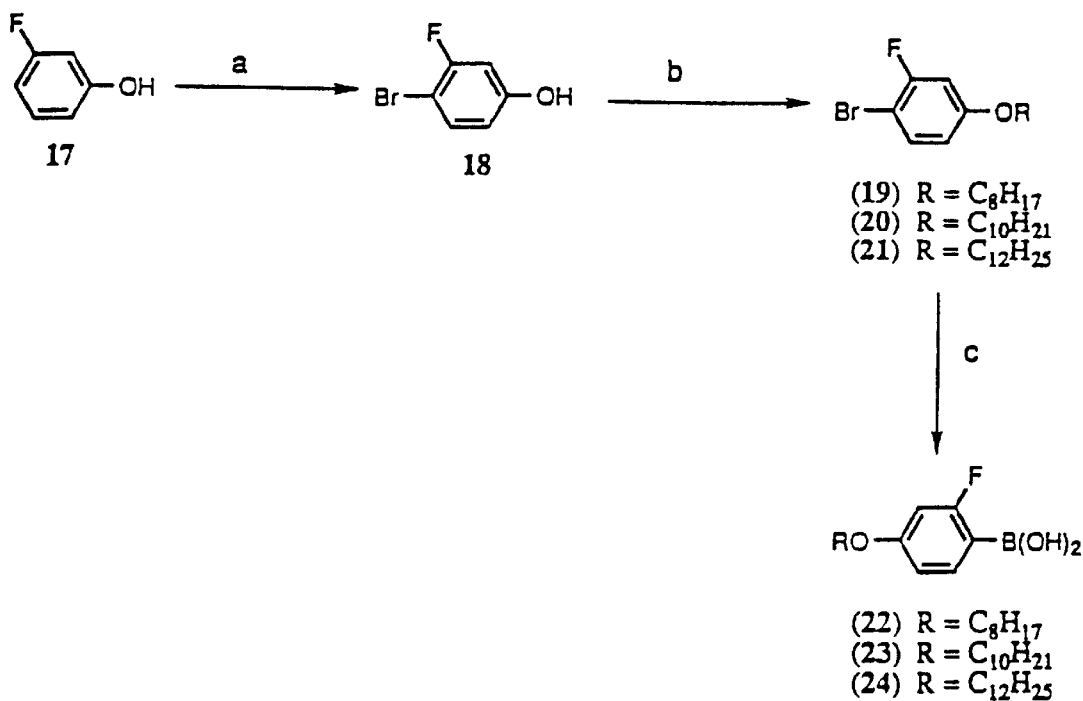
Figure 4:
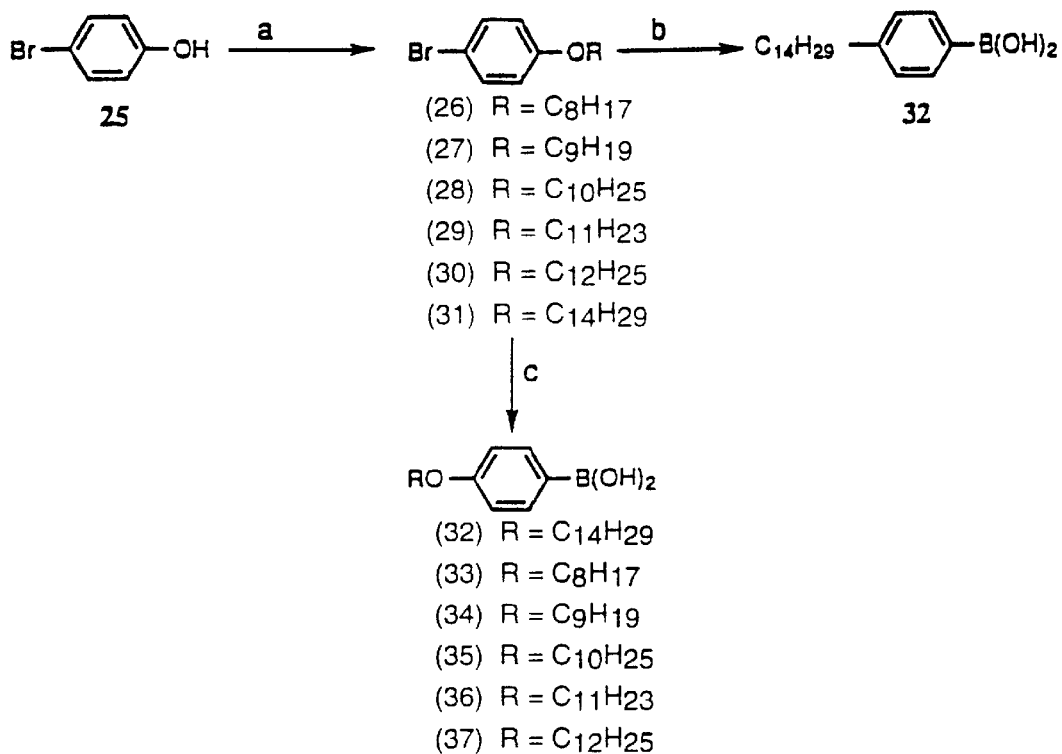
Figure 5:
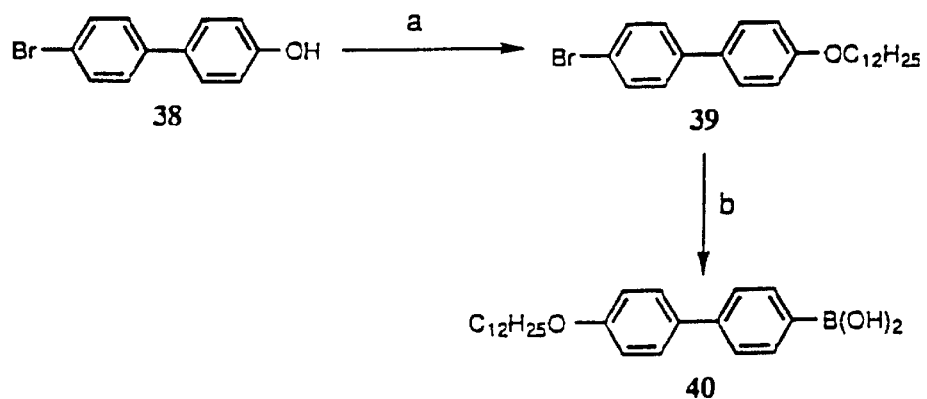
Figure 6:
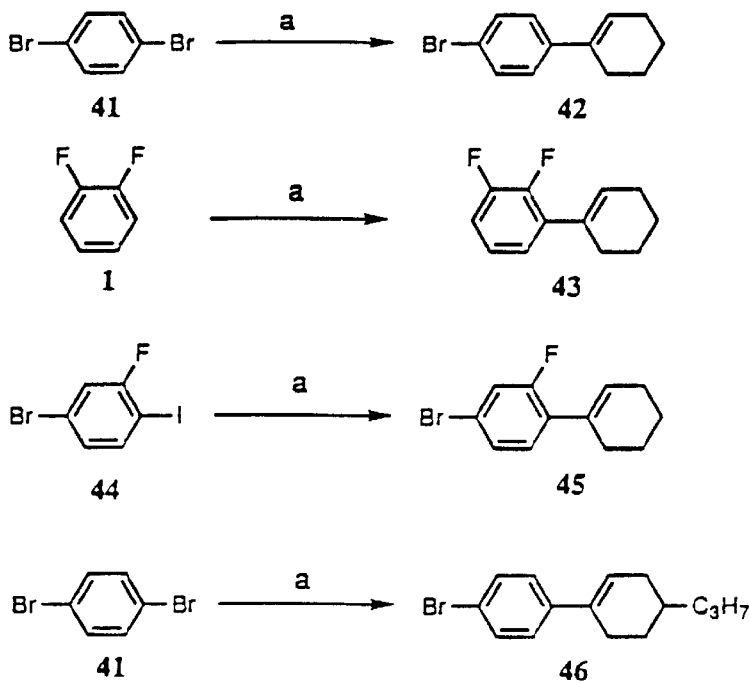
Figure 7:
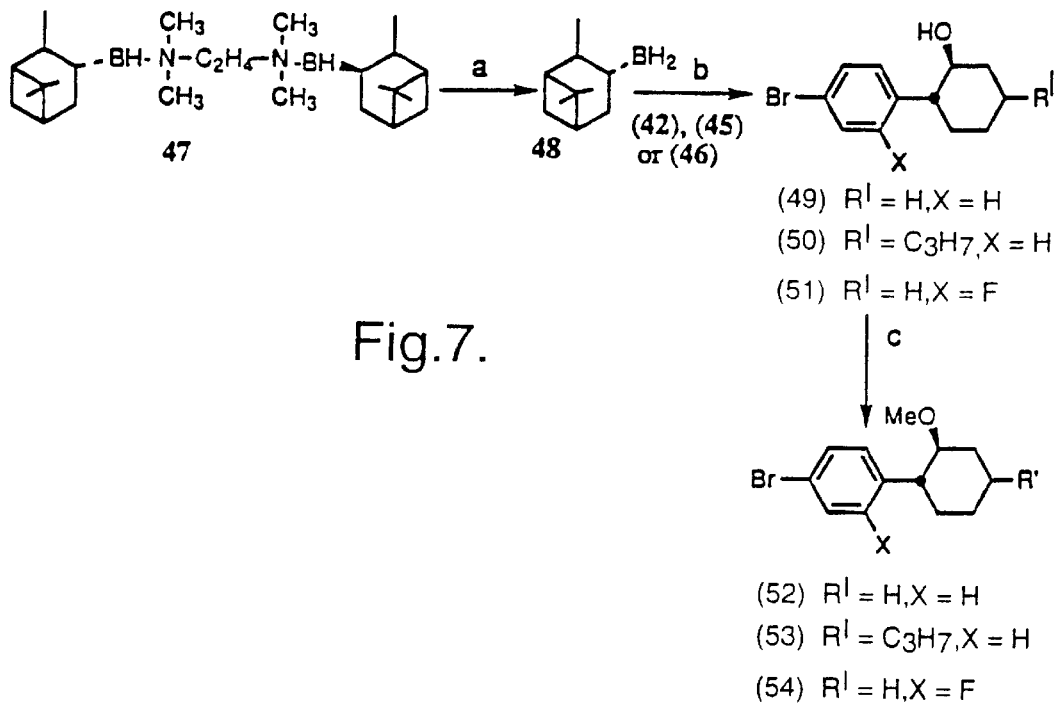
Figure 8:
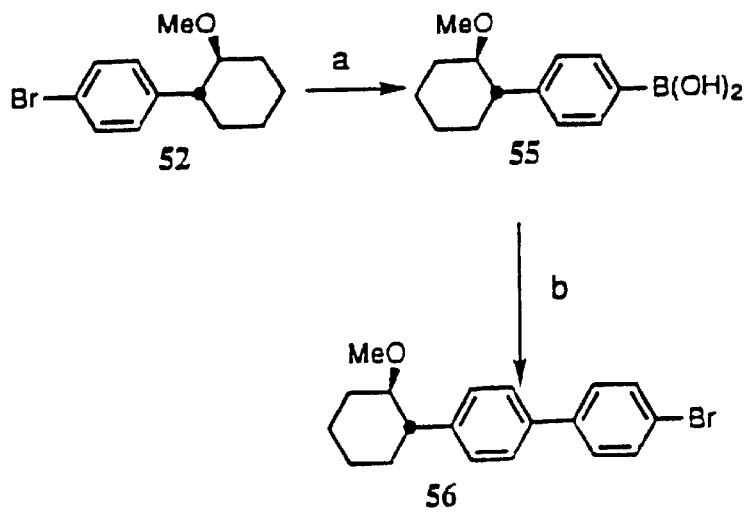
Figure 9:
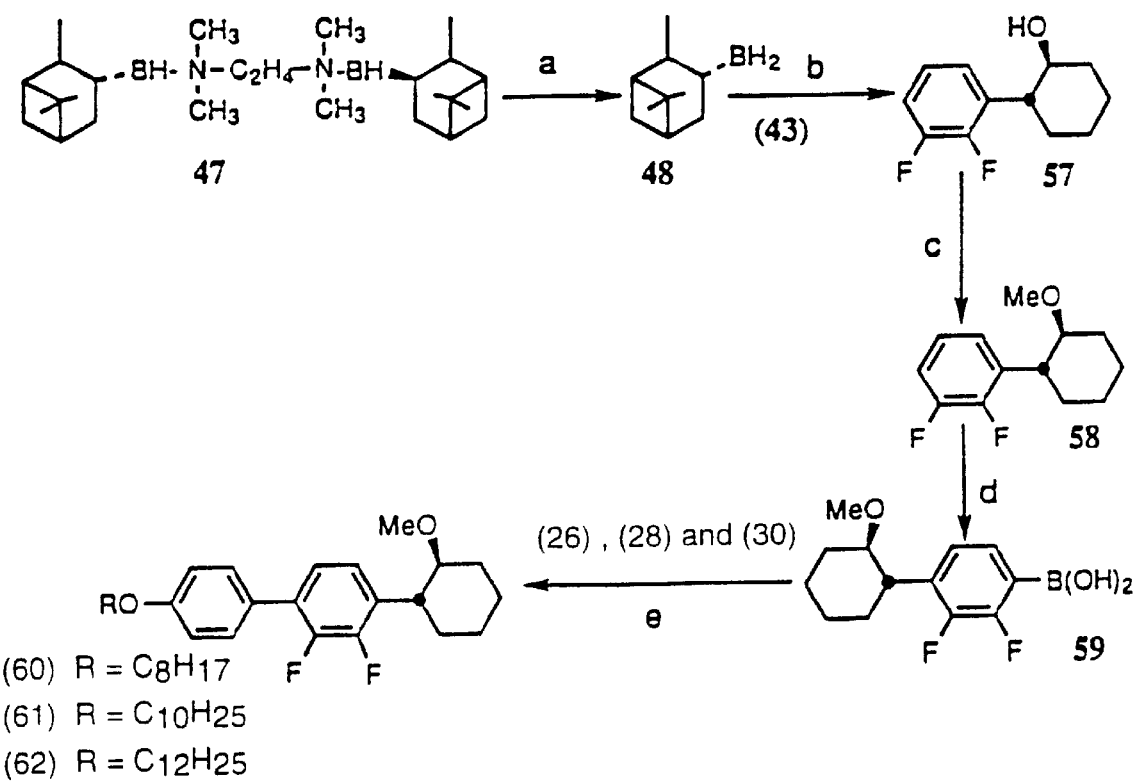
Figure 10:
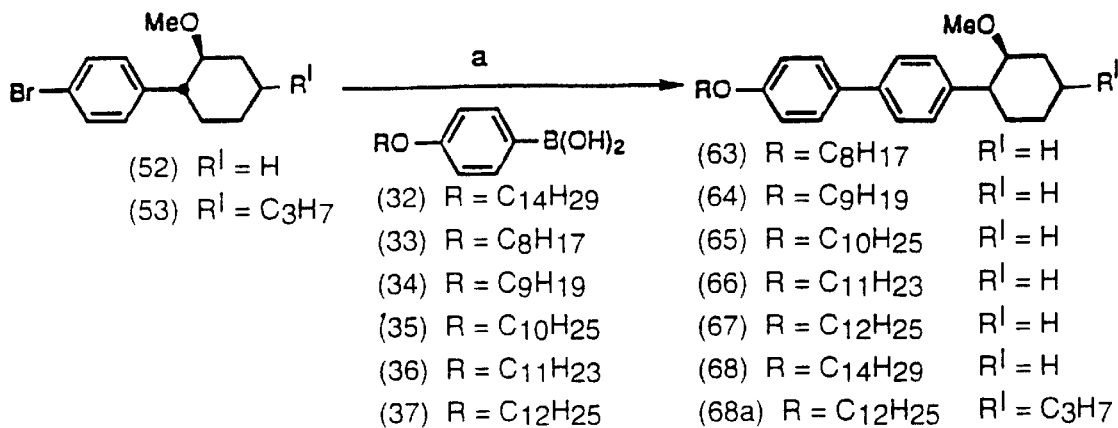
Figure 11:
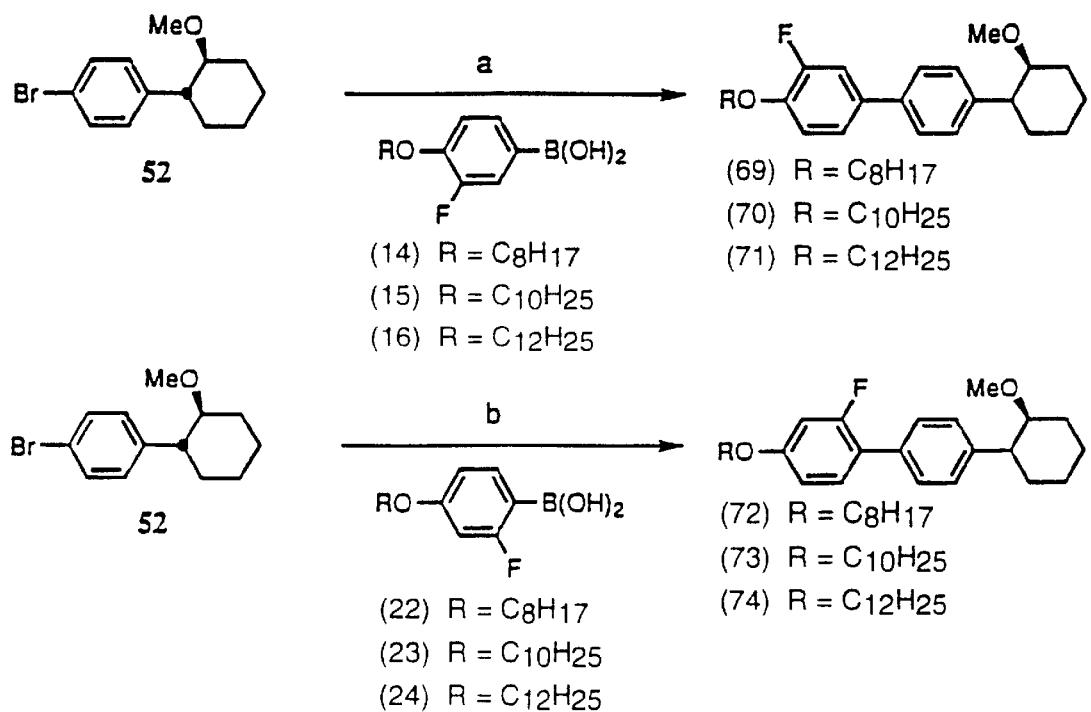
Figure 12:
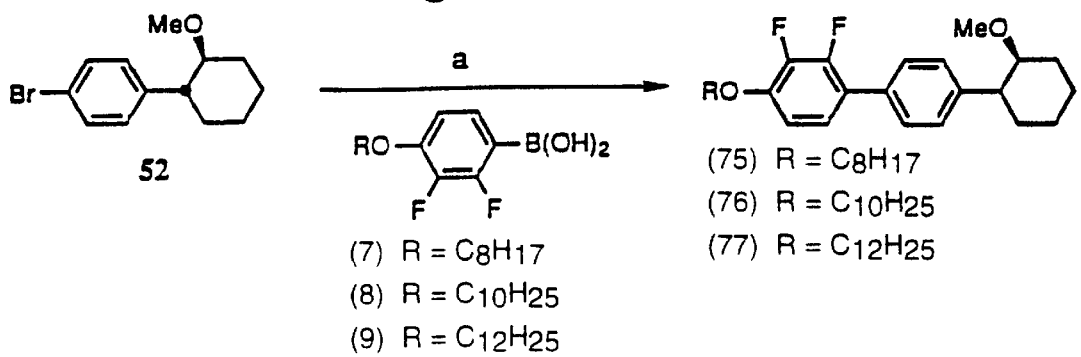
Figure 13:
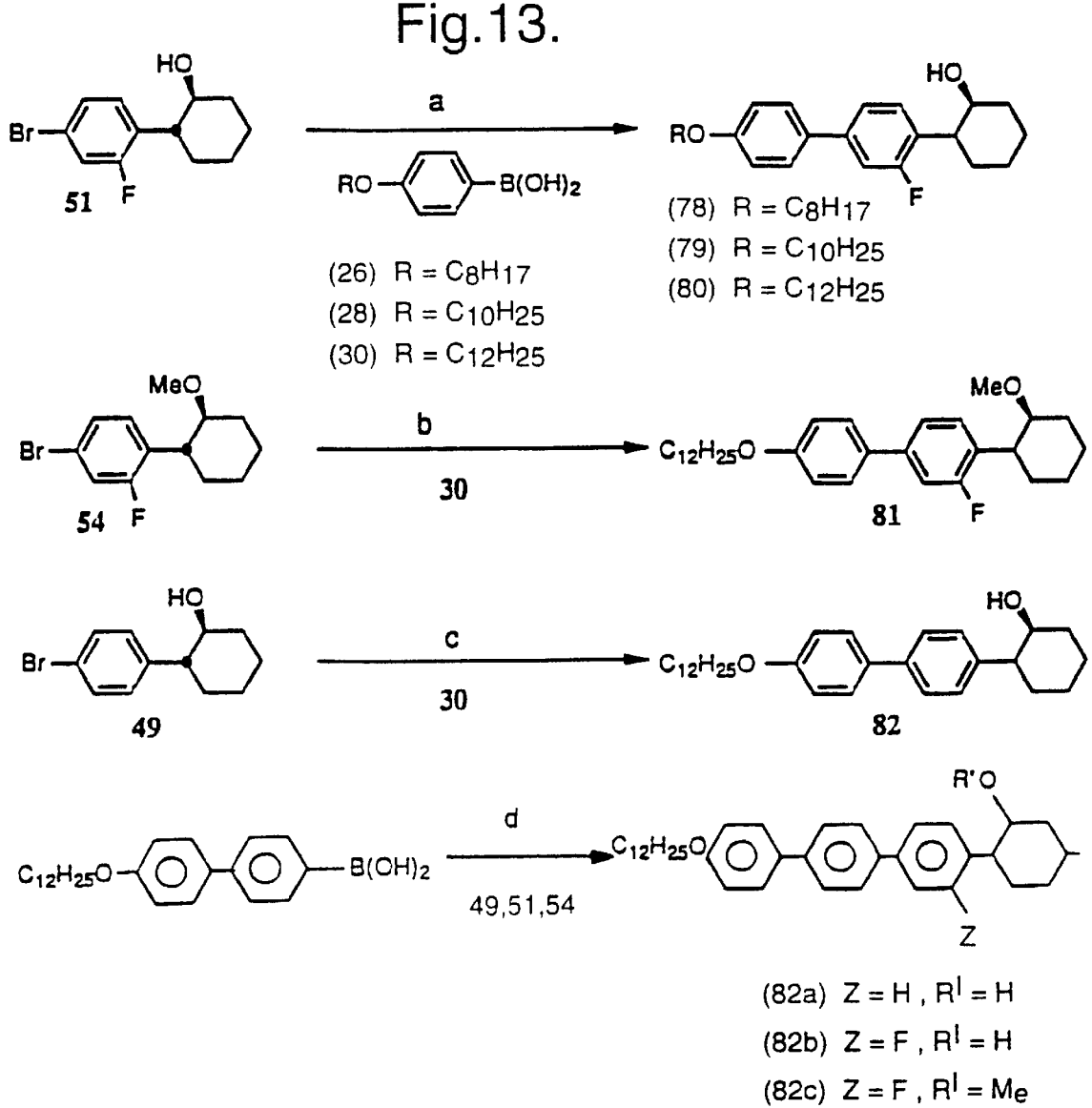
Figure 14:
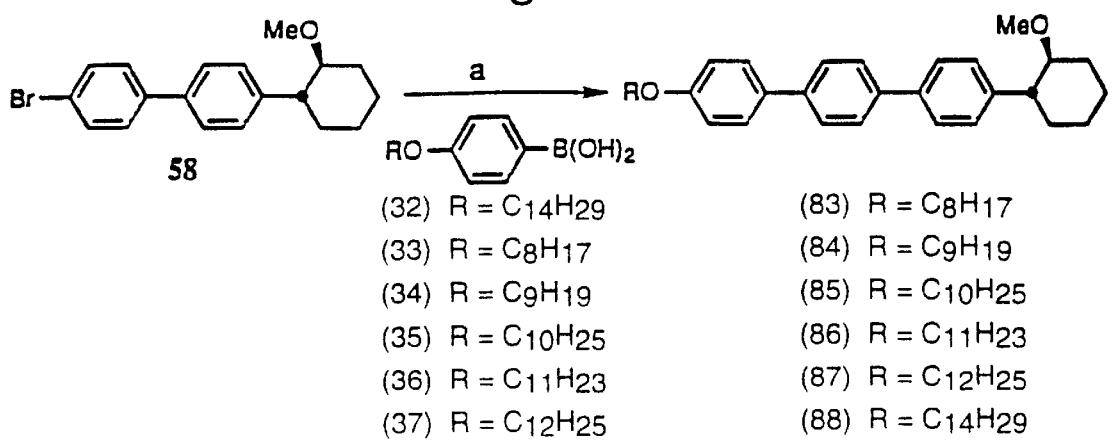
Figure 15:
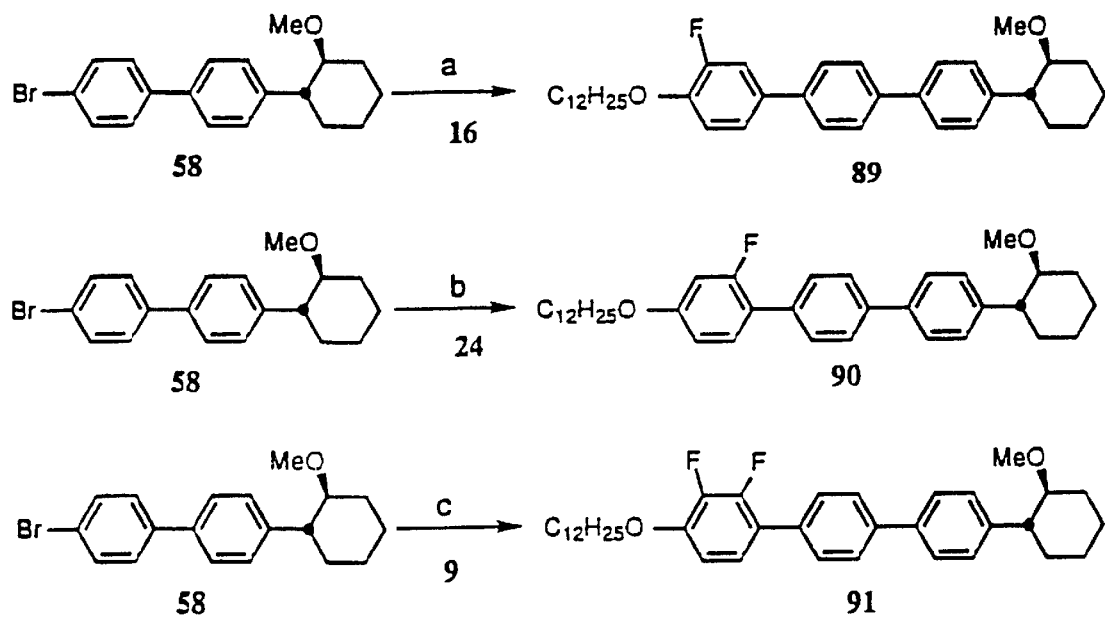
Figure 16:
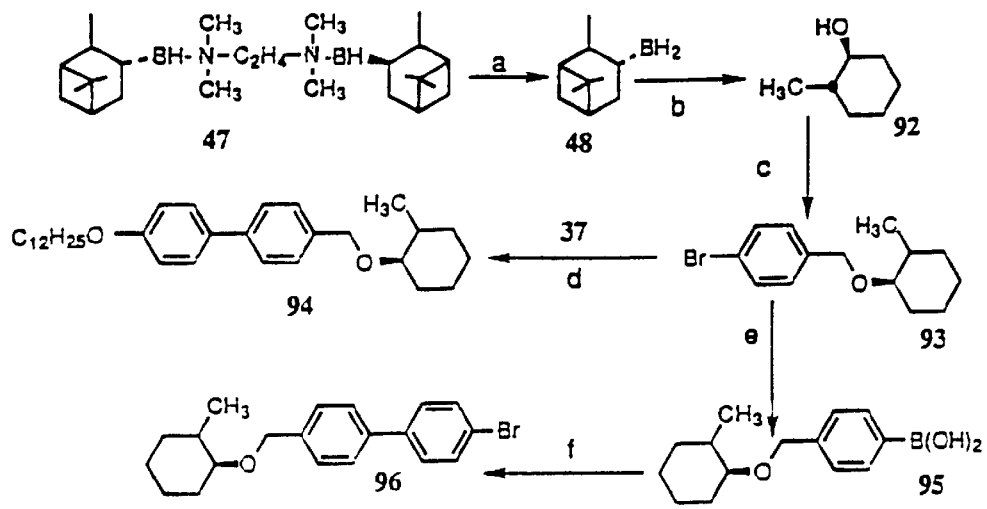
Figure 17:
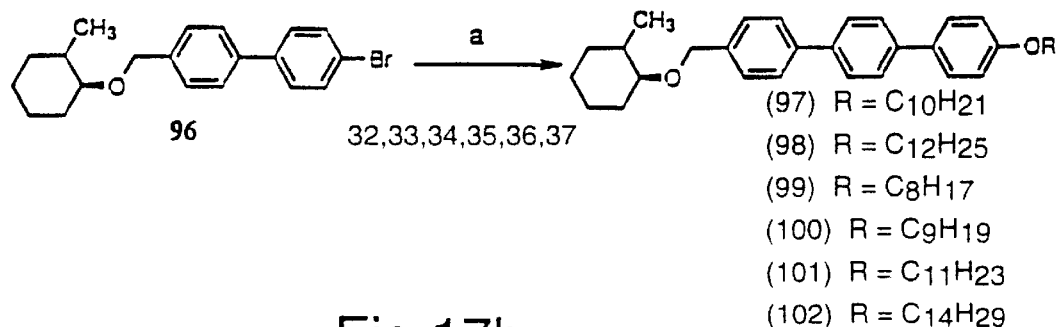
Figure 17B:
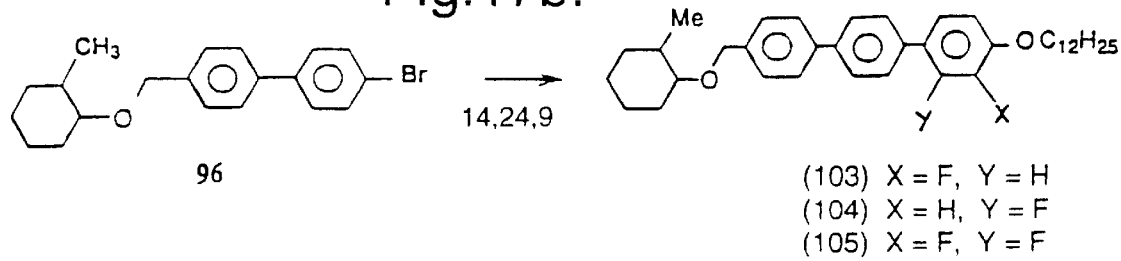
Figure 23:
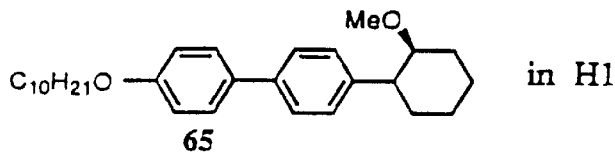
Figure 24:
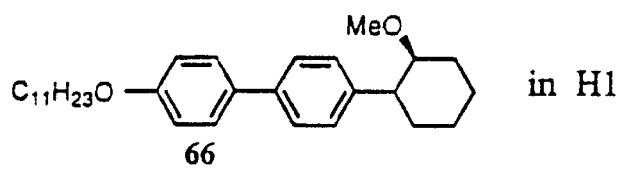
Figure 25:
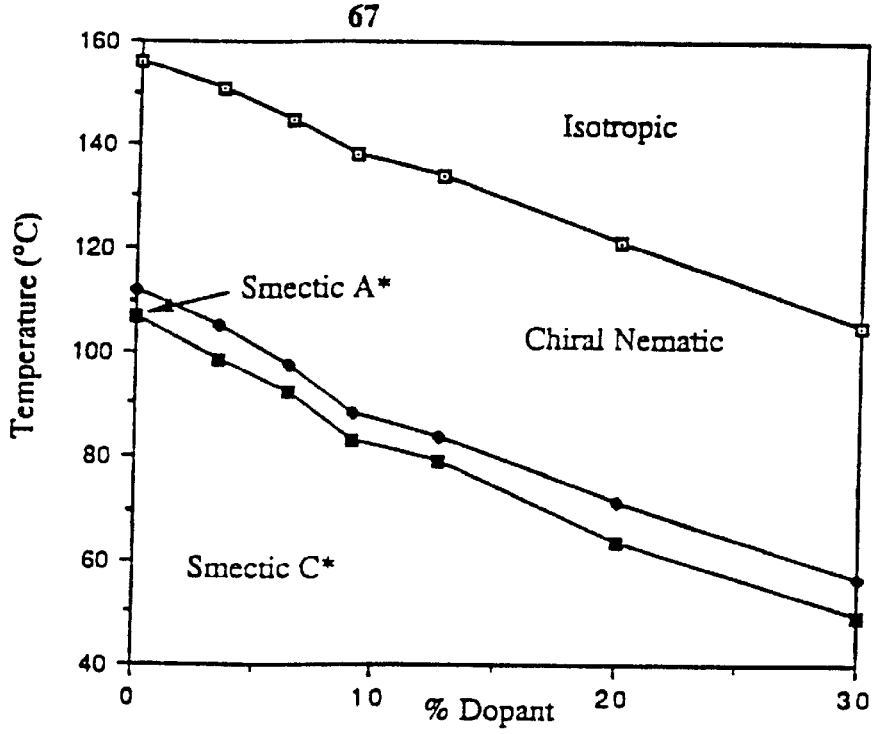
Figure 26:
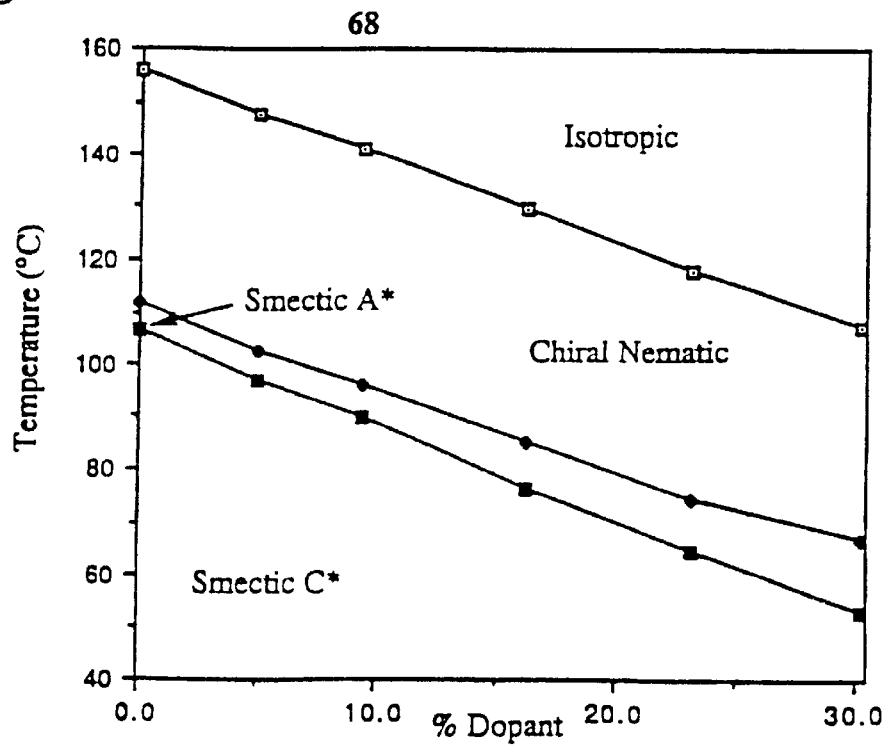
Figure 27:
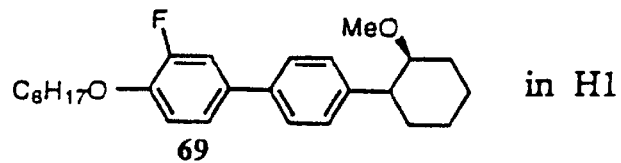
Figure 28:
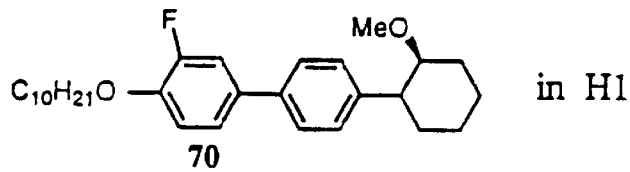
Figure 29:
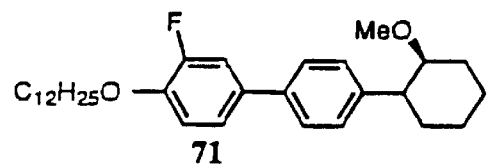
Figure 30:
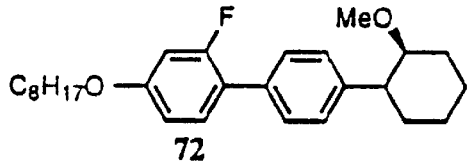
Figure 31:
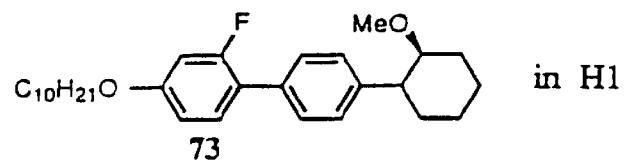
Figure 32:
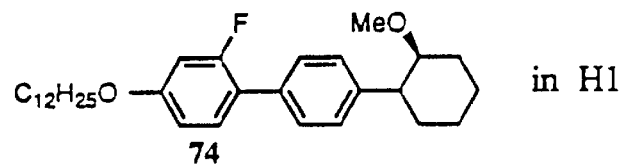
Figure 33:
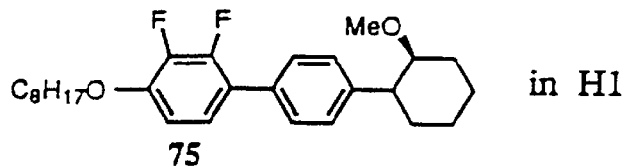
Figure 34:
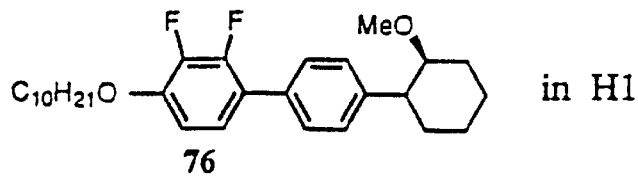
Figure 35:
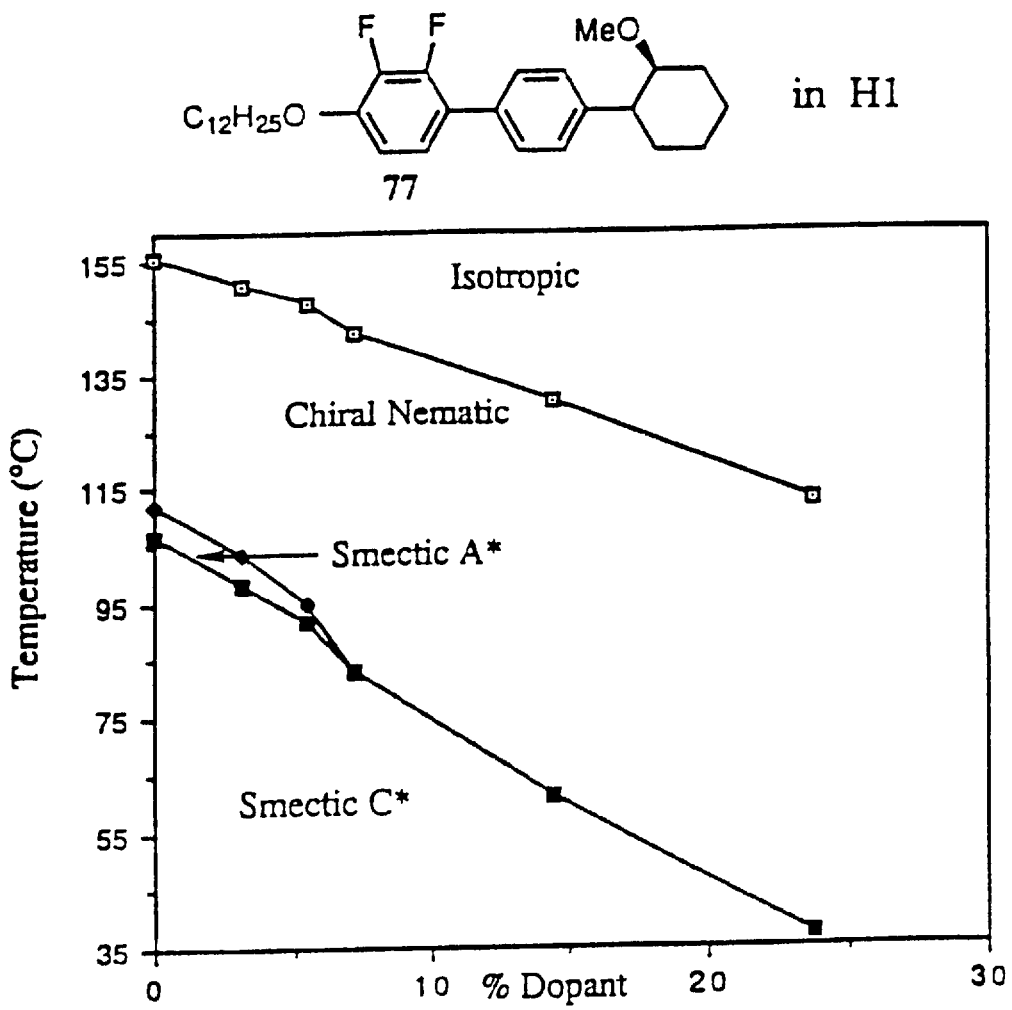
Figure 36:
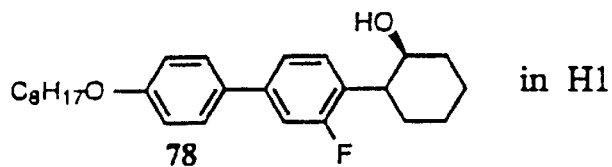
Figure 37:
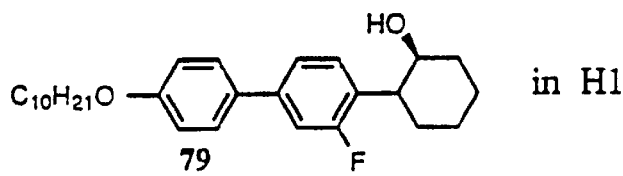
Figure 38:
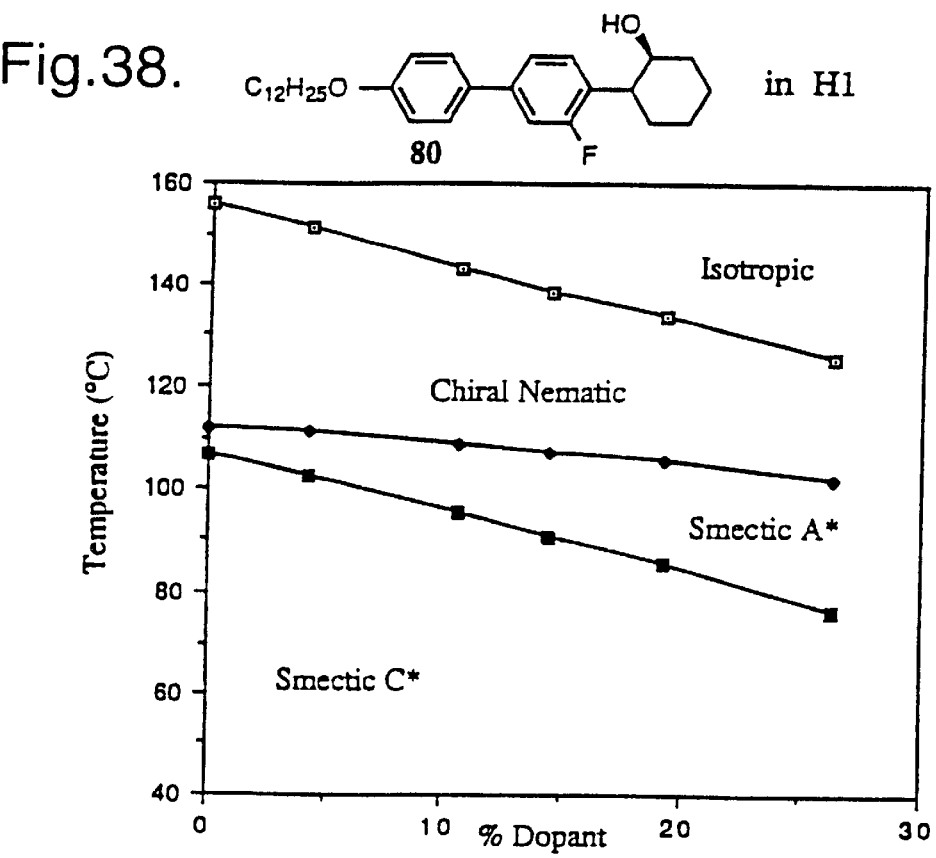
Figure 39:
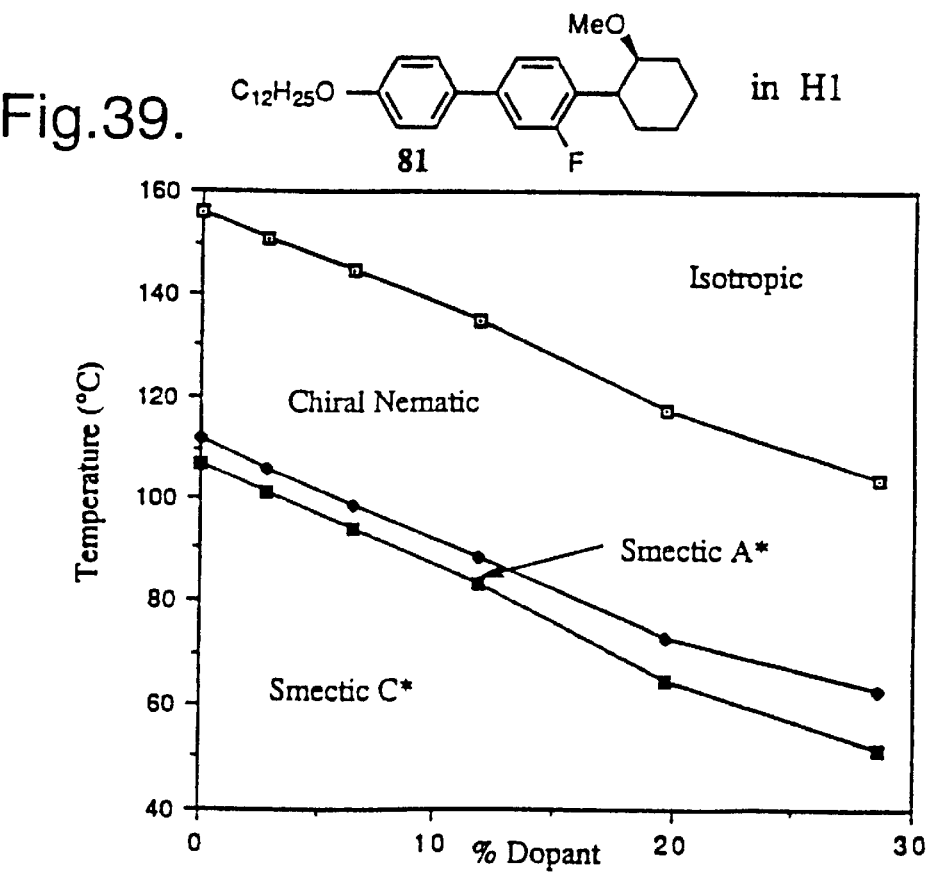
Figure 40:
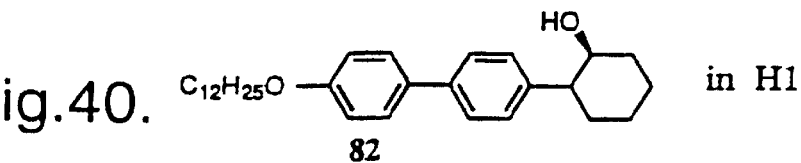
Figure 41:
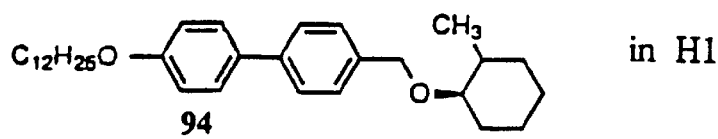
FIG. 41 illustrates a phase diagram for compound 94 in host material H1.
Figure 42:
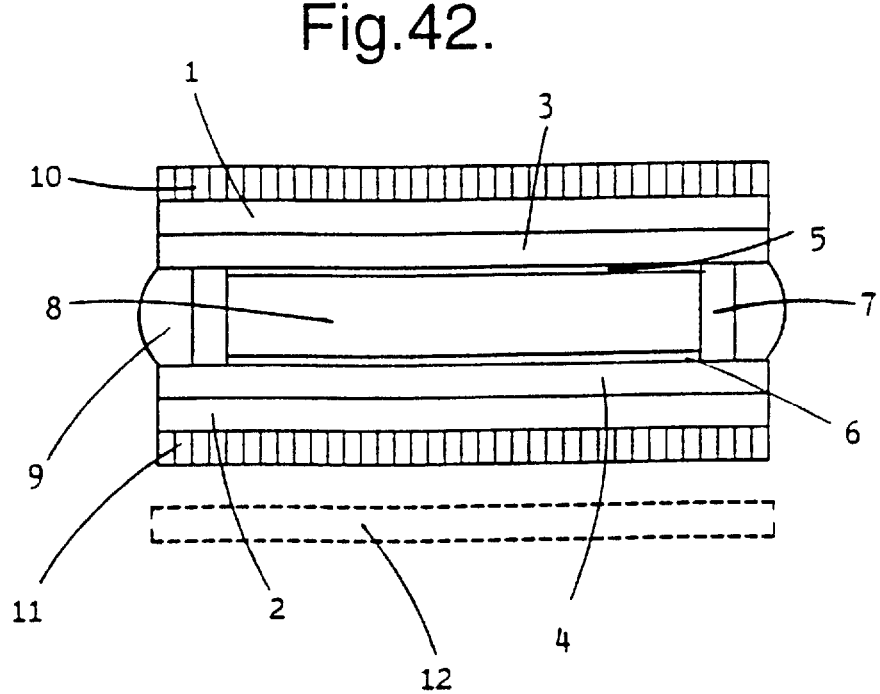
FIG. 42 illustrates a liquid crystal device.

An example of the use of a compound of Formula I in a liquid crystal material and device embodying the present invention will now be described with reference to FIG. 42.

The liquid crystal device consists of two transparent plates, 1 and 2, in this case made from glass. These plates are coated on their internal face with transparent conducting electrodes 3 and 4. An alignment layer is introduced onto the internal faces of the cell so that a planar orientation of the molecules making up the liquid crystalline material will be approximately parallel to the glass plates 1 and 2. This is done by coating the glass plates 1, 2 complete with conducting electrodes 3, 4 with layers of film 5 and 6 of a suitable polymer, eg polyimide. The electrodes 3, 4 may be formed into row and column electrodes so that the intersections between each column and row form an x, y matrix of addressable elements or pixels. Prior to the construction of the cell the films 5, 6 are rubbed with a soft tissue in a given direction, the rubbing directions being arranged parallel (same or opposite direction) upon construction of the cell. A spacer 7 eg of polymethyl methacrylate separates the glass plates 1 and 2 to a suitable distance eg 2 microns. Liquid crystal material 8 is introduced between glass plates 1, 2 by filling the space in between them. The spacer 7 is sealed with an adhesive 9 in a vacuum using an existing technique. Polarisers 10, 111 may be arranged in front of and behind the cell.

The device may operate in a transmissive or reflective mode. In the former, light passing through the device, eg from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

The materials of the present invention may also be useful in thermochromic devices, for example those devices described by D. G. McDonnell in Thermotropic Liquid Crystals, Critical reports on Applied Chemistry, Vol. 22, edited by G. W. Gray, 1987 pp 120–44 and references therein.

The materials of the present invention may be mixed with nematic hosts in order to produce materials that may be used in thermochromic devices.

The compounds of formula I may be added to host materials.

For example, H1 is a 1:1:1 mixture of the following:

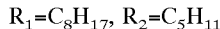
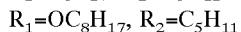
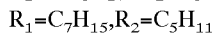

$R_1=C_8H_{17}$, $R_2=C_5H_{11}$
$R_1=OC_8H_{17}$, $R_2=C_5H_{11}$
$R_1=C_7H_{15}$, $R_2=C_5H_{11}$

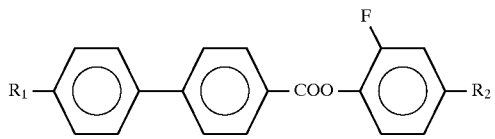

The host is a commercially available host and is widely used in ferroelectric liquid crystal mixtures.

FIGS. 18–41 are phase diagrams for compounds 60–82 and 94 in host material H1.

Tables 1 to 15 contain (where appropriate) optical rotation and melting point data and phase transition temperatures for compounds described by the present invention.

It can be seen that a particular advantage of the present invention is that a wide range of chiral materials may be made which are of high enantiomeric purity.

TABLE 1

| Compound | Melting Point/°C. | Optical Rotation/° |
|---|---|---|
| 42 | 66.5–67.5 | |
| 43 | liquid | |
| 45 | liquid | |
| 46 | 61.5–62.5 | |
| 49 | 106.0–107.0 | +8.5 |
| 50 | 39.0–40.0 | +6.4 |
| 51 | 64.5–65.5 | +17.6 |
| 52 | 38.5–39.5 | +8.9 |
| 53 | liquid | |
| 54 | liquid | +14.8 |

TABLE 1-continued

| Compound | Melting Point/°C. | Optical Rotation/° |
|---|---|---|
| 55 | liquid | |
| 56 | 94.0–96.0 | +7.4 |
| 57 | liquid | +9.0 |
| 58 | liquid | +20.4 |
| 59 | liquid | +16.6 |
| 60 | 35.0–36.0 | +2.4 |
| 61 | 39.0–40.0 | +2.5 |
| 62 | 42.0–43.0 | +11.1 |

TABLE 2

| Compound | Melting Point/°C. | Optical Rotation/° |
|---|---|---|
| 63 | 61.0–62.0 | +5.7 |
| 64 | 64.0–65.0 | +9.8 |
| 65 | 53.0–54.0 | +8.4 |
| 67 | 68.0–69.0 | +6.0 |
| 68 | 67.0–68.0 | +7.9 |

TABLE 3

| Compound | Melting Point/°C. | Optical Rotation/° |
|---|---|---|
| 69 | 46.0–47.0 | +5.9 |
| 70 | 40.0–41.0 | +7.7 |
| 71 | 50.0–51.0 | +7.1 |
| 72 | 53.0–54.0 | +7.4 |
| 73 | 40.0–41.0 | +6.6 |
| 74 | 47.0–48.0 | +8.4 |

TABLE 4

| Compound | Melting Point/°C. | Optical Rotation/° |
|---|---|---|
| 75 | liquid | +6.1. |
| 76 | liquid | +5.7 |
| 77 | 38.0–39.0 | +2.3 |
| 78 | 80.5–81.5 | +3.2 |
| 79 | 91.0–92.0 | +14.8 |
| 80 | 94.0–95.0 | +11.7 |
| 81 | 58.0–59.0 | +4.7 |
| 82 | 90.0–91.0 | +5.8 |

TABLE 5

| Compound | Optical Rotation/° |
|---|---|
| 83 | +2.7 |
| 84 | +4.7 |
| 85 | +3.7 |
| 86 | +4.2 |
| 87 | +10.5 |
| 88 | +4.6 |

TABLE 6

| Compound | Phase Transition Temperatures/°C. (Heating) | | | | | |
|---|---|---|---|---|---|---|
| 83 | K | 144.6 | N* | 150.6 | I | |
| 84 | K | 112.7 | N* | 143.7 | I | |
| 85 | K | 127.7 | N* | 142.4 | I | |
| 86 | K | 120.1 | $S_A$* | 127.4 | N* | 139.9 | I |
| 87 | K | 119.2 | $S_A$* | 130.7 | N* | 139.7 | I |
| 88 | K | 115.3 | $S_A$* | 129.6 | N* | 133.3 | I |

TABLE 7

| Compound | Phase Transition Temperatures/°C. (Cooling) | | | | | | | |
|---|---|---|---|---|---|---|---|---|
| 83 | I | 148.0 | N* | 119.1 | K | | | |
| 84 | I | 140.3 | N* | 146.6 | K | | | |
| 85 | I | 140.3 | N* | 122.6 | N* | 93.8 | K | |
| 86 | I | 137.7 | $S_A^*$ | 125.0 | Sc* | 106.1 | N* | 68.4 K |
| 87 | I | 137.5 | $S_A^*$ | 128.0 | Sc* | 104.4 | N* | 74.9 K |
| 88 | I | 130.5 | $S_A^*$ | 126.7 | Sc* | 93.8 | N* | 58.8 K |

TABLE 8

| Compound | Optical Rotation/° |
|---|---|
| 89 | +2.2 |
| 90 | +2.9 |
| 91 | +1.2 |

TABLE 9

| Compound | Phase Transition Temperatures/°C. (Heating) | | | | |
|---|---|---|---|---|---|
| 89 | K | 85.5 | $S_A^*$ | 89.0 | 103.0 I |
| 90 | K | 86.4 | N* | 88.1 | I |
| 91 | K | 76.0 | N* | 87.3 | I |

TABLE 10

| Compound | Phase Transition Temperatures/°C. (Cooling) | | | | | | |
|---|---|---|---|---|---|---|---|
| 89 | I | 100.7 | N* | 86.91 | $S_A^*$ | 59.2 Sc* | 36.9 K |
| 90 | I | 89.0 | N* | 54.8 | K | | |
| 91 | I | 85.0 | N* | 30.1 | K | | |

TABLE 11

| Compound | Phase Transition Temperatures/°C. (Cooling) | | | | | | | |
|---|---|---|---|---|---|---|---|---|
| 83 | I | 148.0 | N* | 119.1 | K | | | |
| 84 | I | 140.3 | N* | 146.6 | K | | | |
| 85 | I | 140.3 | N* | 122.6 | N* | 93.8 | K | |
| 86 | I | 137.7 | $S_A^*$ | 125.0 | Sc* | 106.1 | N* | 68.4 K |
| 87 | I | 137.5 | $S_A^*$ | 128.0 | Sc* | 104.4 | N* | 74.9 K |
| 88 | I | 130.5 | $S_A^*$ | 126.7 | Sc* | 93.8 | N* | 58.8 K |

TABLE 12

| Compound | Melting Point/°C. | Optical Rotation/° |
|---|---|---|
| 92 | liquid | −8.2 |
| 93 | liquid | −16.7 |
| 94 | 80.0–81.0 | −14.9 |
| 95 | liquid | |
| 96 | 42.5–43.5 | +7.9 |

TABLE 13

| Compound | Optical Rotation/° |
|---|---|
| 97 | +19.3 |
| 98 | +18.7 |

TABLE 14

| Compound | Phase Transition Temperatures/°C. (Cooling) | | | | | | | |
|---|---|---|---|---|---|---|---|---|
| 97 | K | 106.9 | $S_I^*$ | 127.0 | Sc* | 159.2 | N* | 161.0 I |
| 98 | K | 103.8 | $S_I^*$ | 121.1 | Sc* | 152.9 | I | |

TABLE 15

| Compound | Phase Transition Temperatures/°C. (Cooling) | | | | | | | |
|---|---|---|---|---|---|---|---|---|
| 97 | I | 158.4 | N* | 156.1 | Sc* | 113.5 | $S_I^*$ | 106.7 K |
| 98 | I | 150.8 | N* | 148.6 | Sc* | 117.4 | $S_I^*$ | 98.7 K |

TABLE 16

The Transition Temperatures (°C.) for Mixtures of Compounds 63–68a (9 wt %) in H1 § Host.

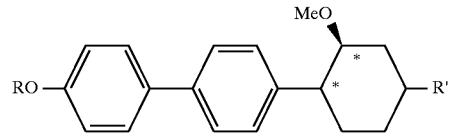

| Compound | R | R' | Transition Temperatures (°C.) |
|---|---|---|---|
| 63 | $C_8H_{17}$ | H | I 141.4 N* 79.2 $S_{C^*}$ |
| 64 | $C_9H_{19}$ | H | I 141.0 N* 81.6 $S_{C^*}$ |
| 65 | $C_{10}H_{21}$ | H | I 140.4 N* 86.8 $S_A^*$ 83.6 $S_{C^*}$ |
| 66 | $C_{11}H_{23}$ | H | I 140.9 N* 86.8 $S_A^*$ 83.6 $S_{C^*}$ |
| 67 | $C_{12}H_{25}$ | H | I 141.5 N* 92.4 $S_A^*$ 87.6 $S_{C^*}$ |
| 68 | $C_{14}H_{29}$ | H | I 140.6 N* 96.0 $S_A^*$ 88.0 $S_{C^*}$ |
| 68a¶ | $C_{12}H_{25}$ | $C_3H_7$ | I 145.1 N* 100.3 $S_A^*$ 86.5 $S_{C^*}$ |

§ Transition Temperatures of H1 Host are I 152.0 N 113.0 $S_A$ 107.0 $S_C$ 28.0 $S_I$ ¶ Transition Temperatures of Pure Material are C 55.6 N* 62.1 I

TABLE 17

Spontaneous Polarization ($P_S$) and Tilt Angle (q) for Mixtures of Compounds 63–68a (9 wt %) in H1 Host.

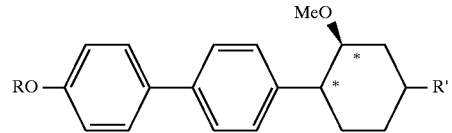

| Compound | R | R' | $P_S$ (nC cm$^{-2}$) | q (°) |
|---|---|---|---|---|
| 63 | $C_8H_{17}$ | H | 2.8 | 28 |
| 64 | $C_9H_{19}$ | H | 4.9 | 29 |
| 65 | $C_{10}H_{21}$ | H | 3.4 | 30 |
| 66 | $C_{11}H_{23}$ | H | 2.6 | 27 |
| 67 | $C_{12}H_{25}$ | H | 3.4 | 29 |
| 68 | $C_{14}H_{29}$ | H | 2.5 | 27 |
| 68a | $C_{12}H_{25}$ | $C_3H_7$ | 3.9 | 28 |

TABLE 18

The Transition Temperatures (°C.) for Mixtures of Compounds 75, 69, 72, 60 and 78 (9 wt %) in H1 § Host.

[Structure: $C_8H_{17}O$-phenyl($R_1$,$R_2$)-phenyl($R_3$,$R_4$)-cyclohexyl($R_5$)]

| Compound | $R_1$ | $R_2$ | $R_3$ | $R_4$ | $R_5$ | Transition Temperatures (°C.) |
|---|---|---|---|---|---|---|
| 75 | F | F | H | H | OMe | I 139.4 N* 66.8 $S_C$* |
| 69 | F | H | H | H | OMe | I 139.5 N* 68.2 $S_C$* |
| 72 | H | F | H | H | OMe | I 139.9 N* 71.6 $S_C$* |
| 60 | H | H | F | F | OMe | I 139.8 N* 65.4 $S_C$* |
| 78 | H | H | H | F | OH | I 145.5 N* 104.4 $S_A$* 92.9 $S_C$* |

§ Transition Temperatures of H1 Host are I 152.0 N 113.0 $S_A$ 107.0 $S_C$ 28.0 $S_I$

TABLE 19

The Transition Temperatures (°C.) for Mixtures of Compounds 76, 70, 73, 61 and 79 (9 wt %) in H1 Host.

[Structure: $C_{10}H_{21}O$-phenyl($R_1$,$R_2$)-phenyl($R_3$,$R_4$)-cyclohexyl($R_5$)]

| Compound | $R_1$ | $R_2$ | $R_3$ | $R_4$ | $R_5$ | Transition Temperatures (°C.) |
|---|---|---|---|---|---|---|
| 76 | F | F | H | H | OMe | I 140.3 N* 73.7 $S_C$* |
| 70 | F | H | H | H | OMe | I 140.3 N* 75.2 $S_C$* |
| 73 | H | F | H | H | OMe | I 140.8 N* 78.1 $S_C$* |
| 61 | H | H | F | F | OMe | I 139.8 N* 72.4 $S_C$* |
| 79 | H | H | H | F | OH | I 146.0 N* 108.8 $S_A$* 96.0 $S_C$* |

TABLE 20

The Transition Temperatures (°C.) for Mixtures of Compounds 77, 71, 74, 62, 81, 80 and 82 (9 wt %) in H1 Host.

[Structure: $C_{12}H_{25}O$-phenyl($R_1$,$R_2$)-phenyl($R_3$,$R_4$)-cyclohexyl($R_5$)]

| Compound | $R_1$ | $R_2$ | $R_3$ | $R_4$ | $R_5$ | Transition Temperatures (°C.) |
|---|---|---|---|---|---|---|
| 77 | F | F | H | H | OMe | I 139.6 N* 78.5 $S_C$* |
| 71 | F | H | H | H | OMe | I 140.4 N* 80.0 $S_C$* |
| 74 | H | F | H | H | OMe | I 140.8 N* 86.6 $S_C$* |
| 62 | H | H | F | F | OMe | I 140.5 N* 83.5 $S_C$* |
| 81 | H | H | H | F | OMe | I 140.6 N* 93.5 $S_A$* 87.5 $S_C$* |
| 80 | H | H | H | F | OH | I 145.2 N* 109.6 $S_A$* 97.3 $S_C$* |
| 82 | H | H | H | H | OH | I 146.4 N* 112.8 $S_A$* 95.8 $S_C$* |

TABLE 21

Spontaneous Polarization ($P_S$) and Tilt Angle (q) for Mixtures of Compounds 77, 71, 74 62, 81, 80 and 82 (9 wt %) in H1 Host.

[Structure: $C_{12}H_{25}O$-phenyl($R_1$,$R_2$)-phenyl($R_3$,$R_4$)-cyclohexyl($R_5$)]

| Compound | $R_1$ | $R_2$ | $R_3$ | $R_4$ | $R_5$ | $P_S$(nC cm$^{-2}$) | q (°) |
|---|---|---|---|---|---|---|---|
| 77 | F | F | H | H | OMe | 2.1 | 27 |
| 71 | F | H | H | H | OMe | 2.9 | 28 |
| 74 | H | F | H | H | OMe | | |
| 62 | H | H | F | F | OMe | | |
| 81 | H | H | H | F | OMe | | |
| 80 | H | H | H | F | OH | | |
| 82 | H | H | H | H | OH | | |

TABLE 22

The Transition Temperatures (°C.) for Compounds 83–88.

[Structure: RO-phenyl-phenyl-phenyl-cyclohexyl(MeO)]

| Compound | R | Transition Temperatures (°C.) |
|---|---|---|
| 83 | $C_8H_{17}$ | I 150.6 N* 144.6 K |
| 84 | $C_9H_{19}$ | I 147.4 N* 123.1 K |
| 85 | $C_{10}H_{21}$ | I 143.0 N* 123.2 $S_A$* 101.6 K |
| 86 | $C_{11}H_{23}$ | I 140.1 N* 127.2 $S_A$* 107 $S_C$* 81.5 K |
| 87 | $C_{12}H_{25}$ | I 139.3 N* 129.8 $S_A$* 104 $S_C$* 87.3 K |
| 88 | $C_{14}H_{29}$ | I 135.1 N* 131 $S_A$* 97.6 $S_C$* 70.2 K |

§ Transition Temperatures of H1 Host are I 152.0 N 113.0 $S_A$ 107.0 $S_C$ 28.0 $S_I$

TABLE 23

The Transition Temperatures (°C.) for Compounds 89–91 and 82a–82c.

[Structure: $C_{12}H_{25}O$-phenyl($R_1$,$R_2$)-phenyl-phenyl($R_3$)-cyclohexyl($R_4$O)]

| Compound | $R_1$ | $R_2$ | $R_3$ | $R_4$ | Transition Temperatures (°C.) |
|---|---|---|---|---|---|
| 89 | F | H | H | OMe | I 103.7 N* 90.4 $S_A$* 62.4 $S_C$* 55.1 |
| 90 | H | F | H | OMe | I 89.0 N* 54.8 K |
| 91 | F | F | H | OMe | I 87.6 N* 60.6 K |
| 82a | H | H | H | OH | |
| 82b | H | H | F | OH | I 190.0 $S_A$* 188.5 $S_C$* 137 K |
| 82c | H | H | F | OMe | I 115.6 N* 114.7 $S_A$* 86.5 $S_C$* 72 K |

TABLE 24

The Transition Temperatures (°C.) for Compounds
97–102 and 103–105.

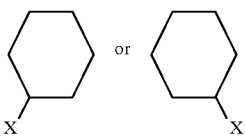

| Compound | $R_1$ | $R_2$ | $R_3$ | Transition Temperatures (°C.) |
|---|---|---|---|---|
| 99  | $C_8H_{17}$  | H | H | I 169.6 N* 165.9 $S_C$* 139.6 $S_X$* 120.4 K |
| 100 | $C_9H_{19}$  | H | H | I 167.1 N* 164.3 $S_C$* 141.1 $S_X$* 122.5 K |
| 97  | $C_{10}H_{21}$ | H | H | I 166.8 N* 164.8 $S_C$* 134.6 $S_X$* 111.0 K |
| 101 | $C_{11}H_{23}$ | H | H | I 164.9 N* 161.8 $S_C$* 128.7 $S_X$* 107.9 K |
| 98  | $C_{12}H_{25}$ | H | H | I 162.2 N* 161.1 $S_A$* 160.6 $S_C$* 124.5 $S_X$* 105.2 K |
| 102 | $C_{14}H_{29}$ | H | H | I 159.2 $S_A$* 156.8 $S_C$* 124 $S_X$* 109 K |
| 103 | $C_{12}H_{25}$ | F | H | I 124.5 N* 121.8 $S_A$* 118.8 $S_C$* 97.1 $S_X$* 81.2 K |
| 104 | $C_{12}H_{25}$ | H | F | |
| 105 | $C_{12}H_{25}$ | F | F | |

§ Transition Temperatures of H1 Host are I 152.0 N 113.0 $S_A$ 107.0 $S_C$ 28.0 $S_I$

We claim:

1. An optically active compound of formula I:

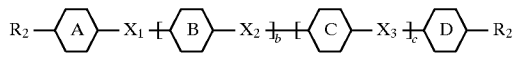

wherein A, B, C, D are independently selected from any of phenyl, pyridine, pyrimidine, cyclohexyl, or substituted phenyl and at least one of the cyclohexyl groups:

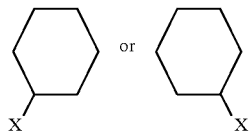

must be present:
wherein X is any one of OH, $OR_3$, $R_3$, $CH_2OR_3$, F, Cl, $OCF_3$, $CF_3$, $CH_2F$, $CHF_2$, or CN, where $R_3$ is $C_{1-5}$ alkyl and may itself contain a chiral centre;
$R_1$ is $C_{1-16}$ straight or branched chain alkyl or alkoxy and may contain a chiral centre;
$R_2$ is $C_{1-16}$ straight or branched chain alkyl or alkoxy and may contain a chiral centre or $R_2$ is H;
substituted phenyl is given by the formula:

wherein Y is individually selected from F, Cl or CN and y is 1–4;
$X_1$, and $X_2$, and $X_3$ are single bond;
b and c are independently 0 or 1;
provided that at least one of A, B, C or D is substituted phenyl wherein Y is F.

2. A compound according to claim 1 wherein those groups A, B, C, D which are not given by the cyclohexyl groups:

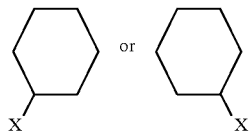

are phenyl or substituted phenyl;
X is selected from any one of OH, $OR_3$, $R_3$, F, $CF_3$, $CH_2F$, $CHF_2$, or CN, wherein
$R_3$ is a methyl group or an ethyl group;
$R_1$ is $C_{4-12}$ alkyl or alkoxy and $R_2$ is $C_{4-12}$ alkyl or alkoxy or H;
Y if present is F and y=1 or 2; and
the total of b and c is 1 or 2.

3. A liquid crystal mixture comprising at least one of the compounds of claim 1.

4. A liquid crystal device comprising a layer of liquid crystal material contained between two spaced cell walls each bearing electrode structures and surface treated on facing surfaces to align liquid crystal material molecules, characterized in that the liquid crystal material includes the material as described in claim 1.

5. A liquid crystal mixture containing any of the compounds of claim 1 and a host material of the following general formula:

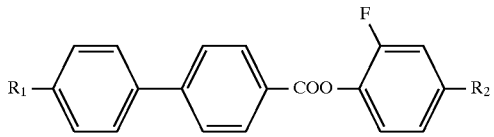

where $R_1$ and $R_2$ are independently $C_3$–$C_{12}$ alkyl or alkoxy.

6. A liquid crystal mixture containing any of the compounds of claim 1 and a host material of the following general formula

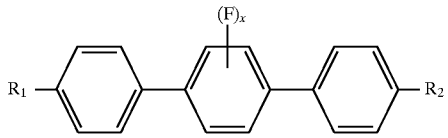

where $R_1$ and $R_2$ are independently $C_3$–$C_{12}$ alkyl or alkoxy, x is 1 and F may be on any one of the available substitution positions on the phenyl ring specified.

7. A liquid crystal mixture containing any of the compounds of claim 1 and a host material of the following general formula:

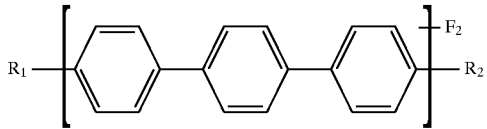

where $R_1$ and $R_2$ are independently $C_3$–$C_{12}$ alkyl or alkoxy.

8. A liquid crystal mixture containing any of the compounds of claim 1 and a host material of the following general formula:

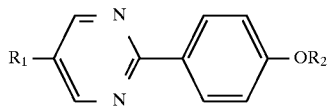

where $R_1$ is $C_3$–$C_{12}$ alkyl and $R_2$ is given by the general formula $(CH_2)_n$—$CHXCH_2CH_3$,
where n is 1 to 5 and X is CN or Cl.

9. A liquid crystal mixture containing any of the compounds of claim 1 and a host material of the following general formula:

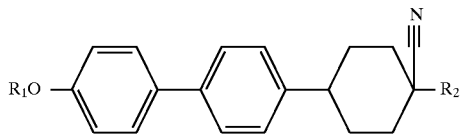

where $R_1$ and $R_2$ are independently $C_1$–$C_{15}$ alkyl or alkoxy.

10. A liquid crystal mixture containing any of the compounds of claim 1 and a host material of the following general formula:

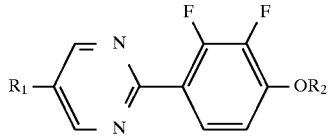

where $R_1$ and $R_2$ are independently $C_3$–$C_9$ alkyl or alkoxy.

11. An electroclinic device comprising two spaced cell walls each bearing electrode structures and treated on at least one facing surface with an alignment layer, a layer of a smectic liquid crystal material enclosed between the cell walls, characterised in that the liquid crystal material contains one or more of the compounds described by claim 1.

12. A thermochromic liquid crystal device comprising a layer of cholesteric liquid crystal material contained between two cell walls characterised in that the liquid crystal material contains one or more of the compounds described in claim 1.

13. A device according to claim 12 wherein at least one of the cell walls is surface profiled in a fine grating to align the liquid crystal molecules.

14. An optically active dopant suitable for inclusion in a ferroelectric smectic liquid crystal mixture, said dopant having the structure of general formula I of claim 1.

15. A compound having formula I

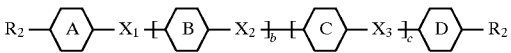

wherein A, B, C, D are independently selected from any of phenyl, pyridine, pyrimidine, cyclohexyl, or substituted phenyl and at least one of the cyclohexyl groups:

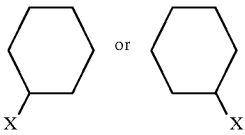

must be present:
wherein X is any one of OH, $OR_3$, $R_3$, $CH_2OR_3$, F, Cl, $OCH_3$, $CF_3$ $CHF_3$, or CN, where $R_3$ is $C_{1-5}$ alkyl and may itself contain a chiral centre;
$R_1$ is $C_{1-16}$ straight or branched chain alkyl or alkoxy and may contain a chiral centre;
$R_2$ is $C_{1-16}$ straight or branched chain alkyl or alkoxy and may contain a chiral centre or $R_2$ is H;
substituted phenyl is given by the formula;

wherein Y is individually selected from F, Cl or CN, and y is 1–4;
$X_1$, and $X_2$, and $X_3$ are single bond;
b and c are independently 0 or 1;
provided that when X is OMe or CN then there are at least 3 rings present provided that at least one of A, B, C or D is substituted phenyl wherein Y is F.

* * * * *

UNITED STATES PATENT AND TRADEMARK OFFICE
CERTIFICATE OF CORRECTION

PATENT NO.   : 5,853,613
DATED        : December 29, 1998
INVENTOR(S)  : Goodby et al It is certified that error appears in the above-identified patent and that said letters patent is hereby corrected as shown below:

Claims 1 and 15, line 2 of each, substitute the following formula:

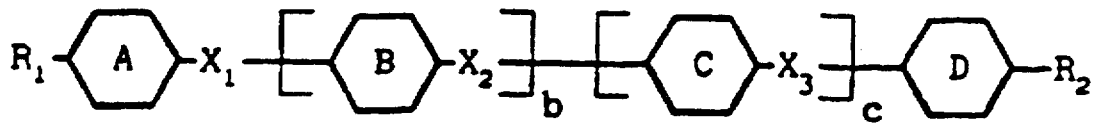

Signed and Sealed this

Fifteenth Day of June, 1999

Attest:

Q. TODD DICKINSON

Attesting Officer

Acting Commissioner of Patents and Trademarks